(12) United States Patent
Nakauchi et al.

US011844336B2

(10) Patent No.: US 11,844,336 B2
(45) Date of Patent: *Dec. 19, 2023

(54) METHOD FOR PRODUCING CHIMERIC ANIMAL

(71) Applicants: THE UNIVERSITY OF TOKYO, Bunkyo-ku (JP); THE BOARD OF TRUSTEES OF THE LELAND STANFORD JUNIOR UNIVERSITY, Stanford, CA (US)

(72) Inventors: Hiromitsu Nakauchi, Tokyo (JP); Hideki Masaki, Tokyo (JP); Motoo Watanabe, Tokyo (JP); Irving Weissman, Stanford, CA (US)

(73) Assignees: THE UNIVERSITY OF TOKYO, Bunkyo-ku (JP); THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 628 days.

This patent is subject to a terminal disclaimer.

(21) Appl. No.: 16/857,855

(22) Filed: Apr. 24, 2020

(65) Prior Publication Data

US 2020/0315148 A1 Oct. 8, 2020

Related U.S. Application Data

(62) Division of application No. 15/873,482, filed on Jan. 17, 2018, now Pat. No. 10,645,912, which is a division of application No. 14/764,445, filed as application No. PCT/JP2014/051997 on Jan. 29, 2014, now abandoned.

(60) Provisional application No. 61/757,910, filed on Jan. 29, 2013.

(30) Foreign Application Priority Data

Nov. 19, 2013 (JP) .................................. 2013-239327

(51) Int. Cl.
*A01K 67/027* (2006.01)
*C12N 5/074* (2010.01)
*C07K 14/47* (2006.01)

(52) U.S. Cl.
CPC ...... *A01K 67/0271* (2013.01); *C07K 14/4747* (2013.01); *C12N 5/0607* (2013.01); *C12N 5/0696* (2013.01); *A01K 2207/12* (2013.01); *A01K 2227/105* (2013.01); *C12N 2501/48* (2013.01)

(58) Field of Classification Search
CPC ............ A01K 67/0271; A01K 2207/12; C07K 14/4747; C12N 5/0696
See application file for complete search history.

(56) References Cited

U.S. PATENT DOCUMENTS

| | | |
|---|---|---|
| 2007/0250943 A1 | 10/2007 | Nagao et al. |
| 2010/0122360 A1 | 5/2010 | Nakauchi et al. |
| 2011/0067125 A1 | 3/2011 | Nakauchi et al. |
| 2011/0258715 A1 | 10/2011 | Nakauchi et al. |
| 2011/0283374 A1 | 11/2011 | Nakauchi et al. |
| 2016/0257928 A1 | 9/2016 | Nakauchi et al. |

FOREIGN PATENT DOCUMENTS

| | | |
|---|---|---|
| JP | 9-500004 A | 1/1997 |
| JP | 2002-511732 A | 4/2002 |
| WO | 94/24274 A1 | 10/1994 |
| WO | 98/16630 A1 | 4/1998 |
| WO | 03/046141 A2 | 6/2003 |
| WO | 2006/009297 A1 | 1/2006 |
| WO | 2008/102602 A1 | 8/2008 |
| WO | 2009/104794 A1 | 8/2009 |
| WO | 2010/021390 A1 | 2/2010 |
| WO | 2010/087459 A1 | 8/2010 |

OTHER PUBLICATIONS

Office Action dated Jan. 31, 2017 in Japanese Patent Application No. 2014-559722.
Luc Schoonjans, et al., "Pluripotential Rabbit Embryonic Stem (ES) Cells Are Capable of Forming Overt Coat Color Chimeras Following Injection Into Blastocysts" Molecular Reproduction and Development, vol. 45, No. 4, 1996, pp. 439-443.
Daylon James, et al., "Contribution of human embryonic stem cells to mouse blastocysts" Developmental Biology, vol. 295, No. 1, 2006, pp. 90-102 with cover pages.
Kumari—"States of Pluripotency: Naïve and Primed Pluripotent Stem Cells", Pluripotent Stem Cells—From the Bench to the Clinic, pp. 31-45 (2016).
Hirabayashi, et al., "Establishment of Rat Embryonic Stem Cell Lines That Can Participate in Germline Chimerae at High Efficiency" Mol. Reprod. Dev., vol. 77, No. 94, 2009, 1 Page.
Masaki, et al., "Inhibition of Apoptosis Overcomes Stage-Related Compatibility Barriers to Chimera Formation in Mouse Embryos" Cell Stem Cell, vol. 19, Nov. 3, 2016, pp. 587-592.
Fink et al.—"Apoptosis, Pyroptosis, and Necrosis: Mechanistic Description of Dead and Dying Eukaryotic Cells", Infection and Immunity, vol. 73, No. 4, Apr. 2005, pp. 1907-1916
Weinberger et al.—"Dynamic stem cell states: naive to primed pluripotency in rodents and humans", Nature Reviews, Molecular Cell Biology, vol. 17, Mar. 2016, pp. 155-169.
Reed—"Bcl-2 and the Regulation of Programmed Cell Death", Mini-Review: Cellular Mechanisms of Disease Series The Journal of Cell Biology, vol. 124, No. 1 and 2, Jan. 1994, pp. 1-6.

(Continued)

*Primary Examiner* — Valarie E Bertoglio
(74) *Attorney, Agent, or Firm* — Oblon, McClelland, Maier & Neustadt, L.L.P.

(57) ABSTRACT

The present invention provides a method for producing a chimeric animal using a primed pluripotent stem cell, a tissue stem cell, a progenitor cell, a somatic cell, or a germ cell. The method for producing a chimeric animal according to the present invention comprises introducing a mammal-derived cell into the embryo of a mammal, the cell being primed pluripotent stem cell, tissue stem cell, progenitor cell, somatic cell, or germ cell.

4 Claims, 38 Drawing Sheets

Specification includes a Sequence Listing.

(56) References Cited

OTHER PUBLICATIONS

Nichols et al.—"Naïve and Primed Pluirpotent States", Cell Stem Cell 4, Jun. 5, 2019, pp. 487-492.
Oberoi-Khanuja et al.—"IAPs on the move: role of inhibitors of apoptosis proteins in cell migration", Cell Death and Disease (2013) 4, pp. 1-9.
Extended European Search Report dated Oct. 10, 2016 in Patent Application No. 14746871.4.
Friedrich Harder et al., "Erythroid-like Cells From Neural Stem Cells Injected Into Blastocysts", Experimental Hematology, XP002356625, vol. 32, No. 7, Jul. 2004, pp. 673-682.
Siqin Bao et al., "Epigenetic Reversion of Postimplantation Epiblast Cells to Pluripotent Embryonic Stem Cells", Nature,XP055305951, vol. 461, No. 7268, Oct. 8, 2009, 13 pages.
Albrecht M. Müller et al., "Chimerism in Embryos and Adults Following the Injection of Mouse and Human Hematopoietic and Mouse Neural Stem Cells Into Mouse Blastocysts", XP009040501, vol. 96, No. 11, part 1, Dec. 1, 2000, p. 276a.
Hideyuki Murayama et al., "Successful Reprogramming of Epiblast Stem Cells by Blocking Nuclear Localization of β-Catenin", Stem Cell Reports, XP055303963, vol. 4, No. 1, Jan. 13, 2015, pp. 103-113.
Toshiyuki Yamane et al., "Enforced Bcl-2 Expression Overrides Serum and Feeder Cell Requirements for Mouse Embryonic Stem Cell Self-Renewal", Proceedings of the National Academy of Sciences, XP055305834, vol. 102, No. 9, Mar. 1, 2005, pp. 3312-3317.
Hideki Masaki et al., "Interspecific in vitro Assay forthe Chimera-Forming Ability of Human Pluripotent Stem Cells", Development, XP055303851, vol. 142, No. 18, May 28, 2015, pp. 3222-3230.
Masahito Tachibana, et al., "Generation of Chimeric Rhesus Monkeys" Cell, vol. 148, No. 1-2, Jan. 20, 2012, pp. 285-295 with cover pages.
Calvin Simerly, et al., "Interspecies chimera between primate embryonic stem cells and mouse embryos: Monkey ESCs engraft into mouse embryos, but not post-implantation fetuses"Stem Cell Research, vol. 7, No. 1, 2011, pp. 28-40 with cover pages.
International Search Report dated Apr. 22, 2014 in PCT/JP2014/051997
Han D.W. et al.,"Epiblast Stem Cell Subpopulations Represent Mouse Embryos of Distinct Pregastrulation Stages", Cell, vol. 143, No. 4, Nov. 12, 2010, pp. 617-627.
Huang Y. et al., "In Vivo Differentiation Potential Of Epiblast Stem Cells Revealed By Chimeric Embryo Formation", Cell Rep., vol. 2, No. 6, Dec. 27, 2012, pp. 1571-1578.
Kobayashi T. et. al., "Generation of Rat Pancreas in Mouse by Interspecific Blastocyst Injection of Pluripotent Stem Cells", Cell, vol. 142, No. 5, Sep. 3, 2010, pp. 787-799.
Usui J. et. al., "Generation of Kidney From Pluripotent Stem Cells via Blastocyst Complementation", Am. J. Pathol., 2012, vol. 180, No. 6, pp. 2417-2426.
Hitomi Matsunari et al., "Regeneration of Pluripotent Stem Cell-Derived Pancreas of a Pig Using a Mechanism of Embryo Development: Proving the Principle of Blastocyst Complementation in Pigs", Nippon Saisei Iryo Gakkaishi, 2011, vol. 10, Suppl., p. 185.
Toshihiro Kobayashi et al., "Technology for Generating Interspecific Chimeras and their Application to Organ Regeneration", Cell technology, 2012, vol. 31, No. 3, 19 pages (with English Translation).
Toshihiro Kobayashi et al., "Generation of Organs Derived From Pluripotent Stem Cells Toward the Next Generation of Regenerative Medicine", Endocrinology, Diabetology & Metabolism, 2012, vol. 35, No. 2, 18 pages (with English Translation).
Ardehali R. et.al., "Overexpression of BCL2 Enhances Survival of Human Embryonic Stem Cells During Stress and Obviates the Requirement for Serum Factors", Proc. Natl. Acad. Sci. USA, 2011, vol. 108, No. 8, pp. 3282-3287.
Bai H. et al., "Bcl-xL Enhances Single-Cell Survival and Expansion of Human Embryonic Stem Cells without Affecting Self-Renewal," Stem Cell Res., 2012, vol. 8, No. 1, pp. 26-37.
Gabrielle M. Brons et al., "Derivation of Pluripotent Epiblast Stem Cells From Mammalian Embryos", Nature, vol. 448, Jul. 12, 2007, 6 pages.
Paul J. Tesar et al., "New Cell Lines From Mouse Epiblast Share Defining Features with Human Embryonic Stem Cells", Nature, vol. 448, Jul. 12, 2007, 7 pages.
Zhao et al., "Two SLipporting Factors Greatly Improve the Efficiency of HL1man iPSC Generation", Cell Stem Cell 3, Nov. 6, 2008, pp. 475-479.
Kurosawa, "Application of Rho-associated protein kinase (ROCK) inhibitor to human pluripotent stem cells", Journal of Bioscience and Bioengineering, vol. 114, No. 6. pp. 577-581, 2012.
Wakui et al., "Method for evaluation of human induced pluripotent stem cell quality using image analysis based on the biological morphology of cells", Journal of Medical Imaging, 2017, pp. 1-10.
Abercrombie, "The cells Fibroblasts", J. Clin. Path., 1978, pp. 1-6.
Warrier et al., "Direct comparison of distinct naive pluripotent states in human embryonic stem cells", Nature Communications, 2017, pp. 1-10.
Thomson et al., "Embryonic Stem Cell Lines Derived from Human Blastocysts", Science, vol. 282, 1998, pp. 1145-1147.
Reubinoff et al., "Embryonic stem cell lines from human blastocysts: somatic differentiation in vitro", Nature Biotechnology, vol. 18, 2000, pp. 399-404.
Reijo et al., "Gene expression profiles of human inner cell mass cells and embryonic stem cells", Differentiation, vol. 78, 2009, pp. 18-23.
Lai et al., "SRY (sex determining region Y)-box2 (Sox2)/poly ADP-ribose polymerase 1 (Parp 1) complexes regulate pluripotency", Proc Natl Acad Sci USA, vol. 109, 2012, pp. 3772-3777.
Dominiquez-Bendala et al., "Islet Cell Therapy and Pancreatic Stem Cells", Handbook of Stem Cells, Chapter 70, 2013, pp. 835-853.
UK House of Parliaments, "Government proposals for the regulation of hybrid and chimera embryos", Science and Technology Committee, Fifth Report of Session 2006-07, vol. II, 2007, pp. 76-77.
Office Action dated Apr. 4, 2018 issued in corresponding European patent application No. 14 746 871.4.
Andrew T. Crane, et al. "The American Public Is Ready to Accept Human-Animal Chimera Research" Stem Cell Reports, vol. 15, Oct. 13, 2020, pp. 1-7.

Bright field

TdTomato

Bright field

TdTomato

Bright field

TdTomato

7 Div

Fig. 15A
Fig. 15B
Control
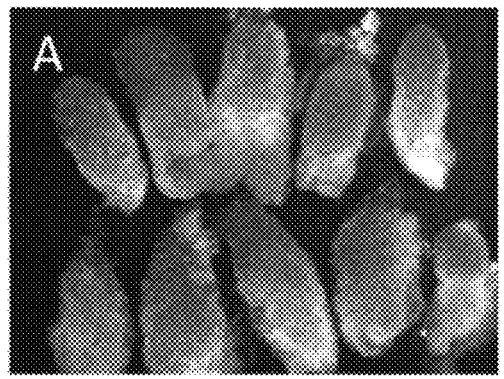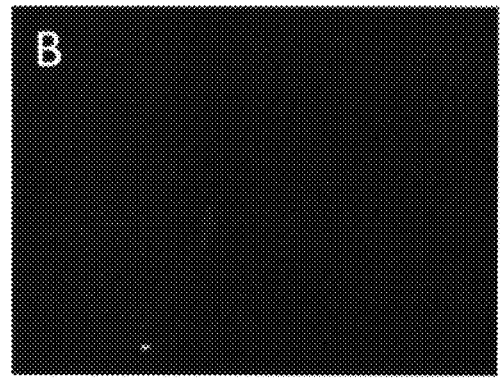
Fig. 15C
Fig. 15D
BCL2 (+)
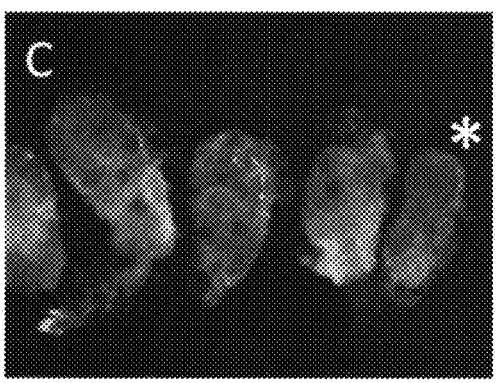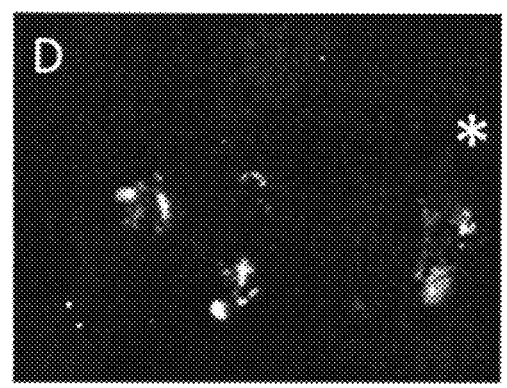
Fig. 15E
Fig. 15F
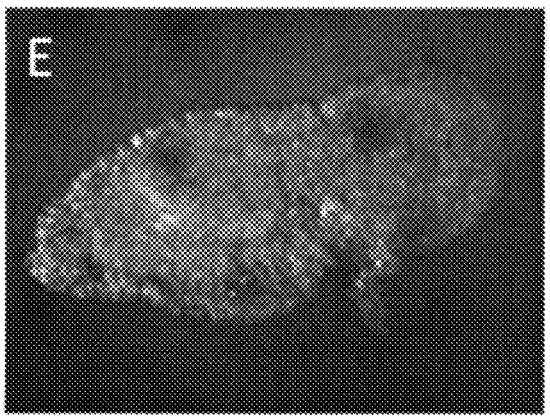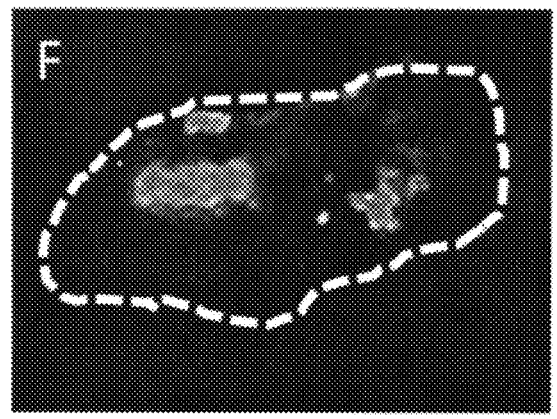

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
```

```
<223> OTHER INFORMATION: Synthetic primer

<400> SEQUENCE: 1
cagcttcttt gcagctcctt                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic primer

<400> SEQUENCE: 2
cttctccatg tcgtcccagt                                              20

<210> SEQ ID NO 3
<211> LENGTH: 20
<212> TYPE: DNA
<213> ORGANISM: Artificial Sequence
<220> FEATURE:
<223> OTHER INFORMATION: Synthetic primer

<400> SEQUENCE: 3
ggcatcctga ccctgaagta                                              20

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
agaggcgtac aaggaaagca                                              20
```

METHOD FOR PRODUCING CHIMERIC ANIMAL

CROSS-REFERENCE TO RELATED APPLICATIONS

The present application is a divisional of and claims the benefit of priority to U.S. application Ser. No. 15/873,482 (filing date: Jan. 17, 2018), now U.S. Pat. No. 10,645,912, which is a divisional of and claims the benefit of priority to U.S. application Ser. No. 14/764,445 (filing date: Jul. 29, 2015), now abandoned, which is the National Stage of the International Patent Application No. PCT/JP2014/051997 (filing date: Jan. 29, 2014), which claims the priority to U.S. Provisional Patent Application No. 61/757,910 (filing date: Jan. 29, 2013) and earlier Japanese Patent Application No. 2013-239327 (filing date: Nov. 19, 2013). The contents of all of the above applications are entirely incorporated herein by reference.

STATEMENT OF ACKNOWLEDGEMENT

This invention was made with Government support under contracts HL058770 and HL086065 awarded by the National Institutes of Health. The Government has certain rights in this invention.

TECHNICAL FIELD

The present invention relates to a method for producing a chimeric animal using a primed pluripotent stem cell (e.g., a pluripotent stem cell obtained from an embryo at an epiblast or later developmental stage), a tissue stem cell, a progenitor cell, a somatic cell, or a germ cell.

BACKGROUND ART

Pluripotent stem cells obtained from the inner cell mass (ICM) of a blastocyst are known to have high ability to form a chimera. However, pluripotent stem cells obtained from an embryo at a more advanced developmental stage (e.g., an epiblast or later embryo) have been considered to be inferior in the ability to form a chimera (Non Patent Literatures 1 to 3).

CITATION LIST

Non Patent Literature

Non Patent Literature 1: Brons et al., Nature (2007), 448 (7150): 191-195
Non Patent Literature 2: Tesar et al., Nature (2007), 448 (7150): 196-199
Non Patent Literature 3: Han et al., Cell (2010), 143: 617-627

SUMMARY OF INVENTION

The present invention provides a method for producing a chimeric animal using a primed pluripotent stem cell, a tissue stem cell, a progenitor cell, a somatic cell, or a germ cell.

The present inventors have found that a mammalian cell, for example, a primed pluripotent stem cell (e.g., a pluripotent stem cell at an epiblast or later developmental stage), a tissue stem cell, a progenitor cell, a somatic cell, or a germ cell, which has heretofore been considered to have no ability to form a chimera, can be used as a cell to be introduced into an embryo for the production of a chimeric animal. The present inventors have also found that the cell to be introduced in to an embryo has the improved rate of chimera formation when having been subjected to cell death suppression treatment (e.g., apoptosis suppression treatment). The present invention is based on these findings.

Specifically, the present invention provides the following aspects:

(1) A method for producing a chimeric animal, comprising
introducing a mammal-derived cell to the embryo of a mammal, wherein the cell is a primed pluripotent stem cell, tissue stem cell, progenitor cell, somatic cell, or germ cell.
(2) The method according to (1), wherein the cell to be introduced to the embryo has been subjected to cell death suppression treatment.
(3) The method according to (1) or (2), wherein the cell to be introduced to the embryo is a lineage-committed progenitor cell.
(4) The method according to (3), wherein the cell to be introduced to the embryo is an endodermal lineage progenitor cell.
(5) The method according to (4), wherein the cell to be introduced to the embryo is a Sox17-expressing cell.
(6) The method according to any of (1) to (5), wherein the cell to be introduced to the embryo is a pluripotent stem cell capable of forming a colony after being a dispersed single cell.
(7) A method for producing a chimeric animal, comprising
introducing a human pluripotent stem cell to the embryo of a mammal, wherein
the cell has been subjected to cell death suppression treatment.
(8) A method for improving the ability of a mammal-derived cell to form a chimera, comprising
subjecting the cell to cell death suppression treatment,
wherein the cell is a primed pluripotent stem cell, tissue stem cell, progenitor cell, somatic cell, or germ cell.
(9) A cell obtained by a method according to (8).
(10) A method for evaluating the differentiation potential of a cell or the in vivo function or safety of a cell, comprising
producing a chimeric animal by a method according to any of (1) to (5) (provided that the cell to be evaluated is used as a cell that is introduced to the embryo of a nonhuman mammal) and
examining the contribution of the cell to each tissue in the produced chimeric animal to evaluate the differentiation potential of the cell into each tissue or the in vivo function or safety of the cell.
(11) A method for rendering a primed pluripotent stem cell less differentiated, comprising
subjecting the primed pluripotent stem cell to cell death suppression treatment.
(12) An agent for use in promoting reprogramming of a primed pluripotent stem cell, comprising a cell death suppressor.
(13) A method for producing a naïve pluripotent stem cell, comprising
subjecting a primed pluripotent stem cell to cell death suppression treatment.
(14) An agent for inducing a naïve pluripotent stem cell from a primed pluripotent stem cell, comprising a cell death suppressor.

(15) A method for screening for a compound, comprising:
  contacting compounds with a cell;
  using the cell as a cell to be introduced in to an embryo to produce a chimeric animal,
  examining the distribution of the cell in the body of the chimeric animal to evaluate the ability of the cell to form a chimera and/or the differentiation potential of the cell; and
  selecting a compound that positively or negatively influences the ability of the cell to form a chimera and/or the differentiation potential of the cell, on the basis of the evaluation results.

BRIEF DESCRIPTION OF DRAWINGS

FIGS. 1K to 1P are diagrams showing the contribution of the introduced EpiSC to the germline. FIGS. 1K to 1P show that DsRed or tdT indicating EpiSC-derived cells is colocalized with a germline cell marker mouse vasa homolog (Mvh).

FIGS. 2A and 2B show microscopic images of fetuses obtained using Bcl-2-untransfected epiblast stem cells (control). FIGS. 2C and 2D show microscopic images of fetuses obtained using Bcl-2-transfected epiblast stem cells. FIG. 2E is a diagram showing the effect of forced Bcl-2 expression on the rate of chimera formation of EpiSC. The box of FIG. 2D depicts the presence of fetuses that formed chimeras.

FIGS. 4A and 4B show microscopic images of fetuses obtained using K17-5 cells untransfected with Bcl-2-encoding gene (control). FIGS. 4C and 4D show microscopic images of fetuses obtained using cells derived from K17-5 cells transfected with Bcl-2-encoding gene. The arrows of FIG. 4D depict the presence of portions that formed chimeras.

FIGS. 5B, 5E, and 5H show the localization of cells positive to an endoderm marker Foxa2. FIGS. 5C, 5F, and 5I show the localization of K17-5 cell-derived cells.

FIGS. 6B and 6D show microscopic images of fetuses which were obtained by using Bcl-xL-untransfected epiblast stem cells (control). FIGS. 6C and 6E show microscopic images of fetuses which were obtained by using Bcl-xL-transfected epiblast stem cells.

FIG. 11A shows the rate of chimera formation of epiblast stem cells (EpiSCs). FIG. 11B shows the rate of chimera formation of endodermal lineage progenitor cells. FIGS. 11C to 11F show the contribution of the endodermal lineage progenitor cells to embryos. The arrows in the drawing depict the presence of the endodermal lineage progenitor cells.

In FIG. 13B, Chimera/TE depicts the ratio of chimeras to embryos transplanted in recipients, and Chimera/Fetus depicts the ratio of chimeras to embryos obtained at the time of analysis.

FIGS. 15A to 15G are a diagram showing results of observing chimera formation after introduction of marmoset embryonic stem cells (ES cells) to mouse embryos. Bcl-2(+) represents that the cells were forced to express Bcl-2. (FIGS. 15C and 15D). Control represents that the cells did not express Bcl-2 (FIGS. 15A and 15B). FIGS. 15E and 15F are enlarged photographs of the embryos indicated by the asterisks in FIGS. 15C and 15D, respectively. FIG. 15G is an electrophoregram of PCR amplification fragments showing that the mouse embryo contained marmoset cells.

DETAILED EXPLANATION OF THE INVENTION

Figure 1A:
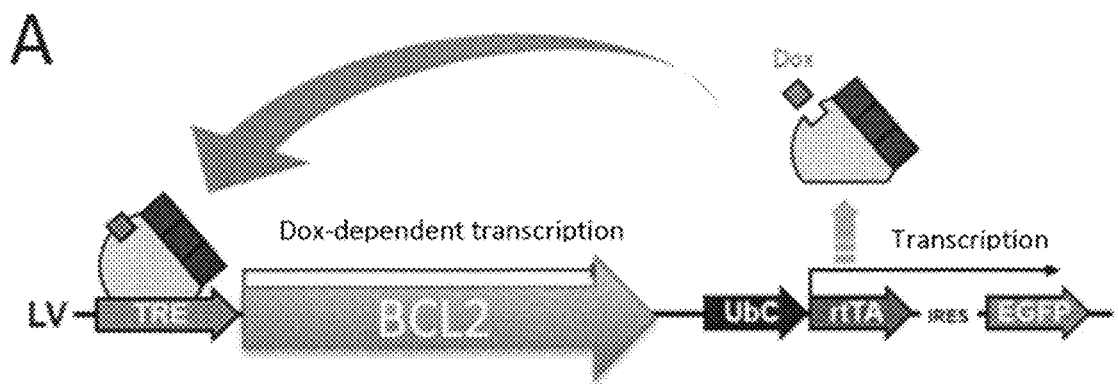
FIGS. 1A to 1P are a diagram showing the outline of a method for transfecting mouse epiblast stem cells (hereinafter, also referred to as "EpiSC") with Bcl-2-encoding gene (FIG. 1A) and a diagram showing optical microscopic images (FIGS. 1B, 1D, 1F, and 1H) and fluorescence microscopic images (FIGS. 1C, 1E, 1G, and 1I) of fetuses or a newborn obtained by introduction of the cells.

In the method of the present invention, a mammalian cell, for example, a primed pluripotent stem cell (e.g., a pluripotent stem cell at an epiblast or later developmental stage), a tissue stem cell, a progenitor cell, a somatic cell, or a germ cell, which has heretofore been considered to have no ability to form a chimera, can be used as a cell for embryonic introduction for the production of a chimeric animal.

In the method of the present invention, the cell to be introduced into an embryo is not necessarily required to undergo cell death suppression treatment (e.g., apoptosis suppression treatment). The cell to be introduced into an embryo has the improved rate of chimera formation when having been subjected to cell death suppression treatment (e.g., apoptosis suppression treatment). In the method of the present invention, the cell to be introduced into an embryo does not have to undergo cell death suppression treatment (e.g., apoptosis suppression treatment), provided that the cell is a cell death-resistant cell (e.g., an apoptosis-resistant cell). This cell can form a chimera with high efficiency.

In the present invention, the cell death suppression treatment (e.g., apoptosis suppression treatment) may be carried out before introduction of the cell into the embryo or after introduction thereof (e.g., after transplantation of the embryo obtained by the introduction of the cells into the uterus of a foster mother) or may be carried out before and after introduction of the cell into the embryo. From the viewpoint of reliably suppressing cell death (e.g., suppressing apoptosis), the cell death suppression treatment (e.g., apoptosis suppression treatment) is preferably carried out before and after introduction of the cell to the embryo.

In the method of the present invention, the cell can be introduced into a nonhuman animal embryo (e.g., a nonhuman vertebrates embryo such as an embryo of a nonhuman mammals or an embryo of birds), preferably an 8-cell, morula-stage, or blastocyst-stage embryo. In the case of introducing the cell to the 8-cell embryo or the morula-stage embryo, the cell can be introduced to, for example, near the center of the embryo. In the case of introducing the cell to the blastocyst-stage embryo, the cell can be introduced to, for example, the blastocoel. Early embryos up to the morula stage may be gathered by the contact of the cells therewith. In the method of the present invention, examples of the embryo to which the cell is to be introduced include: vertebrate-derived embryos such as nonhuman mammal-derived embryos, for example, embryos derived from nonhuman primates such as chimpanzees, gorillas, orangutans, monkeys, marmosets, and bonobos; embryos derived from nonhuman mammals such as pigs, rats, mice, cattle, sheep, goats, horses, and dogs (e.g., embryos of carnivorous animals, artiodactyls, perissodactyls, and rodents); and embryos of birds such as chickens.

In the present specification, the "cell having no ability to form a chimera" refers to a cell that forms no chimera or forms a chimera with a significantly low frequency when transplanted to a pre-implantation embryo.

In the present invention, the "pluripotent stem cell" means a stem cell having pluripotency. Examples thereof include pluripotent stem cells having pluripotency, such as embryonic stem cells (ES cells), induced pluripotent stem cells (iPS cells), and epiblast stem cells (EpiSC). The pluripotent stem cell includes, for example, a naïve pluripotent stem cell, a feature of which is to maintain its pluripotency in a manner dependent on a leukemia inhibitory factor (LIF), and a primed pluripotent stem cell (which is at a more advanced stage of differentiation than that of the naïve type and has inactivated X chromosomes), a feature of which is to maintain its pluripotency in a manner dependent on fibroblast growth factor 2 (Fgf2) and activin. Rodent ES cells and iPS cells are classified into the naïve pluripotent stem cell. Rodent epiblast stem cells and some non-rodent ES cells and iPS cells are classified into the primed pluripotent stem cell. The primed pluripotent stem cell and the naïve pluripotent stem cell differ in many points. For example, in colony morphology, the primed pluripotent stem cell mainly forms a single-layer flat colony, whereas the naïve pluripotent stem cell mainly forms a multi-layer colony. In addition, as specific marker genes, Brachyury and Fgf5 are known for the primed pluripotent stem cell, while CD31, Rex1, Klf4, and NrOb1 are known for the naïve pluripotent stem cell. In this way, the primed pluripotent stem cell and the naïve pluripotent stem cell differ in biochemical and physiological features. Those skilled in the art should readily obtain the primed pluripotent stem cell and identify the primed pluripotent stem cell on the basis of the aforementioned properties, etc.

In the present invention, the "epiblast stem cell" refers to a cell line established from the late epiblast of a post-implantation embryo, or a cell line that is a cell obtained from a pre-implantation embryo and has reached a stage of differentiation corresponding to the epiblast stem cell. The epiblast stem cell can be cultured in the presence of basic fibroblast growth factor (bFGF) and activin A and exhibits the physiological feature that the cell forms a large single-layer colony by adherent culture, and the further feature that one of the two X chromosomes is inactivated in female cells. These features are similar to the features exhibited by primed ES cells or iPS cells.

In the present invention, the "primed pluripotent stem cell" means a primed pluripotent stem cell such as a primed ES cell or iPS cell. In the present invention, examples of the "pluripotent stem cell" can include, but are not particularly limited to, pluripotent stem cells of primates such as humans and monkeys, and pluripotent stem cells of mammals such as pigs, cattle, sheep, and goats. In the present invention, the pluripotent stem cell is preferably a human pluripotent stem cell. The primed pluripotent stem cell is inferior in the ability to form a chimera to the naïve pluripotent stem cell.

In the present invention, in the case of using the primed pluripotent stem cell as the cell to be introduced into an embryo, a cell death-resistant cell (i.e., a pluripotent stem cell insusceptible to cell death, for example, apoptosis-resistant pluripotent stem cell (i.e., a pluripotent stem cell having low apoptotic capacity)) is preferably used. In the present invention, the cell death-resistant cell (e.g., apoptosis-resistant cell) may be obtained by, for example, screening. The cell death-resistant primed pluripotent stem cell (e.g., apoptosis-resistant primed pluripotent stem cell) can be used as the cell to be introduced into an embryo in the formation of a chimeric animal without additional cell death suppression treatment (e.g., apoptosis suppression treatment). In the present invention, in the case of using the primed pluripotent stem cell as the cell to be introduced into an embryo, for example, a primed pluripotent stem cell capable of forming a colony by adherent culture after being a dispersed single cell can also be used. In the present invention, the rate of colony formation after dispersion of a cell cluster into a single cell is preferably 20% or more, more preferably 40% or more, further preferably 60% or more.

Thus, a primed pluripotent stem cell having preferably 20% or more, more preferably 40% or more, further preferably 60% or more rate of colony formation after dispersion of a cell cluster into a single cell may be used as the cell to be introduced into an embryo. In the present invention, the primed pluripotent stem cell capable of forming a colony after being a dispersed single cell can be screened for using colony formation after dispersion of a cell cluster into a single cell and/or a high rate of the formation (e.g., preferably 20% or more, more preferably 40% or more, further preferably 60% or more rate of the formation) as indexes. The cell death resistance of the pluripotent stem cell is associated with its ability to form a colony. Thus, the cell death-resistant cell can be obtained by screening using colony formation after dispersion of a cell cluster into a single cell and/or a high rate of the formation (e.g., preferably 20% or more, more preferably 40% or more, further preferably 60% or more rate of the formation) as indexes. For examining the colony formation, the cell can be cultured under the same conditions as the culture conditions of ordinary adherent culture.

The apoptosis resistance of the cell other than the pluripotent stem cell can be verified by culture in the presence of an apoptosis inducer such as actinomycin D and can be used as, for example, an index for the screening of an apoptosis-resistant cell.

The cell death (e.g., necrosis) resistance of the cell other than the pluripotent stem cell can be verified by culture with a necrosis inducer (e.g., induction of active oxygen such as $H_2O_2$) and a nutrient-poor medium and can be used as, for example, an index for the screening of a cell death-resistant cell.

In the present invention, the "tissue stem cell" refers to a cell that lacks pluripotency, but still has the ability to self-replicate while maintaining its ability to differentiate into plural types of cells. This cell is also called somatic stem cell or adult stem cell. Ectodermal lineage stem cells, mesodermal lineage stem cells, and endodermal lineage stem cells are known as the tissue stem cell. Examples of the ectodermal lineage stem cells include neural stem cells. The neural stem cells can be obtained by a method well known to those skilled in the art, for example, a method described in Kukekov et al., Glia 21: 399-407, 1997. The neural stem cells can be obtained without particular limitations, for example, by the culture of a cell group isolated from the forebrain of an embryo or the subventricular zone of an individual after birth using, for example, a commercially available basal medium for neural progenitor cells. Whether or not the obtained cells are neural stem cells can be examined on the basis of the presence or absence of the expression of specific a marker gene, for example, the expression of nestin.

In the present invention, the "progenitor cell" refers to an undifferentiated parent cell that does not exhibit a particular differentiation character that is exhibited by its offspring cells. Unlike the tissue stem cell, the progenitor cell lacks the ability to self-replicate. The conversion of a stem cell into a progenitor cell of a particular differentiated cell refers to determination or commitment in cell differentiation.

In the present invention, the "lineage-committed progenitor cell" refers to a progenitor cell whose differentiation fate into an ectodermal lineage, a mesodermal lineage, or an endodermal lineage has been established. The ectodermal lineage-committed progenitor cell (ectodermal lineage progenitor cell) is a progenitor cell of an ectodermally derived cell, and examples thereof include neural progenitor cells. The mesodermal lineage-committed progenitor cell (mesodermal lineage progenitor cell) is a progenitor cell of a mesodermally derived cell, and examples thereof include hematopoietic stem/progenitor cells and vascular endothelial progenitor cells. The endodermal lineage-committed progenitor cell (endodermal lineage progenitor cell) is a progenitor cell of an endodermally derived cell, and examples thereof include Sox17-expressing endodermal lineage progenitor cells. Examples of the lineage-committed progenitor cell of a germ cell include primordial germ cells. These lineage-committed progenitor cells do not differentiate into cells of a lineage other than the determined lineage at a later developmental stage. For example, once differentiation fate into an endodermal lineage is established, the cell does not differentiate into a cell other than the endodermally derived cell in vivo unless reprogrammed or dedifferentiated. In the present invention, the introduction of the lineage-committed progenitor cell causes the introduced progenitor cell to differentiate according to the determined fate, and the resulting cell therefore makes no contribution to a tissue or an organ of a lineage other than the determined lineage. One of the advantages of the introduction of the lineage-committed progenitor cell to an embryo is that use of the lineage-committed progenitor cell permits production of a chimeric animal with reduced contribution to undesired organs (e.g., the brain, nerves, and germlines). In the present invention, examples of the lineage-committed progenitor cell include lineage-committed progenitor cells derived from primates such as humans and monkeys; mammals such as pigs, cattle, sheep, and goats; and rodents such as mice and rats.

The ectodermal lineage progenitor cell can be obtained by, for example, a method well known to those skilled in the art. For example, the neural progenitor cell can be obtained without particular limitations by the isolation of neurospheres from the cerebral cortex followed by culture using, for example, a commercially available basal medium for neural progenitor cells. Whether or not the obtained cell is an ectodermal lineage progenitor cell can be examined on the basis of the presence or absence of the expression of an ectoderm marker, for example, the expression of Pax6 and/or Olig2.

Examples of the mesodermal lineage stem cell or the mesodermal lineage progenitor cell include hematopoietic stem/progenitor cells. The hematopoietic stem/progenitor cells can be selected by a method well known to those skilled in the art, and can be selected without particular limitations, for example, as a cell stained with an antibody against CD150 without being stained with antibodies against Gr-1, Mac-1, Ter119, CD4, CD8, B220, IL-7R, CD41, and CD48 using FACS which involves the antibody staining of blood cells in the mouse adult bone marrow or the fetal liver.

The endodermal lineage progenitor cell can be obtained by, for example, a method well known to those skilled in the art, for example, the culture of ES cells in the presence of activin A (e.g., 10 μg/mL). Whether or not the obtained cell is an endodermal lineage progenitor cell can be examined on the basis of the presence or absence of the expression of an endoderm marker, for example, but is not particularly limited to, the expression of Sox17, Eomes, Gata4, and/or Foxa2.

In the present invention, the "somatic cell" refers to every cell except for a germ cell.

In the present invention, the "germ cell" refers to a haploid cell specialized to be responsible for reproduction, and its mother cell and primordial germ cell. Specific examples of the germ cell include sperms and ova, and their mother cells and primordial germ cells. The primordial germ cells are known to be obtained without particular limitations, for example, by a method which involves isolation from the gonad of an embryo or a method which involves the induction of differentiation from ES cells, iPS cells, or other pluripotent stem cells. For example, mouse primordial germ cells can be isolated without particular limitations, for example, by the dissociation of harvested gonad in a trypsin solution or the like followed by selection as cells stained with both antibodies against SSEA1 and CD61 by FACS or the like. For example, the mouse primordial germ cells can be obtained without particular limitations, for example, by differentiation from mouse ES cells according to a method reported by Hayashi et al. (Hayashi et al., Cell (2012), 146 (4) 519-532). Whether or not the obtained cells are primordial germ cells can be examined on the basis of the presence or absence of the expression of a specific marker, for example, but is not limited to, the expression of Blimp1 and/or Stella.

In the present invention, the relationship between the embryo and the cell to be introduced to the embryo may be the same species or may be different species (e.g., WO2010/087459, which is incorporated herein by reference). In the present invention, examples of the combination of the species of the embryo and the cell to be introduced to the embryo include the combination of a mouse and a rat. Mouse-rat chimeric animals have successfully been produced by blastocyst complementation (WO2010/021390 and WO2010/087459, which are incorporated herein by reference). The mouse-rat genetic distance corresponds to a human-pig genetic distance. Thus, the successful production of such mouse-rat interspecific chimeric animals means that interspecific chimeric animals between species having a closer genetic distance can be sufficiently produced.

According to Examples 4B and 4C of the present application, chimeric animals were successfully produced between a mouse and a human or between a mouse and a marmoset. Thus, even if a rodent and a primate are combined, a chimeric animal can be formed. Furthermore, an interspecific chimeric animal can be produced between species presumably having a difference smaller than the difference between a rodent and a primate. From these viewpoints, examples of the interspecific combination of the embryo and the cell to be introduced to the embryo that may be used in the present invention can include, in addition to the mouse-rat combination, combination between nonhuman mammals, combination between birds, combination between a human and a nonhuman primate animal, combination between a human and a chicken, combination between a human and a pig, combination between a human and cattle, combination between a human and a goat, combination between a human and sheep, combination between nonhuman primate animals, combination between a nonhuman primate animal and a pig, cattle, or sheep, combination between cattle and a pig, sheep, a goat, or a horse, and combination between a pig and sheep, a goat, or a horse. Alternatively, a human may be combined with an animal belonging to any of carnivorous animals, artiodactyls, and perissodactyls, or animals belonging to the same genus, category, or family may be combined with each other. Although a mouse and a rat differ in the number of chromosomes, mouse-rat chimeric animals can be produced. Thus, the possibility of producing a chimeric animal even between animals differing in the number of chromosomes is not denied.

The cell death means the death of a living cell. The cell death is broadly classified into programmed cell death (apoptosis), autophagy, and necrosis.

The compound having a cell death-suppressing effect means every compound capable of suppressing cell death, and examples thereof include cell death inhibitors. Examples of the cell death inhibitor used in the present invention include apoptosis inhibitors, autophagy inhibitors, and necrosis inhibitors. These inhibitors can be appropriately used for suppressing cell death.

The apoptosis inhibitor used in the present invention is not particularly limited as long as the apoptosis inhibitor is capable of suppressing cell apoptosis. Examples thereof include caspase inhibitors and inhibitors of pro-apoptotic factors of the Bcl-2 family. Various apoptosis inhibitors are commercially available and can be appropriately used for suppressing cell apoptosis.

Examples of the autophagy inhibitor used in the present invention include PI3K inhibitors, p38 inhibitors, ERK inhibitors, and JNK inhibitors. The autophagy inhibitor can be used for suppressing cell autophagy.

Examples of the necrosis inhibitor used in the present invention include RIP1 to RIP3 inhibitors (RIP: receptor-interacting protein) such as necrostatin-1 and active oxygen inhibitors such as 2-(1H-indol-3-yl)-3-pentylaminomaleimide (IM-54). The necrosis inhibitor can be used for suppressing cell necrosis or necroptosis.

Examples of the anti-apoptotic factor targeted by the induction of expression according to the present invention include, but are not particularly limited to, FLIP, Mcl-1, Xiap, crmA, Bcl-2, and Bcl-xL. Xiap, crmA, Bcl-2, or Bcl-xL can be preferably used in the invention. A possible approach for inducing the expression of these factors is a direct approach, for example, but is not particularly limited to, the transfer of target gene expression vectors to cells, the transfer of mRNA, proteins, or functional fragments thereof to cytoplasms, or the induction of the expression of the target factors via noncoding RNA such as miRNA. Another possible approach for inducing the expression of these factors is an indirect approach, for example, but is not particularly limited to, the induction of the expression by a method such as the transfer of expression vectors for enhancing the expression of a factor (which indirectly brings about an anti-apoptotic effect) enhancing the expression level and/or activity of an apoptosis-suppressing factor or an anti-apoptotic factor agonist to cells, the transfer of mRNA, proteins, or functional fragments thereof to cytoplasms, or the induction of the expression via noncoding RNA such as miRNA. The induction of expression is preferably transient in consideration of its influence on the malignant transformation of cells, etc. Also, a method that rarely damages the genomes of cells is preferably adopted. Various methods such as a method using adenovirus vectors and a method using plasmids can be used for the purpose of achieving the transient induction of expression and preventing damages on the genomes of cells. The term "functional fragment" as used herein means a fragment that maintains anti-apoptotic functions. The aforementioned anti-apoptotic factors and the approaches for inducing their expression can be used as apoptosis suppressors. In the present specification, both human BCL2 and mouse Bcl2 are referred to as "Bcl-2", irrespective of species, for the sake of convenience of description.

Examples of the apoptotic factor targeted by the suppression of expression according to the present invention include Smac/Diablo, apoptosis-inducing factor (AIF), HtrA2, Bad, Bim, Bax, p53, caspases 1, 2, 3, 4, 5, 6, 7, 8, 9, and 10 (e.g., caspases 2, 3, 6, 7, 8, 9, and 10, preferably caspases 3, 6, and 7), Fas ligand (FasL), tumor necrosis factor-related apoptosis-inducing ligand (TRAIL), and FoxO1. The suppression of expression can be carried out by a direct approach, for example, but is not particularly limited to, a method well known to those skilled in the art, such as the suppression of the expression of the target factors via noncoding RNA such as siRNA, shRNA, or miRNA. The suppression of expression may also be increased by an indirect approach, for example, but is not particularly limited to, a method such as the suppression of the expression of the target factors via noncoding RNA such as miRNA in order to reduce the expression and/or activity of a factor (which indirectly brings about an apoptotic effect) enhancing the expression level and/or activity of an apoptosis-promoting factor. Alternatively, a method for suppressing apoptosis using an apoptosis-promoting factor antagonist is also possible. The aforementioned apoptotic factors and the approaches for suppressing their expression can be used as apoptosis suppressors.

The siRNA refers to double-stranded RNA (nucleic acid) consisting of, but is not particularly limited to, 20 to 30-bp, for example, 21-bp, 22-bp, 23-bp, 25-bp, or 27-bp double-stranded RNA that can induce RNA interference (RNAi) and has a sequence homologous to the sequence of a target gene. Those skilled in the art can design and produce such double-stranded RNA on the basis of the gene sequence of the target gene to be knocked down using a well-known method. The siRNA may be in the form of a hybrid with DNA or RNA. For example, "U" in the siRNA may be replaced with "T".

The shRNA refers to RNA that can form siRNA upon degradation by Dicer in vivo. The shRNA has a stem-loop structure containing a double-stranded stem and a hairpin loop. This hairpin loop moiety is not particularly limited by its sequence and can have a 5- to 12-base sequence (Kawasaki H. et al., Nucleic Acid Res. (2003) 31: 700-707; Paddison P. J. et al., Genes and Dev. (2002) 16: 948-958; Lee N. S., Nat. Biotech. (2002) 20: 500-505; and Sui G., Proc. Natl. Acad. Sci. U.S.A (2002) 99: 5515-5520). Such shRNA can be designed and produced on the basis of the gene sequence of the target gene to be knocked down by a method well known to those skilled in the art.

In the present invention, a chimeric animal can be produced with high efficiency using a primed pluripotent stem cell, a tissue stem cell, a progenitor cell, a somatic cell, or a germ cell as a cell to be introduced into an embryo by suppressing the cell death (e.g., apoptosis) of the cell.

The method of the present invention may further comprise developing the embryo obtained by the introduction of the cell in the womb of a nonhuman foster mother animal to obtain a fetus or a newborn. The production of a chimeric mammal generally comprises: introducing a mammal cell having the ability to form a chimera, such as an ES cell, to the embryo of a mammal; transplanting the obtained embryo into the uterus of a foster mother animal; and obtaining a newborn of a chimera from the foster mother animal. In the present invention, the nonhuman foster mother animal can be the same species as that of the embryo to which the cell is to be introduced.

The present invention is useful because the primed pluripotent stem cell, the tissue stem cell, the progenitor cell, the somatic cell, or the germ cell that has been subjected to cell death suppression treatment (e.g., apoptosis suppression treatment) allows higher efficiency of production of a chimeric animal.

The production of a genetically modified animal requires a pluripotent stem cell having high ability to form a chimera. The present invention provides a primed pluripotent stem cell, a tissue stem cell, a progenitor cell, a somatic cell, or a germ cell having high ability to form a chimera. Thus, the present invention provides, for example, a method for producing a nonhuman genetically modified animal, comprising subjecting a primed pluripotent stem cell, a tissue stem cell, a progenitor cell, or a germ cell (in this context, each of the tissue stem cell and the progenitor cell is a cell capable of differentiating into a germ cell) to cell death suppression treatment (e.g., apoptosis suppression treatment). In the method for producing a genetically modified animal according to the present invention, a genetically modified cell can be used as a cell to be introduced to the embryo for the method for producing a chimeric animal according to the present invention.

For example, a method for producing a genetically modified animal such as a knockout mouse or a transgenic mouse is well known as the method for producing a genetically modified animal. For the genetically modified animal, a genetically modified pluripotent stem cell (e.g., a genetically modified ES cell) is introduced to the blastocoel of a blastocyst, which is then transplanted into the uterus of a foster mother to obtain a chimeric animal newborn. In the case of obtaining a knockout animal, in general, the chimeric animal thus obtained may be mated with a wild-type animal, and a genetically modified newborn having a heterozygous genome is further obtained from the chimeric animal, or the heterozygous newborns thus obtained may be further crossed with each other to obtain a genetically modified newborn having a homozygous genome. In the method of the present invention as well, a primed pluripotent stem cell, a tissue stem cell, a progenitor cell, or a germ cell (in this context, each of the tissue stem cell and the progenitor cell is a cell capable of differentiating into a germ cell) is genetically modified, and the obtained genetically modified cell is introduced to the embryo (8-cell, morula-stage, or blastocyst-stage embryo) of a nonhuman animal (e.g., a vertebrate such as a non-rodent nonhuman mammal or a bird), which can then be returned to the uterus of a foster mother to produce a chimeric animal. In the chimeric animal, the introduced primed pluripotent stem cell contributed to the germline. Hence, according to the present invention, a genetically modified animal can be obtained using a primed pluripotent stem cell as the cell for embryonic introduction in a non-rodent mammal. In the production of the genetically modified animal, preferably, the relationship between the cell to be introduced and the embryo is the same species. The obtained genetically modified cell can be subjected to cell death suppression treatment (e.g., apoptosis suppression treatment) before and/or after introduction to the embryo. In the present invention, the lineage-committed progenitor cell was shown to be able to contribute to a chimeric animal according to the original prospective fate, regardless of the presence or absence of cell death suppression treatment (e.g., apoptosis suppression treatment). Also, the cell death suppression treatment (e.g., apoptosis suppression treatment) of the lineage-committed progenitor cell drastically improved the rate of chimera formation. This principle can be applied to a primordial germ cell or a germline cell arising from a primordial germ cell to efficiently produce a genetically modified animal. More specifically, a primordial germ cell (germ cell) induced from a pluripotent stem cell or a primordial germ cell (germ cell) collected from an embryo is genetically modified, and the obtained cell can be subjected to cell death suppression treatment (e.g., apoptosis suppression treatment) and then transplanted into an embryo to efficiently obtain a germ cell derived from the genetically modified cell. If a germ cell-deficient variant is used as the embryo to receive the transplantation, a germ cell derived from the genetically modified cell is obtained further efficiently. In birds typified by chickens, the cell for embryonic introduction is known to rarely contribute to the germline, though a chimeric animal can be produced by pluripotent stem cell transplantation. The method of the present invention is particularly advantageous for the production of genetically modified animals of birds.

The cell having the ability to form a chimera can be used in organ regeneration by use of blastocyst complementation (WO2008/102602 and WO2010/021390, which are incorporated herein by reference). Hence, the present invention provides a method for producing an organ of interest, comprising the steps of: a) preparing a primed pluripotent stem cell, a tissue stem cell, a progenitor cell, a somatic cell, or a germ cell; b) transplanting the cell into a fertilized egg at a blastocyst stage of a nonhuman mammal; c) developing the fertilized egg in the womb of a nonhuman foster mother mammal to obtain a newborn; and d) obtaining the organ of interest from the newborn individual, wherein the nonhuman mammal is a nonhuman mammal having an abnormality by which the development of the organ to be produced does not occur at a developmental stage. In this context, the cell and the organ to be produced can be derived from a mammal individual different from the nonhuman mammal individual. In one embodiment of the present invention, the embryo to which the cell is to be introduced is the embryo of a nonhuman animal (e.g., a nonhuman mammal or a vertebrate such as a non-rodent nonhuman mammal or a bird) having an abnormality by which the development of the organ of interest does not occur at a developmental stage. The cell to be introduced is the cell of an animal (e.g., a nonhuman mammal or a vertebrate such as a non-rodent mammal or a bird) individual different from the nonhuman animal. The cell death suppression treatment (e.g., apoptosis suppression treatment) of the cell drastically improves the rate of chimera formation. Thus, in the nonhuman mammal or the non-rodent nonhuman mammal, the organ of interest that is not developed by the embryo to which the cell is to be introduced can be complemented by the introduced cell to obtain a chimeric animal with very high efficiency. Thus, the method of the present invention may further comprise the step of subjecting the cell to cell death suppression treatment. The relationship between the cell to be introduced and the embryo may be the same species or may be different species. From the viewpoint of using the organ in medical transplantation, the relationship between the cell to be introduced and the embryo is preferably different species, and the cell to be introduced is preferably a human-derived cell.

In the present invention, the organ of interest can be harvested from the chimeric mammal produced by blastocyst complementation. Hence, the present invention provides a method for producing an organ of interest, comprising producing a chimeric mammal by the method of the present invention and harvesting the organ of interest from the obtained chimeric mammal. The obtained organ of interest can be used in, for example, transplantation.

Usually, a knockout animal homozygously having a causative gene of a defect in an organ or a body part that results in inability or difficulty to survive is less likely to survive and fails to produce a newborn. Thus, such an animal is usually obtained by the crossing between viable animals each heterozygously having the causative gene of a defect in an organ or a body part that results in inability or difficulty to survive. In this case, according to the Mendel's laws, the animal having homozygously having a causative gene of a defect in an organ or a body part that results in inability or difficulty to survive is obtained only at a probability of theoretically 25% among newborns obtained by the crossing between the viable animals. According to a method developed by WO2009/104794, which is incorporated herein by reference, however, the animal homozygously having a causative gene of a defect in an organ or a body part that results in inability or difficulty to survive is allowed to grow until reproductive age by blastocyst complementation. According to this method, nonhuman animals (e.g., knockout nonhuman mammals) each homozygously having a causative gene of a defect in an organ or a body part that results in inability or difficulty to survive can be mated with each other to obtain a next-generation newborn homozygously having a causative gene of a defect in an organ or a body part that results in inability or difficulty to survive, at a probability of theoretically 100%. Thus, according to the method, a mammal (founder mammal) homozygously having a causative gene of a defect in an organ or a body part that results in inability or difficulty to survive can be obtained.

The cell having the ability to form a chimera can be used in the production of a founder mammal by use of blastocyst complementation as described above. Hence, the present invention provides a method for producing a founder mammal, comprising the steps of: a) preparing a primed pluripotent stem cell, a tissue stem cell, a progenitor cell, a somatic cell, or a germ cell; b) transplanting the cell into a fertilized egg at a blastocyst stage of a nonhuman mammal; c) developing the fertilized egg in the womb of a nonhuman foster mother mammal to obtain a newborn; and d) allowing the newborn individual to grow until reproductive age, wherein the nonhuman mammal is a nonhuman mammal having a causative gene of a defect in an organ or a body part that results in inability or difficulty to survive. In this context, the cell and the organ to be produced can be derived from a mammal individual different from the nonhuman mammal individual. In one embodiment of the present invention, the embryo to which the cell is to be introduced is an embryo derived from a nonhuman animal (e.g., a nonhuman mammal or a vertebrate such as a non-rodent nonhuman mammal or a bird) having a causative gene of a defect in an organ or a body part that results in inability or difficulty to survive. The cell to be introduced is the cell of a mammal (e.g., a nonhuman mammal or a vertebrate such as a non-rodent mammal or a bird) individual different from the nonhuman mammal. The cell death suppression treatment (e.g., apoptosis suppression treatment) of the cell drastically improves the rate of chimera formation. Thus, the method of the present invention may further comprise the step of subjecting the cell to cell death suppression treatment. The embryo to which the cell is to be introduced and the cell may be the same species or may be different species. From the viewpoint of merely allowing the founder to survive until reproductive age, the embryo and the cell are preferably the same species. In the present invention, the defect in an organ or a body part that results in inability or difficult to survive is complemented by the introduced cell.

In the present invention, a nonhuman chimeric animal having only a particular organ or body part as a chimera can be produced, provided that a tissue stem cell, a lineage-committed progenitor cell, a somatic cell, or a germ cell that contributes only to the particular organ or body part is used as the cell to be introduced to the embryo. In the case of producing, for example, an interspecific chimeric animal, the cell for embryonic introduction used may preferably make no contribution to a particular organ or body part, for example, but is not particularly limited to, the brain or the germline. In the present invention, therefore, a cell that makes no contribution to a particular organ or body part, for example, a tissue stem cell, a lineage-committed progenitor cell, a somatic cell, or a germ cell that makes no contribution to a particular organ or body part, can be used as the cell to be introduced into an embryo in order to restrict the contribution of the cell to the particular organ or body part. The chimeric animal having only a particular tissue or organ as a chimera can also be produced by use of a cell that contributes only to the particular organ or body part, for example, a tissue stem cell, a lineage-committed progenitor cell, a somatic cell, or a germ cell that contributes only to the particular organ or body part, as the cell to be introduced into an embryo. From a different viewpoint, the tissue stem cell, the lineage-committed progenitor cell, the somatic cell, or the germ cell is considered not to contribute to the whole body, because its differentiation fate is usually determined. Thus, use of the tissue stem cell, the lineage-committed progenitor cell, the somatic cell, or the germ cell achieves production of a chimeric animal having only a particular organ or body part as a chimera. In this context, the particular organ or body part may be one or more organs or body parts. As mentioned later, in the case where the embryo to which the cell is to be introduced is the embryo of a mammal having an abnormality by which the development of an organ does not occur at a developmental stage or is the embryo of a nonhuman animal containing a causative gene of a defect in an organ or a body part that results in inability or difficulty to survive, a cell that can complement the defect (e.g., a cell capable of differentiating into the organ or the body part) is preferably used. As mentioned above, in the case where the cell to be introduced into an embryo is a cell that has been subjected to cell death suppression treatment (e.g., apoptosis suppression treatment), the cell has the drastically improved rate of chimera formation while maintaining its differentiation fate. Thus, in a certain embodiment of the present invention, the cell to be introduced into an embryo is a cell that has been subjected to cell death suppression treatment (e.g., apoptosis suppression treatment) or a cell death-resistant cell (e.g., an apoptosis-resistant cell).

In the present invention, the "organ" refers to a visceral organ of an animal. Examples of the organ, but are not particularly limited to, the heart, the lung, the kidney, the pancreas, the thymus, the spleen, the liver, the cerebellum, the small intestine, the colon, and the bladder. These organs can be complemented according to the present invention. In an embodiment of the present invention, the organ can be, for example, the pancreas, the kidney, or the thymus.

In the present invention, the "body part" refers to any part of the body. Examples of the body part include blood vessels, blood, lymphocytes, bones, and hair. These body parts can be complemented according to the present invention. In an embodiment of the present invention, the body part can be, for example, lymphocytes or hair. In the present specification, tissues are also included in the body part.

In the present invention, the "cell of an animal individual different from the nonhuman animal" refers to a cell that can complement the abnormality or the defect possessed by the embryo of the nonhuman animal. Examples thereof include wild-type cells and cells expressing fluorescent proteins.

The suppression of the cell death (e.g., apoptosis) of cells improved the ability to form a chimera. Hence, the present invention provides a method for improving the ability of a primed pluripotent stem cell, a tissue stem cell, a progenitor cell, a somatic cell, or a germ cell to form a chimera, comprising subjecting the cell to cell death suppression treatment (e.g., apoptosis suppression treatment).

The suppression of the cell death (e.g., apoptosis) of cells improves the ability to form a chimera is presumably because: particularly, in an early stage of development (e.g., pre-implantation), in the case where the developmental stage of an embryo and the developmental stage or prospective fate of a cell to be introduced largely differ temporally and spatially (e.g., in the case of introducing an epiblast stem cell to a blastocyst), the cell rarely contributes to a chimeric animal. Nonetheless, the cell death suppression treatment (e.g., apoptosis suppression treatment) of the cell facilitates the contribution of the cell to a chimeric animal. This suggests the possibility that the introduced cell is killed due to cell death (e.g., apoptosis) when introduced to an embryo differing therefrom in developmental stage; thus the cell cannot contribute to a chimeric animal. The suppression of cell death (e.g., apoptosis) probably allows the cell to survive without being killed until the developmental stage of the embryo is synchronized to the developmental stage of the cell. This seems to be the reason why a chimeric animal was able to be produced from the cell that lost its ability to form a chimera. In the case of using, for example, a lineage-committed progenitor cell, the embryo was developed until its developmental stage agreed with that of this cell, and the cell was able to survive until their developmental stages were synchronized to each other. This probably allowed the lineage-committed progenitor cell to be developed and differentiated in a later embryo.

In the present invention, epiblast stem cells (EpiSC) that underwent apoptosis suppression treatment exhibited a differentiation potential into a germ cell. Hence, the present invention provides a method for imparting a differentiation potential into a germ cell to a primed pluripotent stem cell or improving the differentiation potential, comprising subjecting the pluripotent stem cell to cell death suppression treatment (e.g., apoptosis suppression treatment).

In the present invention, EpiSC that underwent apoptosis suppression treatment exhibited a gene expression pattern different from that of ordinary EpiSC, whereas this EpiSC exhibited a gene expression pattern similar to that of naïve ES cells. Particularly, the epiblast stem cells exhibited the gene expression pattern of naïve pluripotent stem cells as a result of the apoptosis suppression treatment of the cells. In addition, the colony morphology was also changed to the morphology of naïve pluripotent stem cells, not primed type. This suggests that in the present invention, the cell death suppression treatment (e.g., apoptosis suppression treatment) was able to alter (convert) primed pluripotent stem cells to naïve pluripotent stem cells. In the present invention, the obtained naïve pluripotent stem cells were CD31-positive cells. Hence, the present invention may further provide the fractionation of a CD31-positive cell from pluripotent stem cells that have been subjected to apoptosis suppression treatment. Thus, from a pluripotent stem cell population having the improved ability to form a chimera, a naïve pluripotent stem cell constituting a portion thereof can be effectively harvested. The fractionation of a CD31-positive cell can be carried out by a method well known to those skilled in the art (e.g., using a cell sorter and an anti-CD31 antibody).

As mentioned above, in the present invention, the apoptosis suppression treatment was able to render primed pluripotent stem cells less differentiated. Hence, the present invention provides a method for rendering a mammalian primed pluripotent stem cell, a tissue stem cell, a progenitor cell, a somatic cell, or a germ cell less differentiated, comprising subjecting the cell to cell death suppression treatment (e.g., apoptosis suppression treatment). In one embodiment of the present invention, the cell to be rendered less differentiated is a mammalian primed pluripotent stem cell.

According to a certain aspect, the present invention provides a method for producing a naïve pluripotent stem cell from a primed pluripotent stem cell (e.g., a rodent primed pluripotent stem cell such as an epiblast stem cell, or a non-rodent mammalian primed pluripotent stem cell), comprising subjecting the primed pluripotent stem cell to cell death suppression treatment (e.g., apoptosis suppression treatment), and a naïve pluripotent stem cell produced by this method. The cell death suppression treatment (e.g., apoptosis suppression treatment) can be carried out, for example, until the morphology of a colony formed by the cell during adherent culture becomes naïve pluripotent stem cell-like morphology. Whether or not the primed pluripotent stem cell has become a naïve pluripotent stem cell can be determined by the confirmation of change in biological and/or physiological features.

According to a certain aspect, the present invention provides a method for producing a pluripotent stem cell capable of forming a multi-layer colony in adherent culture from a primed pluripotent stem cell (e.g., a rodent primed pluripotent stem cell such as an epiblast stem cell, or a non-rodent mammalian primed pluripotent stem cell), comprising subjecting the primed pluripotent stem cell to cell death suppression treatment (e.g., apoptosis suppression treatment), and a pluripotent stem cell produced by this method. The cell death suppression treatment (e.g., apoptosis suppression treatment) can be carried out, for example, until the morphology of a colony formed by the cell during adherent culture becomes multi-layer cell morphology.

The present invention provides an agent for use in promoting reprogramming a primed pluripotent stem cell, the agent comprising a cell death suppressor (e.g., an apoptosis suppressor, a necrosis suppressor, or an autophagy suppressor). In the present specification, the "an agent for use in promoting reprogramming" means an agent that promotes the conversion of the primed pluripotent stem cell to a cell in a complete reprogrammed state (naïve state or ground state). In the present specification, the "an agent for use in promoting reprogramming" does not necessarily mean an agent that achieves a complete reprogrammed state. The agent for use in promoting reprogramming of the present invention is an agent for rendering the primed pluripotent stem cell less differentiated. In some cases, the agent for use in promoting reprogramming of the present invention can render the primed pluripotent stem cell undifferentiated to yield a naïve pluripotent stem cell. Hence, the present invention provides an agent for use in inducing a naïve pluripotent stem cell for use in a primed pluripotent stem cell. In the present invention, every compound capable of suppressing the cell death of the cell, as described above, can be used as the cell death suppressor.

The present invention relates to use of a cell death suppressor (e.g., an apoptosis suppressor, a necrosis suppressor, or an autophagy suppressor) for the production of an agent for use in promoting reprogramming of a primed pluripotent stem cell. The present invention also relates to use of a cell death suppressor (e.g., an apoptosis suppressor, a necrosis suppressor, or an autophagy suppressor) for the production of an agent for use in inducing a naïve pluripotent stem cell in a primed pluripotent stem cell. The present invention further relates to use of a cell death suppressor (e.g., an apoptosis suppressor, a necrosis suppressor, or an autophagy suppressor) for the production of a naïve stem cell from a primed pluripotent stem cell.

In the present invention, a chimeric animal can be produced using a cell having no ability to form a chimera or a cell considered to have no ability to form a chimera, as the cell to be introduced into an embryo. The cell having no ability to form a chimera can be used as the cell to be introduced into an embryo in the production of a chimeric animal and examined for its differentiation into a tissue in the body of the chimeric animal to evaluate the differentiation potential of the cell used as the cell for embryonic introduction. Hence, the present invention provides a method for evaluating the differentiation potential of a cell, comprising producing a chimeric mammal by a method of the present invention (provided that the cell to be evaluated is used as a cell that is introduced to the embryo of a nonhuman mammal) and examining the contribution of the cell to each tissue in the produced chimeric mammal to evaluate the differentiation potential of the cell into each tissue. For confirming the distribution of the cell in the chimeric mammal, the cell is preferably labeled without particular limitations. The label is not particularly limited as long as the label allows discrimination between the embryo and the cell to be introduced into an embryo. Examples thereof include: fluorescent proteins such as green fluorescent protein (GFP), blue fluorescent protein (CFP), red fluorescent protein (RFP), Venus, DsRed, tdTomato, and their modified forms; and luminescent proteins such as luciferase. For example, the cell to be introduced into an embryo can be forced to express any of these fluorescent proteins or their modified forms so that the distribution of a cell derived from the cell which was introduced into the embryo is easily analyzed in the obtained chimeric animal. For the evaluation of the differentiation potential, the cell to be introduced into an embryo or the embryo may be treated with a compound before introduction to the embryo. Change in differentiation potential caused by the presence and absence of the compound treatment can be examined to examine the influence of the compound on the differentiation potential of the cell. For the evaluation of the differentiation potential, the expression of a particular gene may be induced or suppressed in the cell to be introduced into an embryo to evaluate the influence of the gene on the differentiation of the cell. Various cells prepared from pluripotent stem cells under culture are desirably evaluated in advance for their functions and safety (e.g., evaluated for whether or not to have normal functions or whether or not to be free from malignant cell transformation). In the present invention, such a cell can be used as the cell to be introduced into an embryo to evaluate the in vivo function or safety of the cell. Hence, the present invention provides a method for evaluating the in vivo function or safety of a cell in addition to the differentiation potential of the cell into each tissue.

The evaluation method of the present invention can be used in the screening of a compound. Hence, the present invention provides a method for screening for a compound that enhances or reduces the ability of a cell to form a chimera and/or the differentiation potential of a cell, comprising
    contacting compounds with a cell;
    using the cell as a cell to be introduced into an embryo to produce a chimeric animal, and examining the distribution of the cell in the body of the chimeric animal to evaluate the ability of the cell to form a chimera and/or the differentiation potential of the cell; and selecting a compound that positively or negatively influences the ability of the cell to form a chimera and/or the differentiation potential of the cell, on the basis of the evaluation results.

The screening method of the present invention can be used in the screening of a compound having the effect of inducing the differentiation of the cell, a compound having the effect of rendering the cell less differentiated, a compound having the effect of determining the differentiation fate of the cell, or the like. In the evaluation of the ability to form a chimera and/or the differentiation potential, the contribution of the cell to the chimeric animal may be examined on an organ basis or tissue basis.

In the method for producing a chimeric animal according to the present invention, the primed pluripotent stem cell, the tissue stem cell, the progenitor cell, the somatic cell, or the germ cell may be introduced to the embryo and, if necessary, subjected to cell death suppression treatment (e.g., apoptosis suppression treatment). The other procedures can be carried out according to an ordinary method for producing a chimeric mammal. Specifically, the chimeric mammal can be produced by introducing a cell having the ability to form a chimera to the embryo of a different individual of the same species thereas or an individual of different species therefrom (e.g., the cell can be introduced using a micromanipulation technique), and then transplanting the cell-introduced embryo into the uterus of a pseudopregnant foster mother, followed by development. The chimeric animal can be obtained as a newborn by delivery. The chimeric animal can also be obtained as an adult by the growth of the newborn.

In the present invention, the apoptosis suppression treatment of human iPS cells was able to improve their ability to form a chimera. Hence, the present invention provides a method for improving the ability of a human pluripotent stem cell to form a chimera, comprising subjecting the human pluripotent stem cell to cell death suppression treatment. The present invention also provides a method for producing a chimeric animal, comprising introducing a human pluripotent stem cell to the embryo of a mammal, wherein the cell has been subjected to cell death suppression treatment. Examples of the human pluripotent stem cell include human ES cells and iPS cells, which can be used in the present invention. In the present invention, an iPS cell selected from those having high ability to form a chimera (e.g., those having higher ability than average) can have the further improved rate of chimera formation.

EXAMPLES

Example 1A: Chimeric Mouse Preparation Using Epiblast Stem Cell

In this Example, chimeric mouse preparation was attempted using mouse epiblast stem cells (EpiSC).

First, the EpiSC line (main population) used in Examples was prepared according to the method described in Tesar et al., Nature (2007), 448 (7150): 196-199. Specifically, cells obtained by the cutting of mouse epiblasts were dissociated with a trypsin/EDTA solution and then seeded on a plate coated by mouse embryonic fibroblasts (MEFs) which have been treated for growth inactivation as feeder cells. Subsequently, grown colonies were cloned to establish an EpiSC line.

EpiSC was maintained in a medium constituted by knockout D-MEM supplemented with a 15% knockout serum replacement, 1% non-essential amino acids, 2 mM Glutamax or L-glutamine, 0.1 mM 2-mercaptoethanol (manufactured by Life Technologies Corp.), and basic fibroblast growth factor (bFGF) (manufactured by PeproTech Inc.). EpiSC was subcultured every 3 to 5 days before becoming completely confluent.

EpiSC was labeled with a fluorescent protein tdTomato. Specifically, EpiSC was infected by lentivirus expression vectors for the expression of tdTomato (Takara Bio Inc.) under the control of CAG promoter. Then, tdTomato-expressing cells were isolated by FACS (MoFlo: Beckman Coulter, Inc.; Aria: Becton, Dickinson and Company) before injection.

The obtained EpiSC (hereinafter, also referred to as "EpiSC-tdT") was introduced to blastocyst-stage embryos by microinjection to prepare chimeric embryos. Specifically, BDF1 (C57BL6/N; DBA1 F1) or ICR mouse embryos were first cultured in Medium 2 (manufactured by Millipore Corp.) to prepare 8-cell or morula-stage embryos. The obtained embryos were transferred to a KSOM medium (manufactured by Millipore Corp.) and developed into blastocyst stage by culture for 24 hours. EpiSC to be injected to the embryos were dissociated into single cells by trypsin treatment and suspended in a medium. The transparent bodies were punched using a piezo-based micromanipulator under a microscope. Approximately 10 EpiSC cells per embryo were injected into the subzonal space to prepare chimeric embryos.

After the injection, the embryos were cultured in a KSOM medium until becoming blastomeres. Then, the embryos were transplanted into the uteri of pseudopregnant recipient ICR female mice.

Figure 1B:
FIGS. 1B and 1C show microscopic images of fetuses obtained using Bcl-2-untransfected epiblast stem cells (control).
Figure 1C:

The embryos were recovered 10 days after the transplantation (which correspond to embryonic day 12.5 (E12.5) of normally developed embryos). As a result of confirming the embryos under a fluorescence microscope, no signal of tdTomato was observed (FIGS. 1B and 1C). Specifically, this EpiSC-tdT line failed to form a chimera. These results are consistent with the previous report (e.g., Tesar et al., Nature (2007), 448 (7150): 196-199).

Example 2A: Chimeric Mouse Preparation Using EpiSC Forced to Express Bcl-2

Accordingly, the present inventors studied various factors and consequently found that EpiSC transfected with Bcl-2 gene known as an anti-apoptotic factor has the ability to form a chimera.

The Bcl-2 gene used was human BCL-2 gene (GenBank Accession No. BC027258.1) or mouse Bcl-2 gene (GenBank Accession No. BC095964.1). EpiSC-tdT was transfected with the Bcl-2 gene using Tet-on all-in-one inducible lentivirus vector (AiLV; Yamaguchi et al., 2012). Specifically, Tet-on AiLV was constructed using tetracycline (tet) responsive element and reverse tet transactivator (rtTA) (FIG. 1A). In this system, Bcl-2 can be intracellularly expressed by the addition of tetracycline or its derivative doxycycline. In order to discriminate virus-integrated cells from unintegrated cells, EGFP gene was operably linked to rtTA driven by human ubiquitin C (Ubc) promoter in this Tet-on AiLV.

EpiSC-tdT transfected with Tet-on-Bcl-2 (EpiSC-tdT-TRE-Bcl-2) was isolated by FACS with the fluorescence intensity of EGFP as an index. From 24 to 48 hours before injection to blastocysts, the cells were treated with 1 μg/mL doxycycline in a medium to induce the expression of Bcl-2.

Figure 1D:
FIGS. 1D and 1E show microscopic images of fetuses obtained using Bcl-2-transfected epiblast stem cells.
Figure 1E:
Figure 1F:
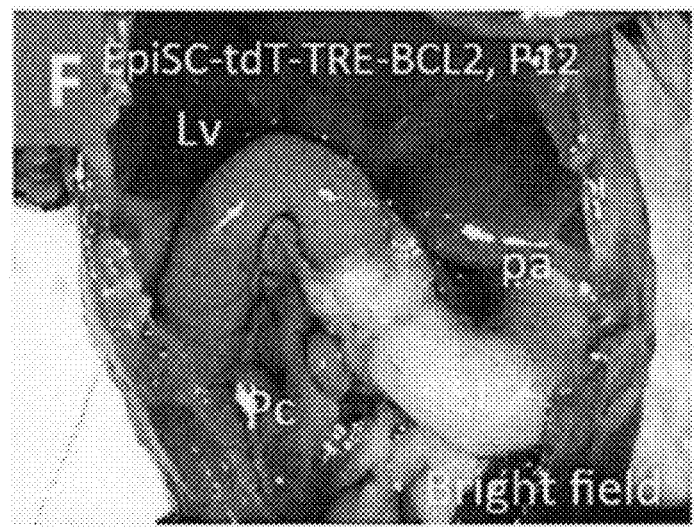
FIGS. 1F to 1I show microscopic images of the viscera of a newborn obtained using Bcl-2-transfected epiblast stem cells.
Figure 1G:
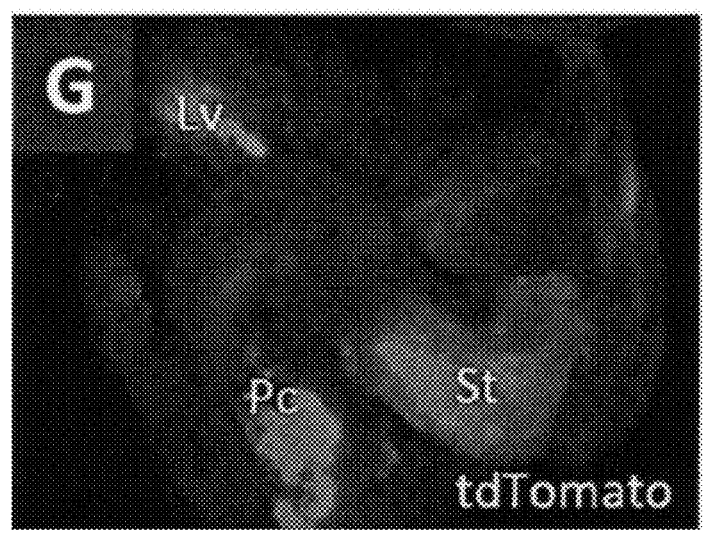
Figure 1H:
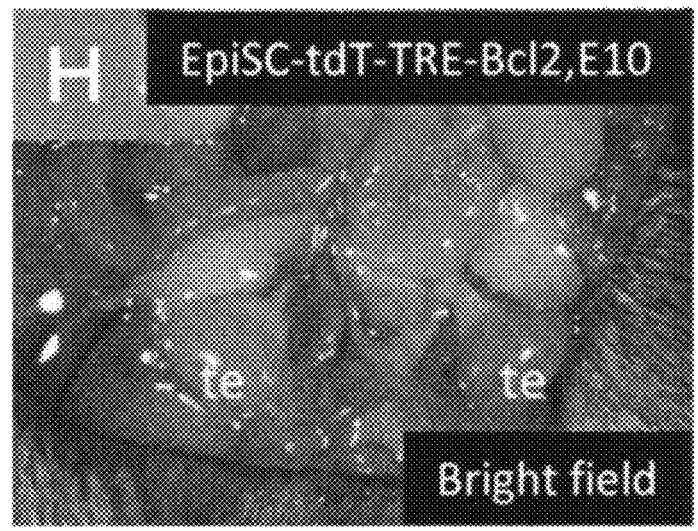
Figure 1I:
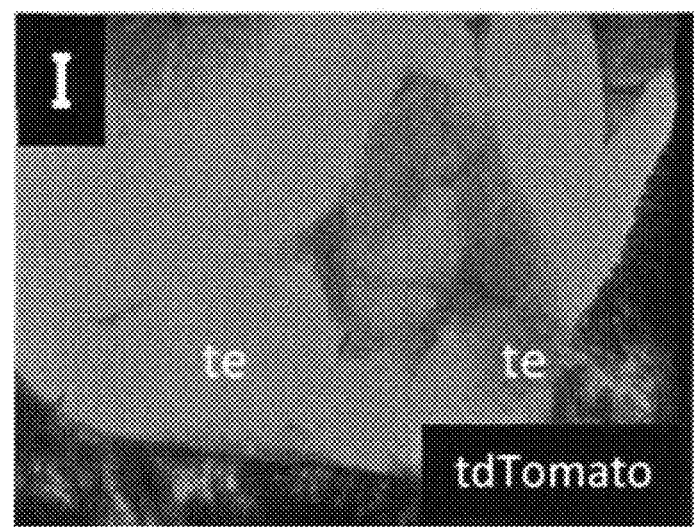

EpiSC-tdT-TRE-Bcl-2 obtained using a micromanipulator was injected to mouse blastocysts. The embryos were transplanted to the uteri of recipient mice as mentioned above. The recipient mice were each given a 2 mg/mL aqueous doxycycline solution for 1 week after the transplantation of the embryos. E12.5 embryos were recovered and observed under a fluorescence microscope. As a result, the cells derived from EpiSC-tdT-TRE-Bcl-2 contributed to the whole bodies of fetuses (FIGS. 1D and 1E). Specifically, use of EpiSC forced to express Bcl-2 as the cell for embryonic introduction permitted highly efficient preparation of chimeric animals.

The chimeric mice thus obtained were normally developed and delivered. As a result of dissecting and observing the mice of 9 days after birth, the introduced EpiSC contributed to all observed tissues (from the lung, the pancreas, the stomach, the germline (testis) and other organs, etc.) (FIGS. 1F, 1G, 1H, and 1I). In order to elucidate the contribution of the cells to the germline, tissue sections were used to confirm their localization with a germ cell marker mouse vasa homolog (Mvh). As a result, the introduced EpiSC was shown to be colocalized with Mvh-expressing cells on the tissue sections (FIGS. 1K to 1P). The colocalization was observed as follows: first, gonads were harvested from E12.5 chimeric mouse embryos, fixed in a 10% paraformaldehyde solution for 2 hours, and then left overnight in a 30% sucrose solution. Then, the gonads were embedded in O.C.T. Compound (manufactured by Tissue-Tek), and then, frozen blocks were prepared. From the frozen blocks, frozen sections of 7 μm in thickness were prepared using Cryostat (Leica Biosystems Nussloch GmbH, CM3050S). The frozen sections were fluorescently immunostained with an antibody (Abcam, #13840) against the germ cell marker mouse vasa homolog (Mvh) as a primary antibody and an Alexa 647-conjugated anti-rabbit IgG antibody as a secondary antibody and observed under a fluorescence microscope (Keyence Corp., BZ-9000). As a result of the observation, in the gonads derived from the chimeric mice prepared by the transplantation of EpiSC-A-TRE-BCL2 cells (FIGS. 1K to 1M), a portion of DsRed-positive transplanted cells expressed Mvh (arrows in FIGS. 1L and 1M). Also, in the gonads derived from the chimeric mice prepared by the transplantation of EpiSC-B-TRE-BCL2 cells (FIGS. 1N to 1P), a portion of tdTomato-positive transplanted cells expressed Mvh (arrows in FIGS. 1O and 1P). These results demonstrated that the transplanted epiblast stem cell line can differentiate into germ cells.

Figure 1J:
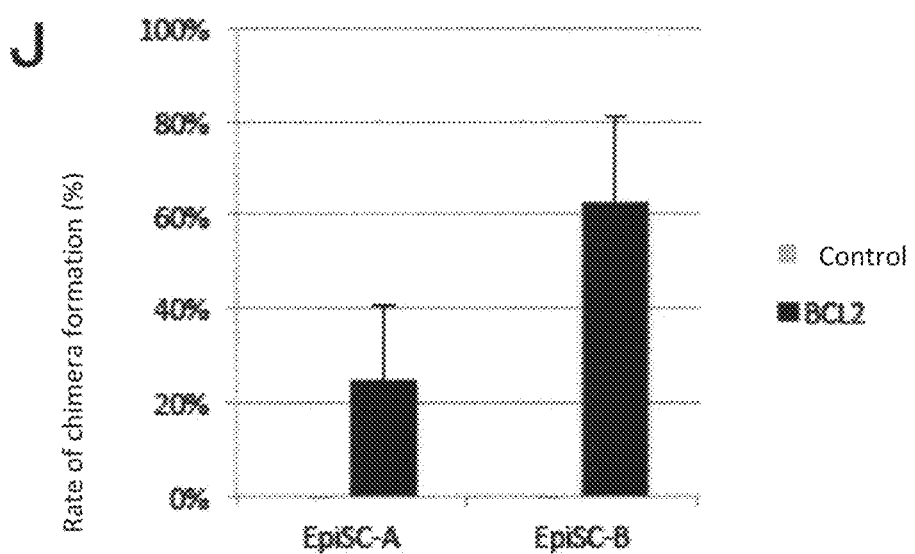
FIG. 1J is a diagram showing the effect of forced Bcl-2 expression on the rates of chimera formation of two EpiSC lines. In the drawing, "Lv" represents the liver, "Pc" represents the pancreas, "St" represents the stomach, and "te" represents the testis.
Figure 1K:
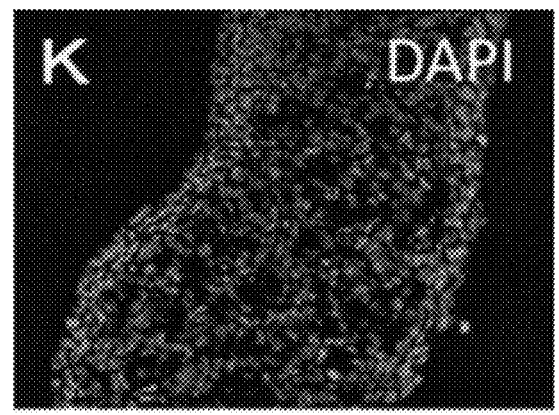
Figure 1L:
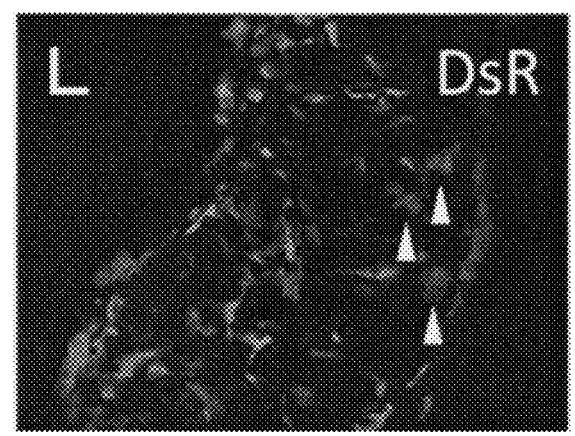
Figure 1M:
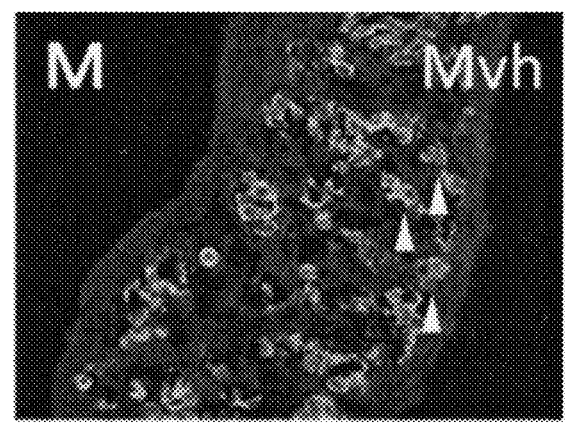
Figure 1N:
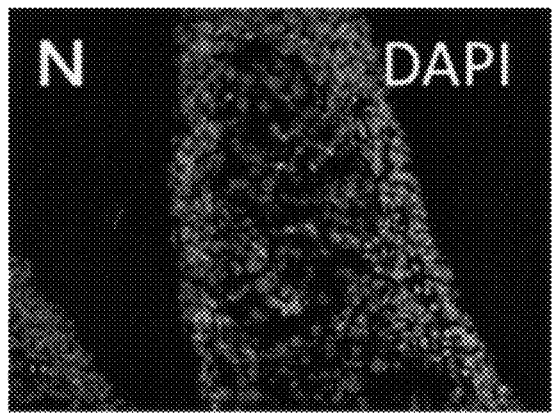
Figure 1O:
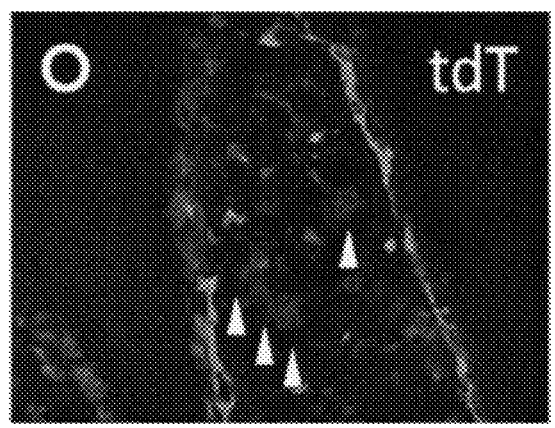
Figure 1P:
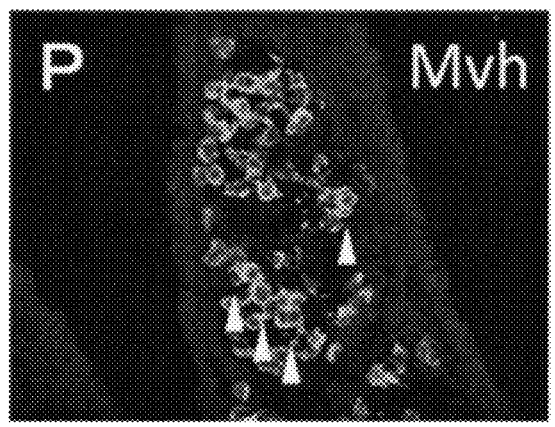

Instead of EpiSC-tdT, EB3DR-derived EpiSC (EpiSC-A-Bcl2) or BDF-1-derived EpiSC (EpiSC-B-Bcl2) were used to prepare chimeric mice. In this case as well, the ability to form a chimera was confirmed. The rates of chimera formation were approximately 25% and approximately 60%, respectively (FIG. 1J). As described above, EpiSC had the improved ability to form a chimera as a result of the introduction of Bcl-2 and its forced expression in the cell. EB3DR-derived EpiSC (EpiSC-A) refers to EpiSC that is derived from EB3DR ES cells and has a gene in which the DsRed-T4 gene is linked under the control of a CAG expression unit. The EB3DR mouse ES cell line was kindly provided by professor Hitoshi Niwa (Riken Center for Developmental Biology). EpiSC was established from chimeric epiblast embryos prepared by the transplantation of EB3DR into mouse embryos. Then, DsRed-expressing cells were isolated using FACS. These cells were transfected with tet-on-BCL2 expression vectors to prepare Bcl-2-expressing cells (EpiSC-A-TRE-Bcl-2).

Figure 2A:
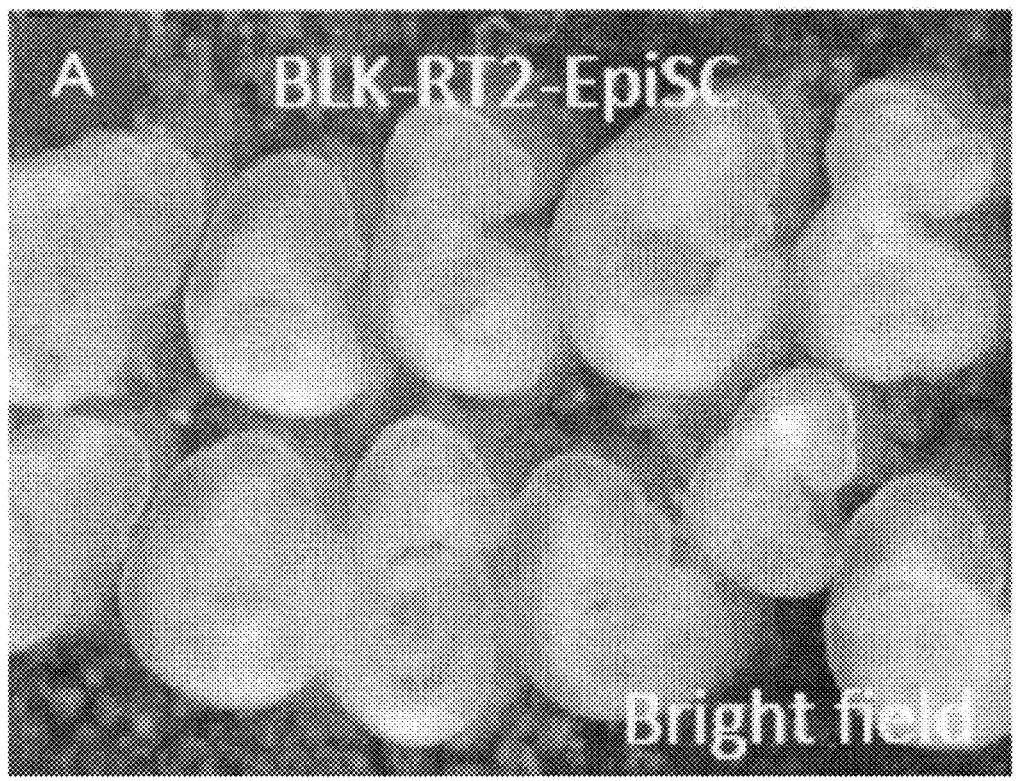
FIGS. 2A to 2E show optical microscopic images (FIGS. 2A and 2C) and fluorescence microscopic images (FIGS. 2B and 2D) of fetuses obtained using rat epiblast stem cells transfected with Bcl-2-encoding gene.
Figure 2B:
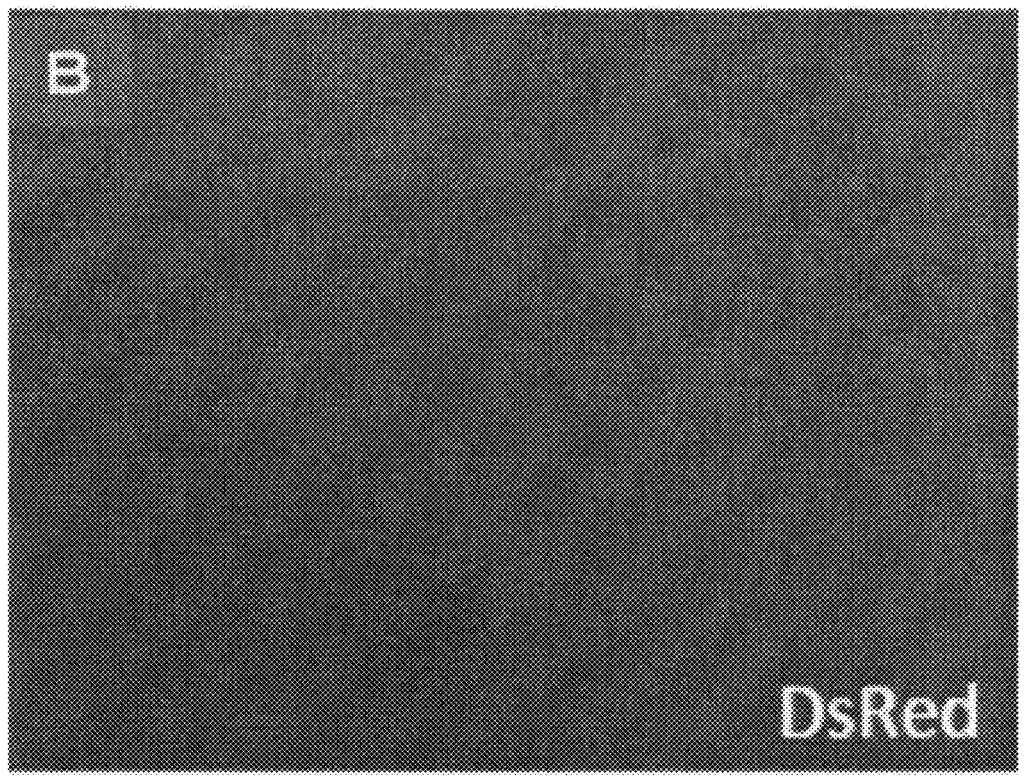
Figure 2C:
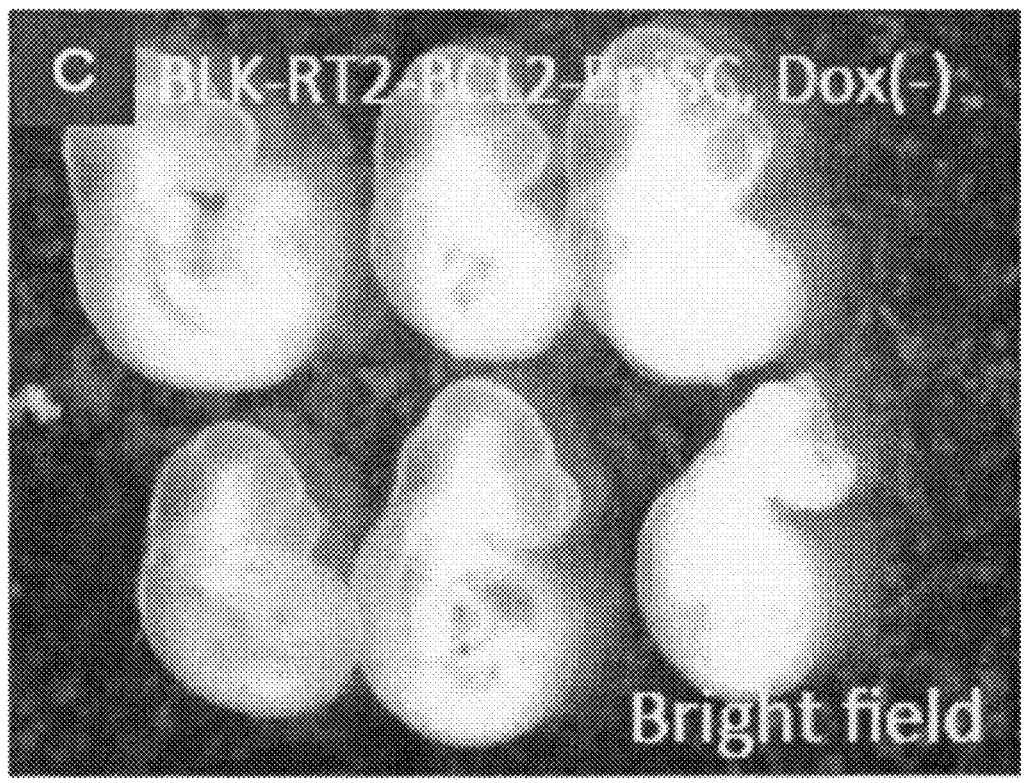
Figure 2D:
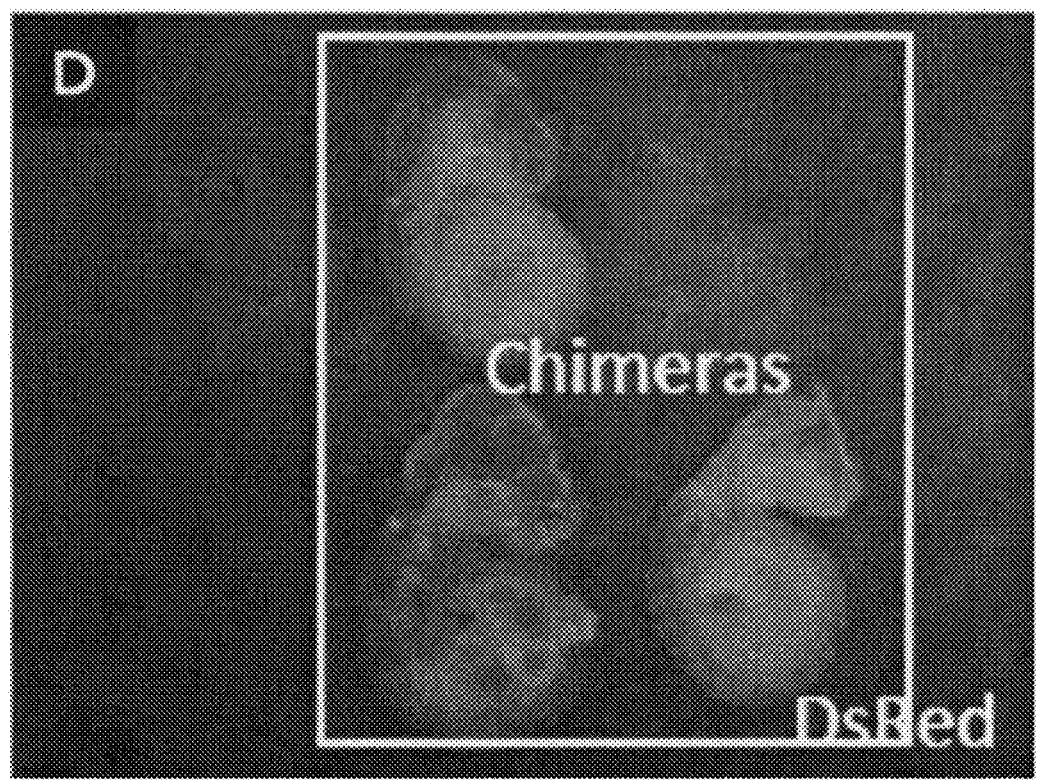
Figure 2E:
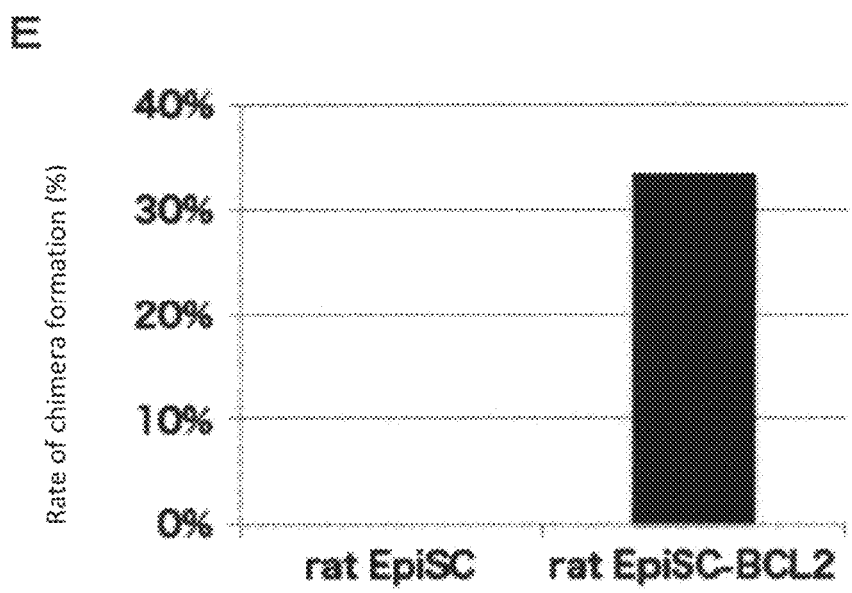

As a result of verifying whether rat EpiSC forced to express Bcl-2 (BLK-RT2-EpiSC-BCL2) was introduced instead of mouse EpiSC to mouse blastocysts as described in this Example to prepare interspecific chimeras, the chimeras were successfully prepared by using the rat EpiSC as the cell for embryonic introduction and introducing the cells to mouse embryos (i.e., embryos of different species) (FIGS. 2D and 2E). The rat BLK-RT2-EpiSC was obtained by: establishing EpiSC in the same way as in Example 1A from interspecific chimeric epiblast embryos prepared by the transplantation of BLK-RT2 rat ES cells expressing tdTomato under the control of Rosa26 promoter (Kobayashi et al., 2012) into mouse blastocyst embryos; and selecting tdTomato-expressing cells by FACS. The cells were transfected with the tet-on-BCL2 gene (BLK-RT2-EpiSC-BCL2) in the same way as in Example 1A. Both for the rats and for the interspecific chimeras, the expression of the BCL2 gene enabled chimera formation.

The Bcl-2 gene used in this Example was a human-derived gene and was able to function normally in mice and rats. Thus, for imparting the ability to form a chimera to EpiSC, it was found unnecessary to use Bcl-2 gene derived from the same species. Transfection with mouse-derived Bcl-2 gene produced similar results (data not shown). These results also demonstrated that EpiSC forced to express Bcl-2 can be used as the cell for embryonic introduction in the preparation of interspecific chimeric animals.

Example 3A: Chimeric Mouse Preparation Using Endodermal Lineage Progenitor Cell

This Example verified whether even endodermal lineage progenitor cells further differentiated from EpiSC could be used in the preparation of chimeric animals by the forced expression of the Bcl-2 gene.

Endodermal lineage progenitor cells forced to express the Bcl-2 gene were obtained in the same way as in Example 1A except that the cells used were changed to endodermal lineage cells. A K17-5 mouse ESC line modified by the knockin of human CD25 in the endogenous Sox17 gene locus to express human CD25 at the same time with the expression of Sox17 (Yasunaga et al., 2005) was used for obtaining the endodermal lineage progenitor cells. By use of this cell line, the expression of Sox17 can be evaluated with the expression of human CD25 as an index, and the endodermal lineage progenitor cells can thereby be conveniently isolated.

Figure 3A:
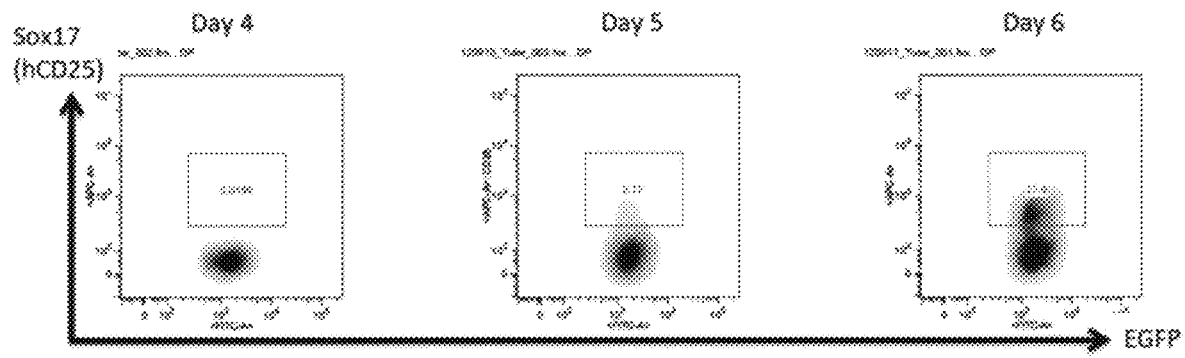
FIGS. 3A to 3E are a diagram showing the obtainment of Sox17-expressing mouse endodermal lineage progenitor cells from mouse ES cell line K17-5 cells transfected with Sox17 reporter (FIG. 3A), and the expression levels of pluripotent stem cell markers (FIG. 3B), ectoderm markers (FIG. 3C), mesoderm markers (FIG. 3D), and endoderm markers (FIG. 3E) in the obtained Sox17-expressing endodermal lineage progenitor cells.

First, the mouse ESC line K17-5 were infected by Tet-on AiLV expressing the Bcl-2 gene as described in Example 1A, and EGFP-expressing cells were isolated using FACS to obtain K17-5-TRE-Bcl-2 cells harboring the Bcl-2 gene. Next, in order to enhance EGFP signals, the cells were further infected by lentivirus vectors for the expression of EGFP gene linked to CAG promoter. Cells with stronger EGFP signals (K17-5-TRE-Bcl-2-GFP) were isolated by FACS. The obtained cells were allowed to proliferate and then seeded on a collagen IV-coated plate (manufactured by IWAKI/Asahi Glass Co., Ltd.) in a S-clone SF—$O_3$ medium (manufactured by EIDIA Co., Ltd.) supplemented with 0.1% bovine serum albumin (manufactured by Life Technologies Corp.) and 10 μg/mL activin A (manufactured by PeproTech Inc.). At day 5 of differentiation and culture, K17-5-TRE-Bcl-2-GFP started to express Sox17 (FIG. 3A). The endodermal lineage progenitor cells were obtained at day 6 of differentiation and culture by the isolation of human CD25-expressing cells by sorting from among the EGFP-expressing cells.

Figure 3B:
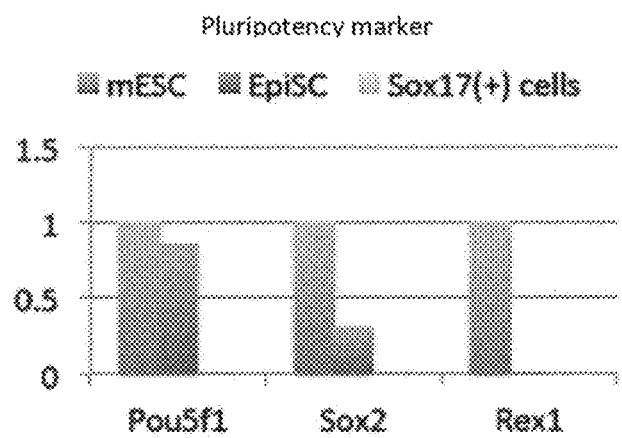
Figure 3C:
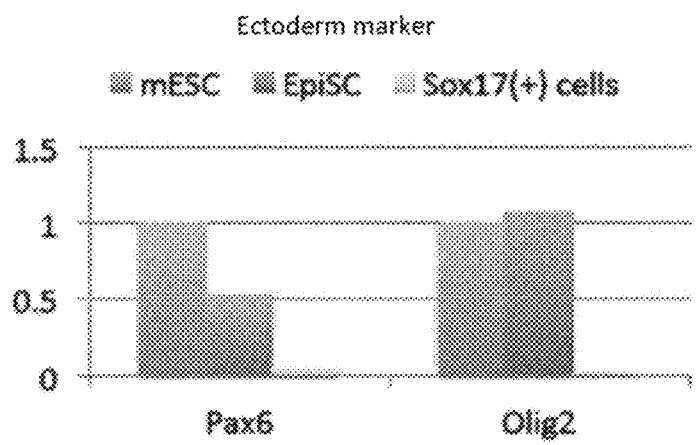
Figure 3D:
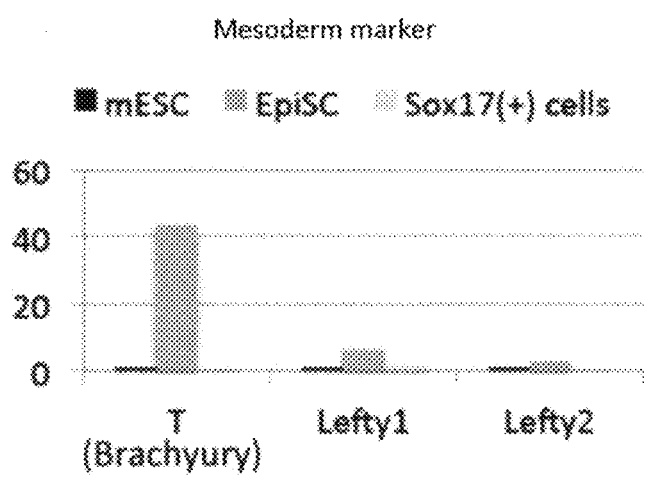
Figure 3E:
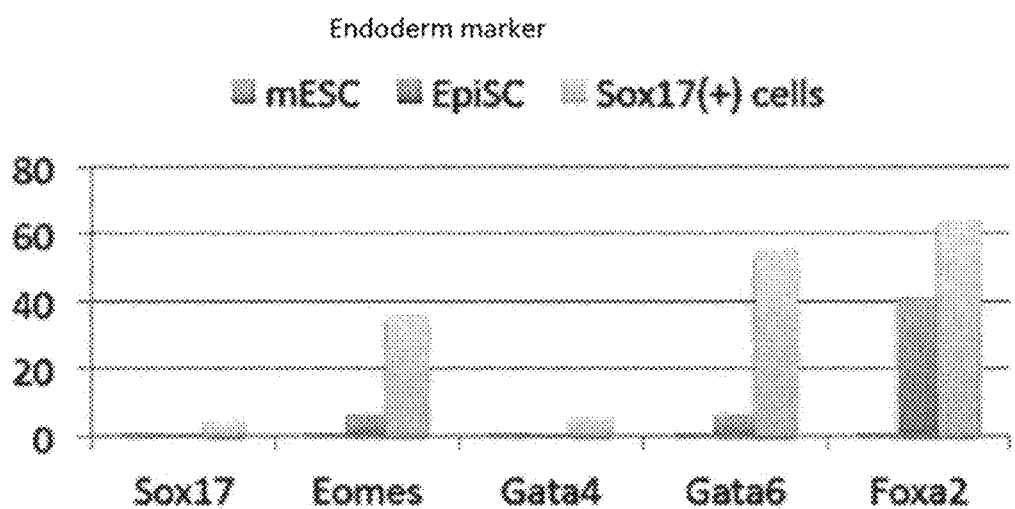

The obtained endodermal lineage progenitor cells were analyzed using Taqman Mouse Stem Cell Pluripotency Array (manufactured by Life Technologies Corp.) according to the manufacturer's manual. The results were compared with EB3DR mouse embryonic stem cells (EB3DR mESC) and EB3DR-derived EpiSC and normalized with the values of ES cells. As a result, the human CD25-positive cells (i.e., Sox17-expressing cells) derived from K17-5-TRE-Bcl-2-GFP exhibited no expression of pluripotency markers (Oct4, Sox2, and Rex1) and exhibited neither the expression of neural differentiation markers (Pax6 and Olig2) nor the expression of mesoderm markers (FIGS. 3B to 2D). By contrast, the CD25-positive cells derived from K17-5-TRE-Bcl-2-GFP strongly expressed endoderm markers (FIG. 3E). From these results, the human CD25-positive cells derived from K17-5-TRE-Bcl-2-GFP were confirmed to be endodermal lineage progenitor cells, not pluripotent stem cells.

Figure 4A:
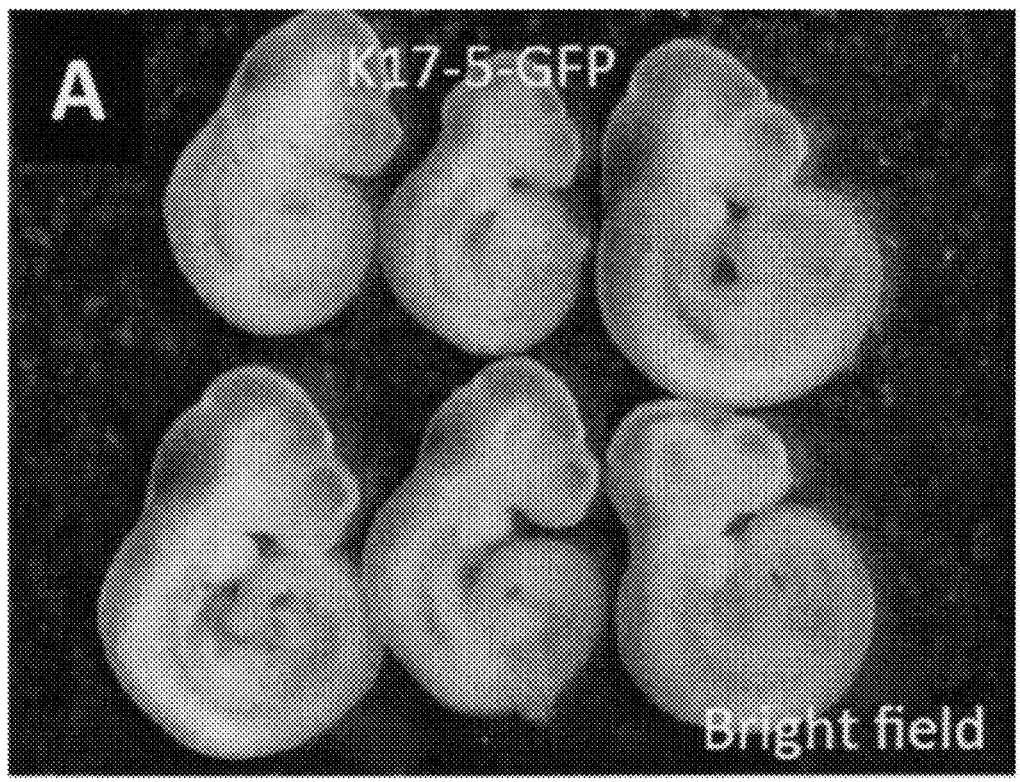
FIGS. 4A to 4D are a diagram showing optical microscopic images (FIGS. 4A and 4C) and fluorescence microscopic images (FIGS. 4B and 4D) of fetuses obtained by the introduction of endodermal lineage progenitor cells obtained by the transfection of K17-5 cells with Bcl-2-encoding gene followed by the induction of differentiation.
Figure 4B:
Figure 4C:
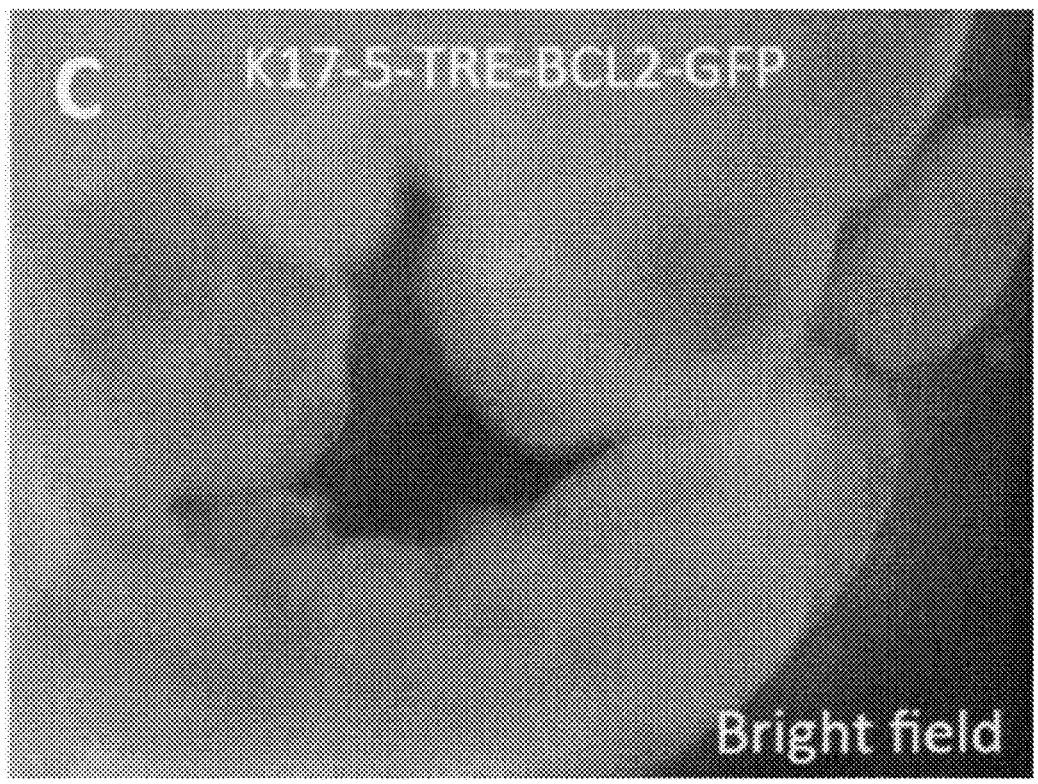
Figure 4D:
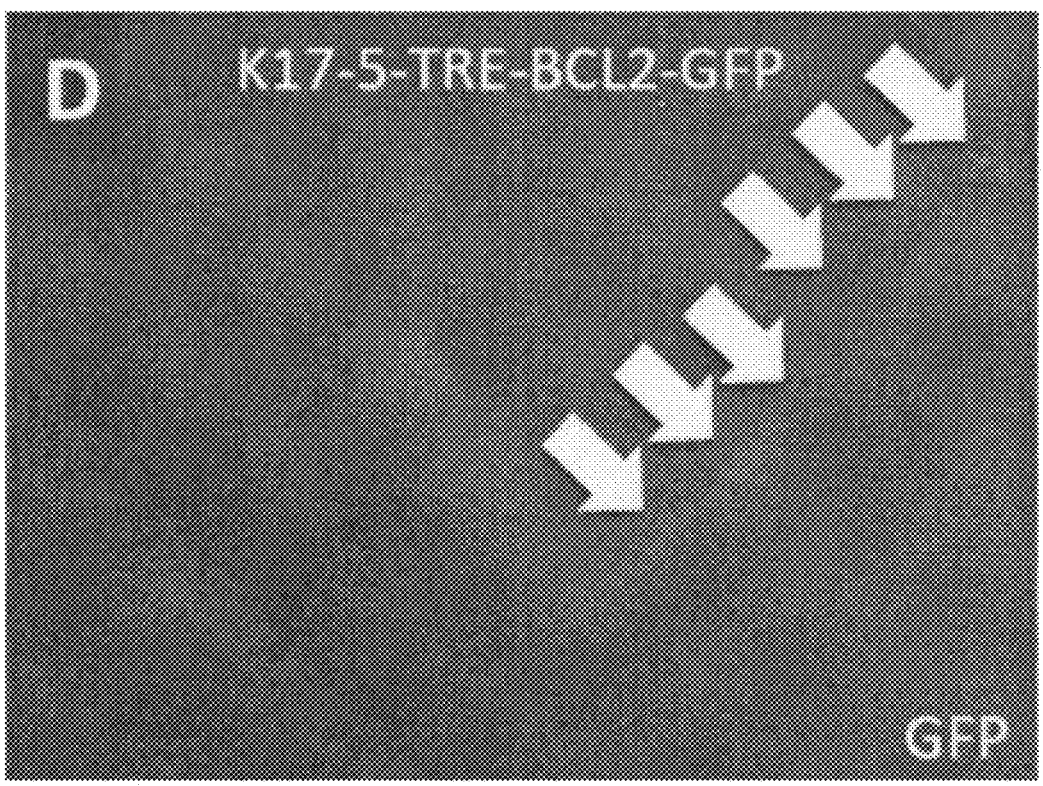
Figure 5A:
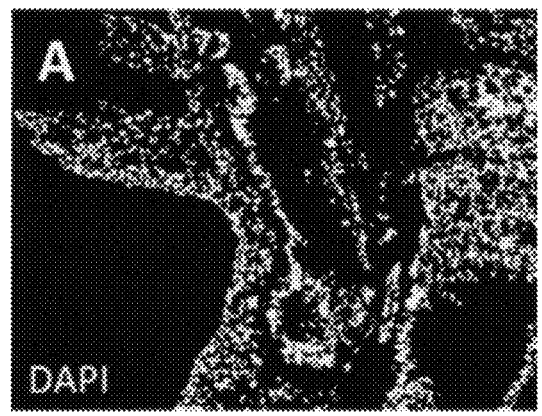
FIGS. 5A to 5I are a diagram showing the localization of K17-5 cell-derived cells in fetuses which were obtained by using K17-5 cells transfected with Bcl-2-encoding gene.
Figure 5B:
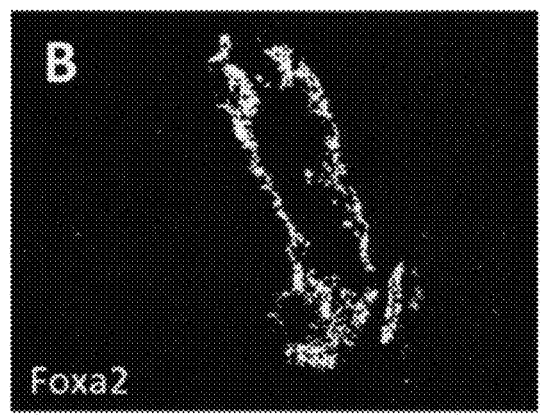
Figure 5C:
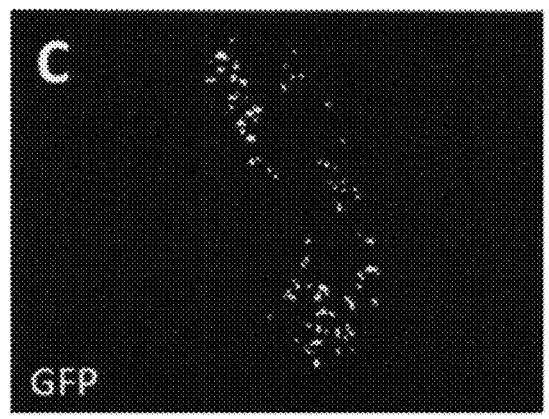
Figure 5D:
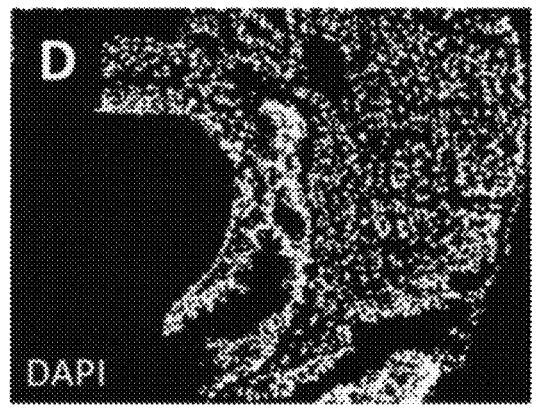
Figure 5E:
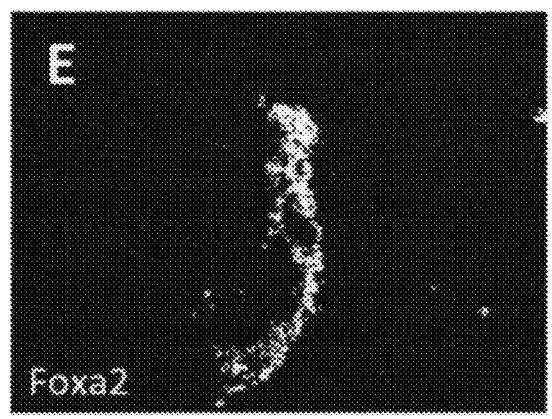
Figure 5F:
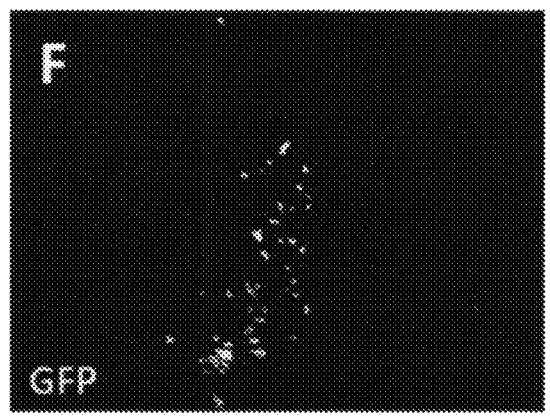
Figure 5G:
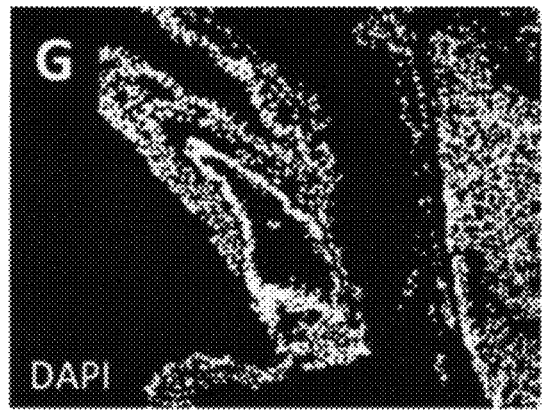
Figure 5H:
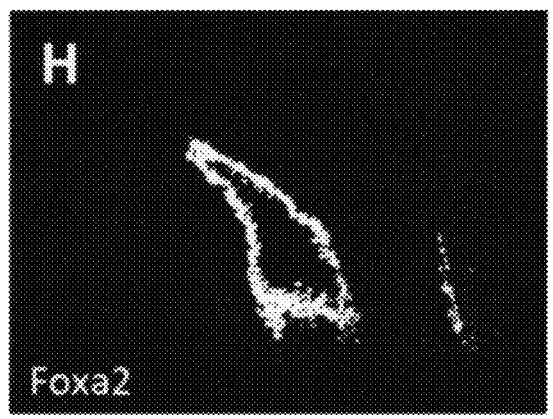
Figure 5I:
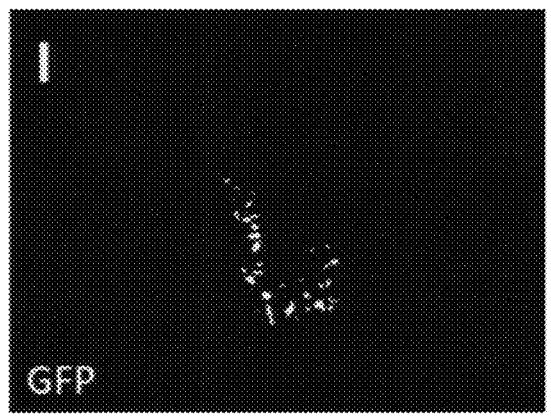

Chimeras were formed as described in Example 1A using the endodermal lineage progenitor cells. K17-5-GFP-expressing cells were used as a control. E9.5 embryos were analyzed as described in Example 1A. In the experiment using the control cells without the forced expression of Bcl-2, chimera formation was not observed (FIGS. 4A and 4B). By contrast, in the experiment using the endodermal lineage progenitor cells forced to express Bcl-2, chimera formation was observed (FIGS. 4C and 4D). In the experiment using the endodermal lineage progenitor cells forced to express Bcl-2, the rate of chimera formation was experimented three repetitive times and was consequently on the order of 9 to 58%. In the experiment using the control cells without the forced expression of Bcl-2, the rate of chimera formation was 0% (n=25).

In order to analyze in more detail the distribution of the endodermal lineage progenitor cell-derived cells in tissues, the chimeric embryos were fixed, and frozen sections were prepared and immunohistochemically stained.

For the sections, the endodermal lineage progenitor cells were stained using an anti-Foxa2 antibody (Santa Cruz Biotechnology, Inc., Sc-6554), and the introduced cells were stained using an anti-GFP antibody (Life Technologies Corp., A11122). Also, the nuclei were stained using 4',6-diamidino-2-phenylindole (DAPI). The sections were observed under a fluorescence microscope. The EGFP-positive cells were found in Foxa2-positive endodermal cells or the neighborhood thereof (FIGS. 5A to 5I). The cells were not colocalized with an ectoderm marker Tuj1 (data not shown).

These results demonstrated that: the endodermal lineage progenitor cells forced to express the Bcl-2 gene have the ability to form a chimera; and these cells form chimeras without losing their cell fate (endodermal lineage). Specifically, by use of the lineage-committed stem cells, the contribution of the introduced cells to a tissue was able to be restricted to the lineage. This means that use of the lineage-committed progenitor cells enabled preparation of chimeric animals with reduced contribution to undesired organs.

Example 4A: Study on Forced Expression of Bcl-xL Gene

In this Example, the introduction of Bcl-xL gene (GenBank Accession No. BC089016) having anti-apoptotic functions like Bcl-2, as a gene other than the Bcl-2 gene was attempted.

Figure 6A:
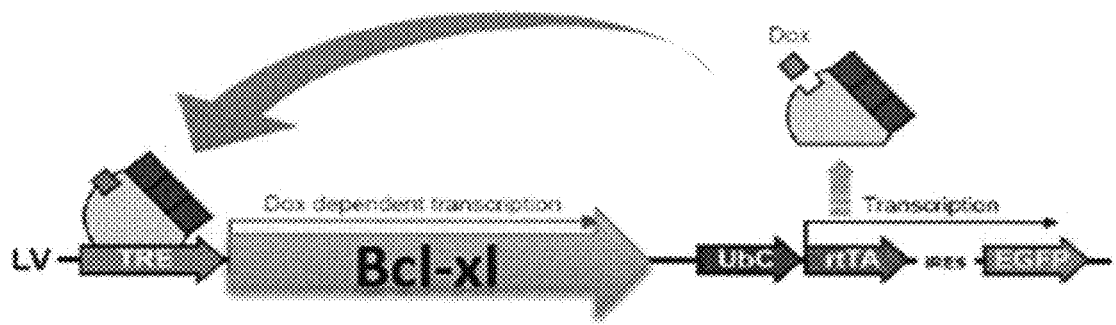
FIGS. 6A to 6E are a diagram showing the outline of a method for transfecting mouse epiblast stem cells with Bcl-xL-encoding gene (FIG. 6A) and a diagram showing optical microscopic images (FIGS. 6B and 6C) and fluorescence microscopic images (FIGS. 6D and 6E) of fetuses obtained by introduction.
Figure 6B:
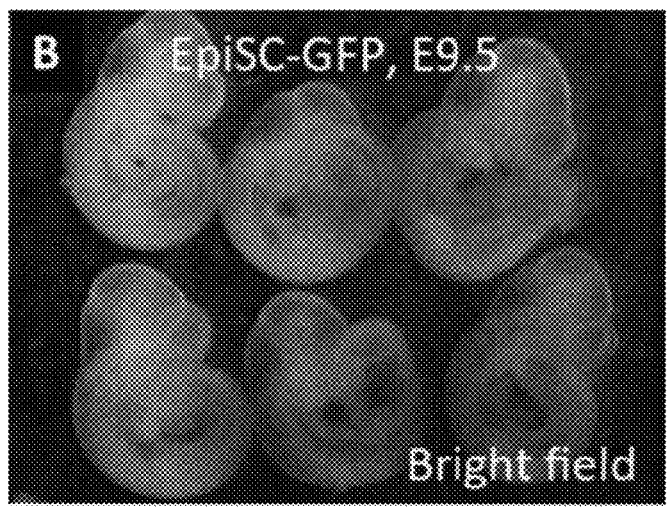
Figure 6C:
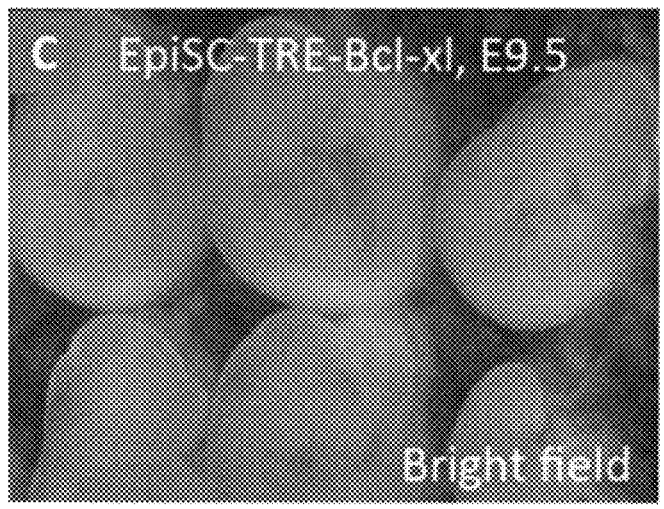
Figure 6D:
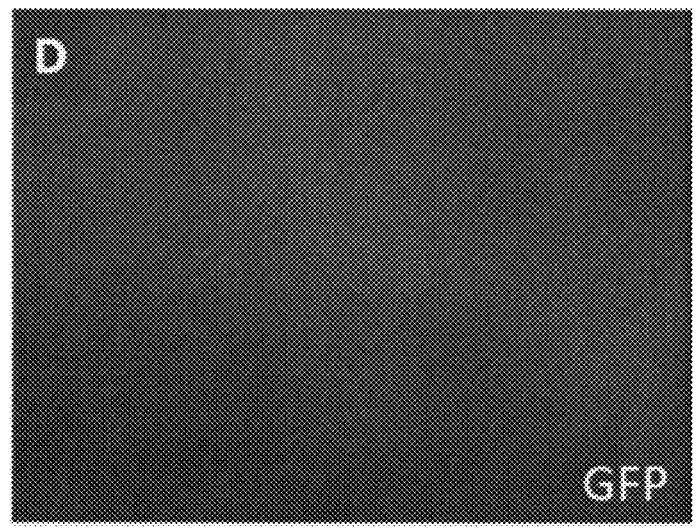
Figure 6E:

According to the method described in Example 1A, tet-on Bcl-xL AiLV vectors were constructed and introduced into EpiSC. In the same way as in Example 1A, EpiSC-TRE-Bcl-xL cells were obtained with the expression of EGFP as an index (FIG. 6A). EpiSC transfected with EGFP expression lentivirus vectors having the EGFP gene linked to CAG promoter was used as a control. The cells were introduced to mouse blastocysts, which were then transplanted into the uteri of recipient mice as described in Example 1A. E9.5 embryos were recovered and observed under a fluorescence microscope. As a result, EpiSC without the expression of Bcl-xL formed no chimera, whereas EpiSC expressing Bcl-xL was shown to form complete chimeras (FIGS. 6B to 6E).

These results demonstrated that the ability to form a chimera can be imparted to EpiSC by the suppression of apoptosis.

The developmental stage of mammalian pluripotent stem cells is known to correspond to the developmental stage of rodent EpiSC. Hence, the present invention created a path toward the efficient preparation of chimeric animals using mammalian pluripotent stem cells.

This means that even in the case of using pluripotent stem cells such as rodent EpiSC or non-rodent mammalian primed ES cells or iPS cells, preparation of genetically modified animals or efficient organ regeneration by blastocyst complementation (e.g., WO2008/102602) can be achieved.

Example 5A: Gene Expression Analysis of EpiSC Treated for Suppression of Apoptosis In Examples 2A to 4A, the cells treated for the suppression of apoptosis had the improved ability to form a chimera. In this Example, the gene expression of EpiSC treated for the suppression of apoptosis was analyzed and compared with the gene expression of EpiSC and ES cells.

EB3DR-EpiSC-TRE-Bcl-2 prepared as described in Example 2A was treated with 1 µg/mL doxycycline for 24 hours or longer to allow EpiSC to express Bcl-2.

On the basis of the gene expression data of EB3DR-EpiSC and the gene expression data (GSE7866) of mouse EpiSC and ESC reported by Tesar et al., Nature (2007), 448 (7150): 196-199 in Example 1A, the gene expression profiles of the EpiSC-A and EpiSC-A-TRE-BCL2 lines established in Example 1A were exhaustively compared to conduct cluster analysis. The cluster analysis of the gene expression profiles was conducted using EB3DR-EpiSC and 3 mouse ES cell lines (mES_ESF58/1, mES_ESF175/1, and mES_ESF122) as comparative controls.

The gene expression profiling was conducted as follows: first, total RNA was extracted from EpiSC-A or EpiSC-A-TRE-BCL2 under each condition (i.e., the cells treated with doxycycline, the cells 24 hours after removal of doxycycline, or the cells 48 hours after removal of doxycycline) using RNeasy mini kit (manufactured by Qiagen N.V.). This RNA (100 ng) was used as a template according to the protocol of the one-color method recommended by Agilent Technologies Inc. to obtain labeled cRNA. This cRNA was hybridized to a microarray chip Agilent-014868 Whole Mouse Genome Microarray 4×44K (Agilent Technologies Inc., G4122F) and scanned using Agilent DNA microarray scanner. The obtained data was normalized among arrays and thereby allowed to be compared with GSE7866. The analysis employed Genespring GX 11.5.1 (Agilent Technologies Inc.). Gene groups that differed in expression level by 10 or more times between the GSE7866 gene expression data set (mES_ESF58/1, mES_ESF175/1, and mES_ESF122; in FIG. 7, corresponding to mESC-1, mESC-2, and mESC-3) of the mouse ES cells and the gene expression data set (EpiSC-5, EpiSC-7_P20, and EpiSC-7_P25; in FIG. 7, corresponding to mEpiSC-1, mEpiSC-2, and mEpiSC-3) of the mouse EpiSC were subjected to cluster analysis among GSE7866, and EpiSC-A and EpiSC-A-TRE-BCL2 under each condition.

Figure 7:
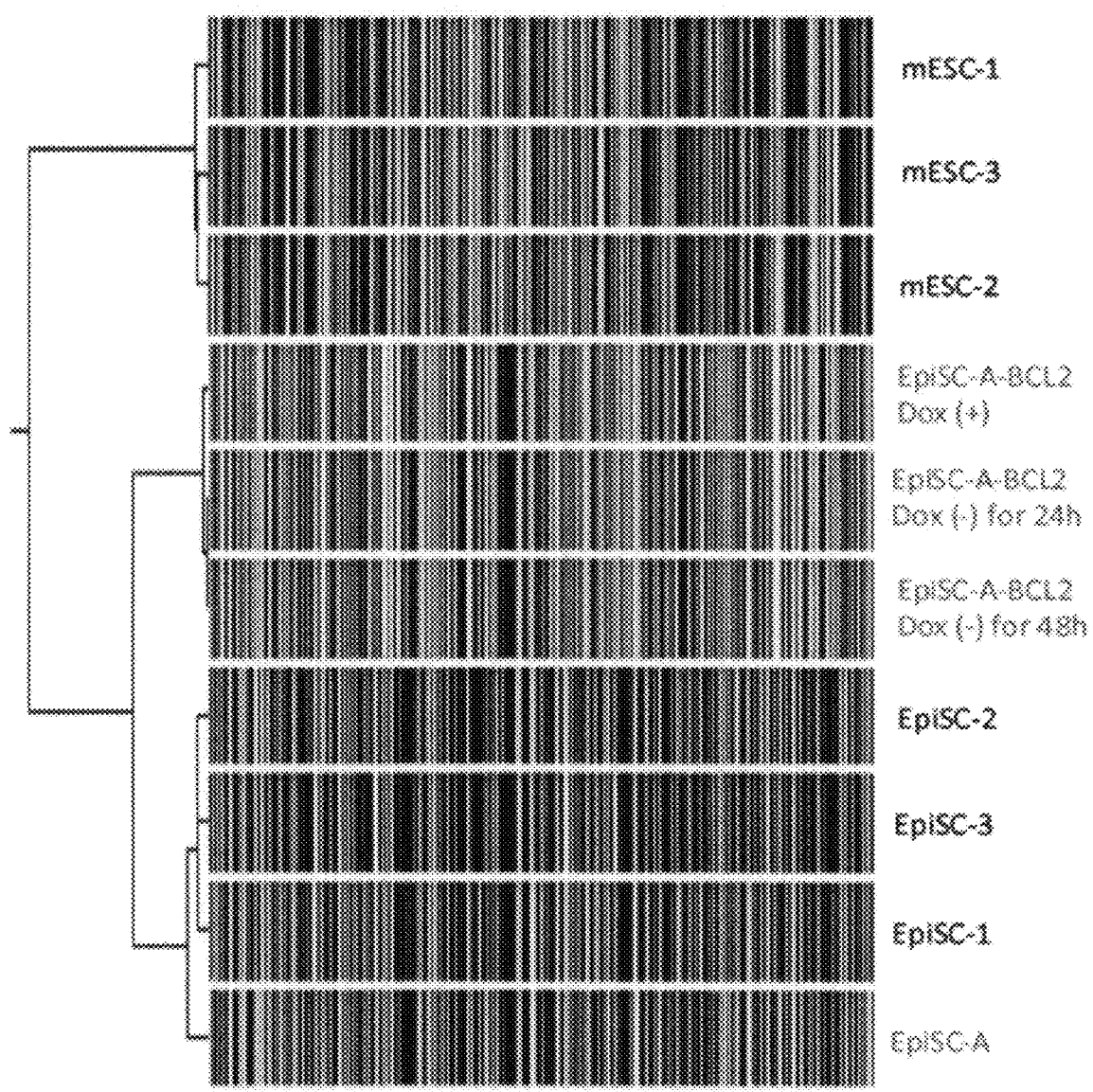
FIG. 7 shows results of cluster analysis of the gene expression profile of EpiSCs forced to express Bcl-2 and the gene expression profiles of EpiSCs and ES cells.

As a result, EB3DR-EpiSC-TRE-Bcl-2 forced to express Bcl-2 was classified into a cluster different from that of EB3DR-EpiSC (FIG. 7). The expression of Bcl-2 was leaked even in EB3DR-EpiSC-TRE-Bcl-2 cultured in the absence of doxycycline, demonstrating that the introduction of BCL2 is more influential than the presence of doxycycline and shifts the gene expression pattern of EpiSC to the ES cell side (FIG. 7).

Figure 8:
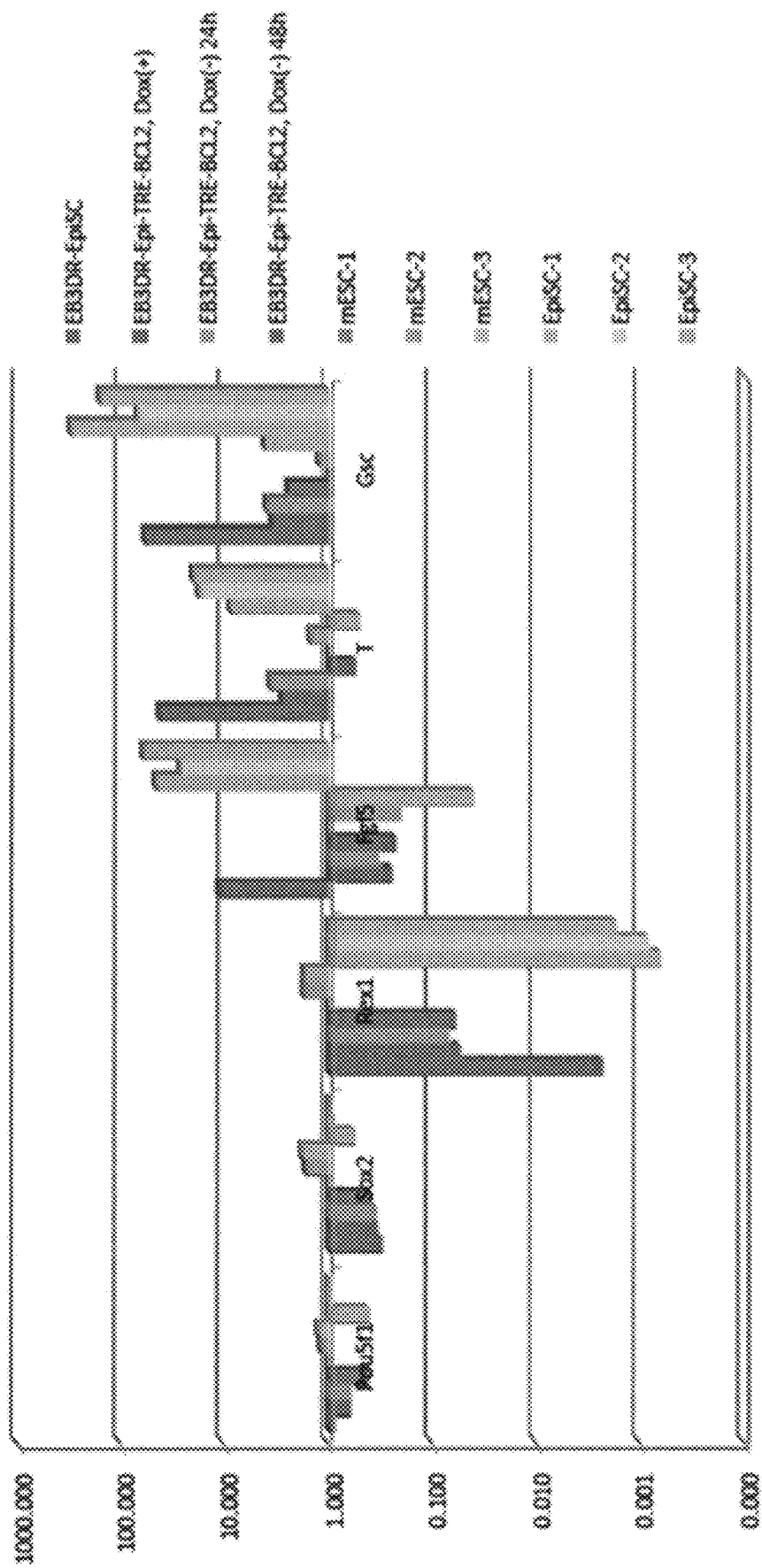
FIG. 8 is a diagram showing in more detail the expression levels of 6 genes in ES cells, EpiSCs, and EpiSCs forced to express Bcl-2.

Next, the genes to be compared were narrowed down to six, and the detailed expression levels of these genes were compared (Table 1 and FIG. 8).

TABLE 1

Comparison of gene expression level among EpiSC, ES cell, and EB3DR-EpiSC-TRE-Bcl-2

| Name of gene | EpiSC-A | EpiSC-A-BCL2. Dox(+) | EpiSC-A-BCL2. Dox(−) for 24 h | EpiSC-A-BCL2. Dox(−) for 48 h | mESC-1 | mESC-2 | mESC-3 | EpiSC-1 | EpiSC-2 | EpiSC-3 |
|---|---|---|---|---|---|---|---|---|---|---|
| Pou5f1 | 16.597 | 11.677 | 11.564 | 8.004 | 19.418 | 22.943 | 24.339 | 7.769 | 18.553 | 18.865 |
| Sox2 | 2.744 | 3.051 | 3.113 | 3.520 | 9.018 | 15.030 | 16.351 | 5.014 | 7.884 | 8.225 |
| Rex1 | 0.113 | 2.666 | 3.432 | 2.936 | 49.103 | 86.709 | 84.688 | 0.032 | 0.042 | 0.085 |
| Fgf5 | 8.228 | 0.178 | 0.237 | 0.164 | 0.725 | 0.145 | 0.029 | 33.789 | 19.478 | 45.418 |
| T | 6.722 | 0.442 | 0.578 | 0.085 | 0.155 | 0.238 | 0.078 | 1.375 | 2.772 | 3.164 |
| Gsc | 4.437 | 0.263 | 0.296 | 0.183 | 0.073 | 0.094 | 0.307 | 23.342 | 5.229 | 12.206 |

As shown in Table 1 and FIG. 8, EB3DR-EpiSC-TRE-Bcl-2 forced to express Bcl-2 exhibited intermediate values for Rax1, Fgf5, T, and Gsc, etc., between the values of EpiSC and ES cells. This suggested that EpiSC was rendered more undifferentiated by the forced expression of Bcl-2.

Figure 9:
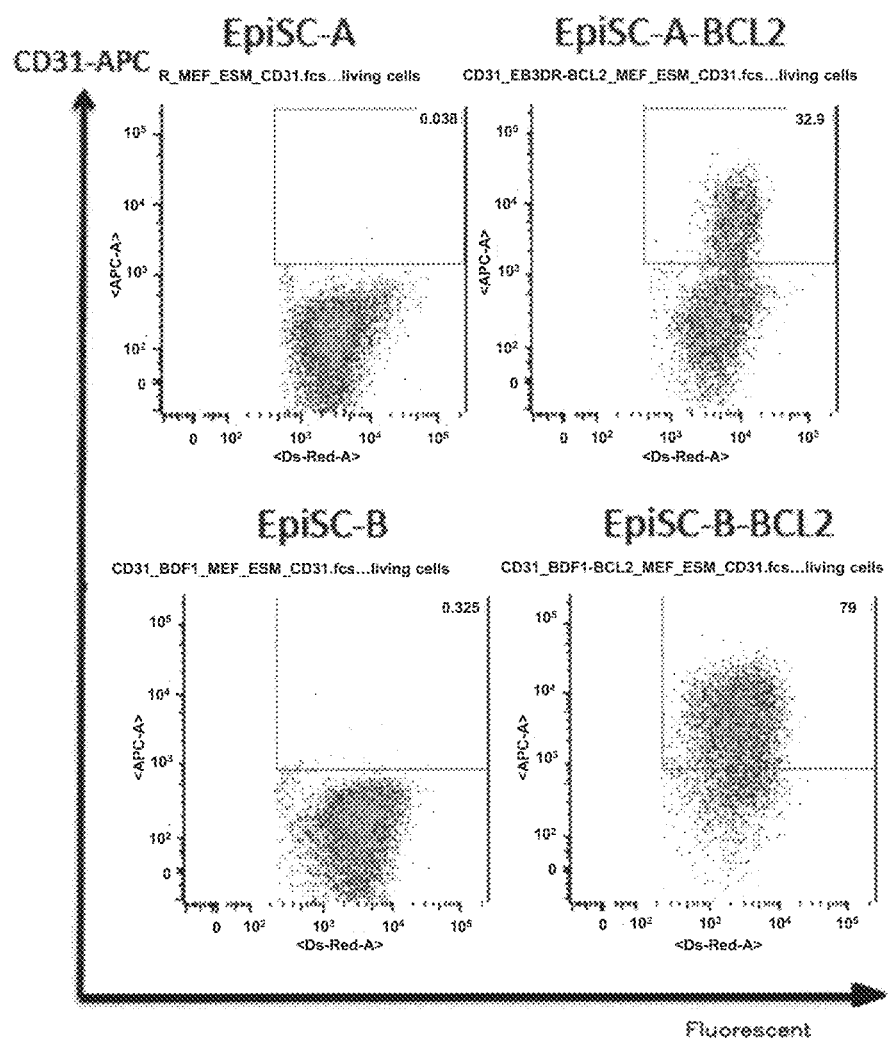
FIG. 9 is a diagram showing results of quantifying the expression of CD31 using FACS as to two types of EpiSC lines forced to express Bcl-2.

EpiSC after the forced Bcl-2 expression was further analyzed for the expression of CD31 (PECAM1). CD31 is a cell surface marker known to be expressed on ES cells but not expressed on EpiSC. The expression level of CD31 was confirmed by FACS using an APC-conjugated rat anti-mouse CD31 antibody (manufactured by eBioscience, Inc., 17-0311). As a result, two types of EpiSC cells (EpiSC-A and -B) forced to express Bcl-2 were both confirmed to include cells highly expressing CD31 (FIG. 9). This demonstrated that EpiSC forced to express Bcl-2 biochemically exhibits the features of ES cells.

Figure 10A:
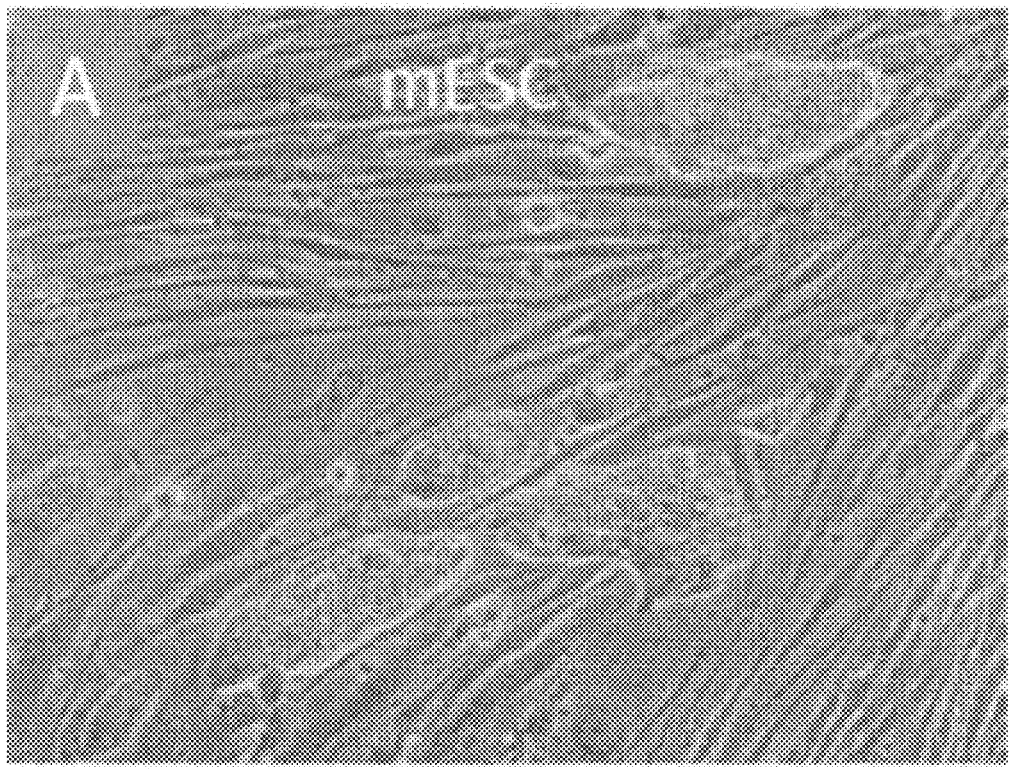
FIGS. 10A to 10D are a diagram showing the shape of colonies formed by highly CD31-expressing cells (cells within the frames of FIG. 9) which were isolated from EpiSCs forced to express Bcl-2 and then adherent-cultured.
Figure 10B:
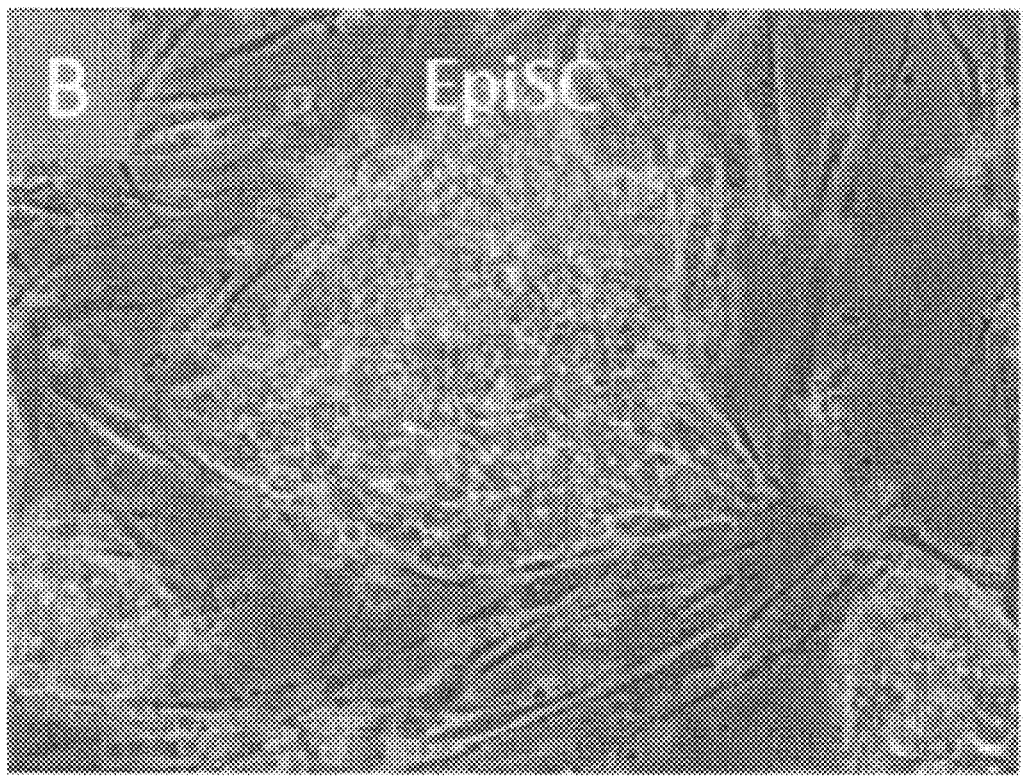
Figure 10C:
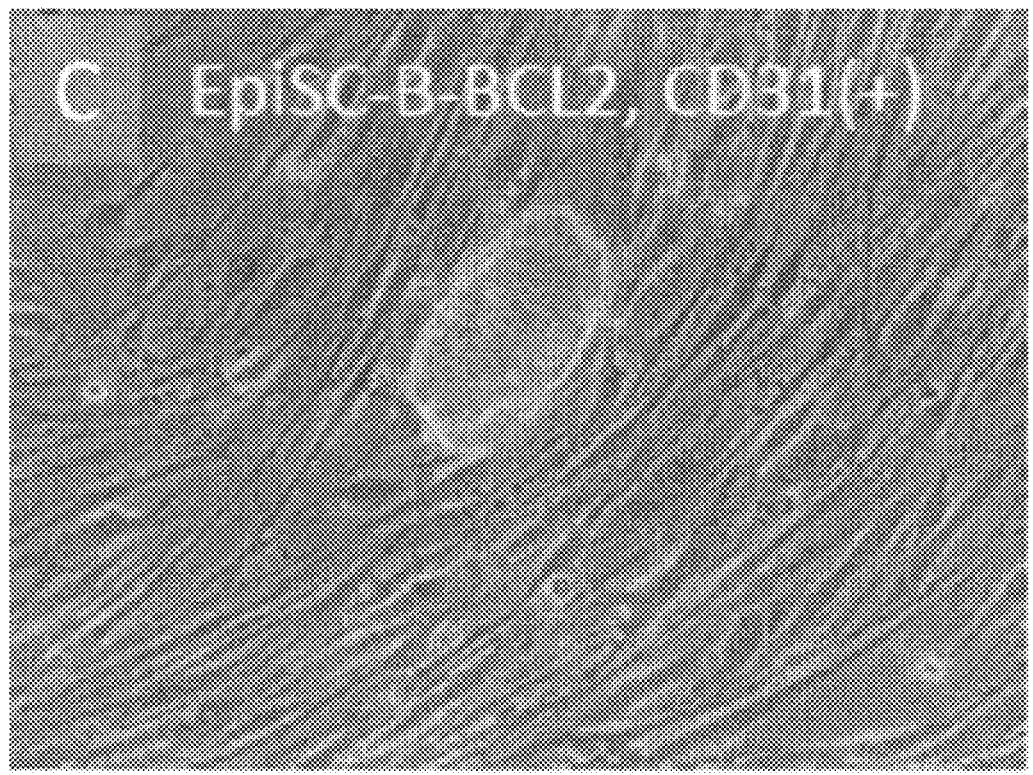
Figure 10D:
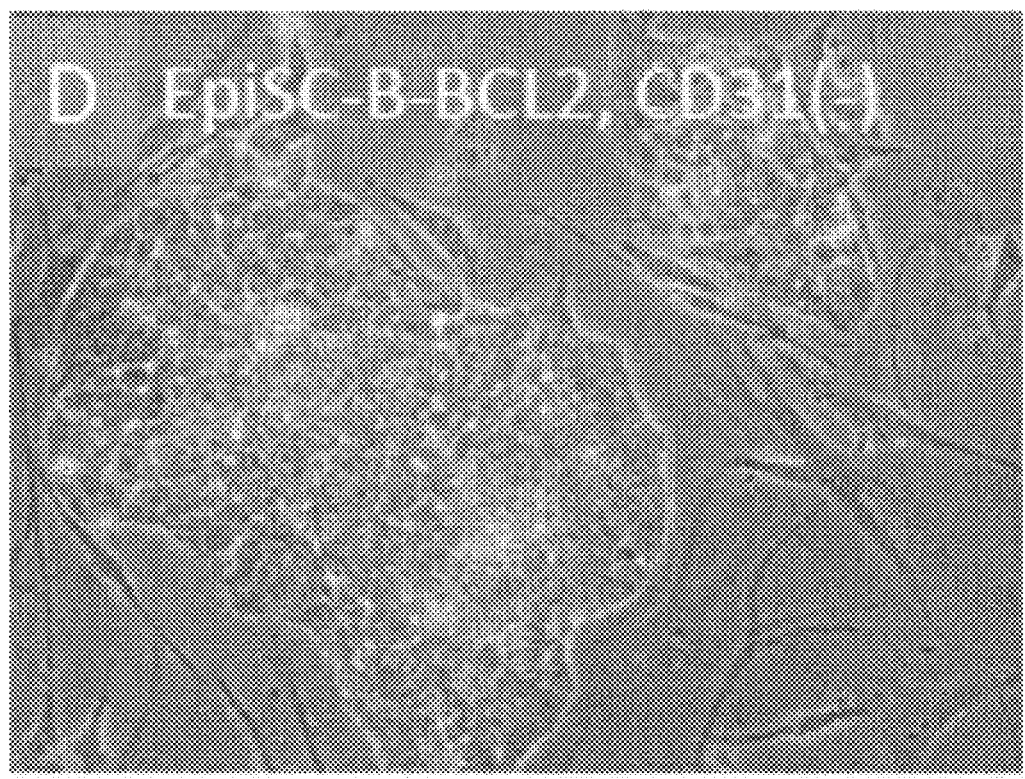

CD31-expressing EpiSC was further selected (within the frames of FIG. 9) by FACS using an APC-conjugated rat anti-mouse CD31 antibody (manufactured by eBioscience, Inc., 17-0311) and adherent-cultured in the aforementioned medium for EpiSC. Two days after the culture, the cells formed steric colonies having few cytoplasms and obscure boundaries between cells (FIG. 10C). This colony morphology is morphology characteristic of colonies formed by ES cells (FIGS. 10A and 10C). EpiSC and EpiSC negative to CD31 in spite of the forced expression of Bcl-2 formed flat colonies with relatively many cytoplasms (FIGS. 10B and 10D). These results demonstrated that among the cells forced to express Bcl-2, the highly CD31-expressing cells physiologically exhibit the features of ES cells.

Among the cells forced to express Bcl-2, the highly CD31-expressing cells were altered to pluripotent stem cells capable of forming multi-layer colonies in adherent culture, suggesting the possibility that the cells were reprogrammed to ES cells (i.e., naïve pluripotent stem cells).

Example 1B: Chimeric Animal Preparation by Transfer of Apoptosis-Suppressing Factor In Examples above, Bcl-2 or Bcl-xL was used as the apoptosis-suppressing factor. In this Example, cells were further forced to express Xiap and crmA as apoptosis-suppressing factors and examined for their ability to form a chimera.

The Xiap used was mouse Xiap, and the crmA used was cowpox virus-derived crmA. According to the method described in Example 1, tet-on Xiap AiLV vectors or tet-on crmA AiLV vectors were constructed and each transferred to EpiSC or endodermal lineage progenitor cells prepared in Example 3A. In order to elucidate the effects of these introduced apoptosis-suppressing factors, these cells were each compared with untreated cells (i.e., EpiSC or endodermal lineage progenitor cells before the gene transfection).

Figure 11A:
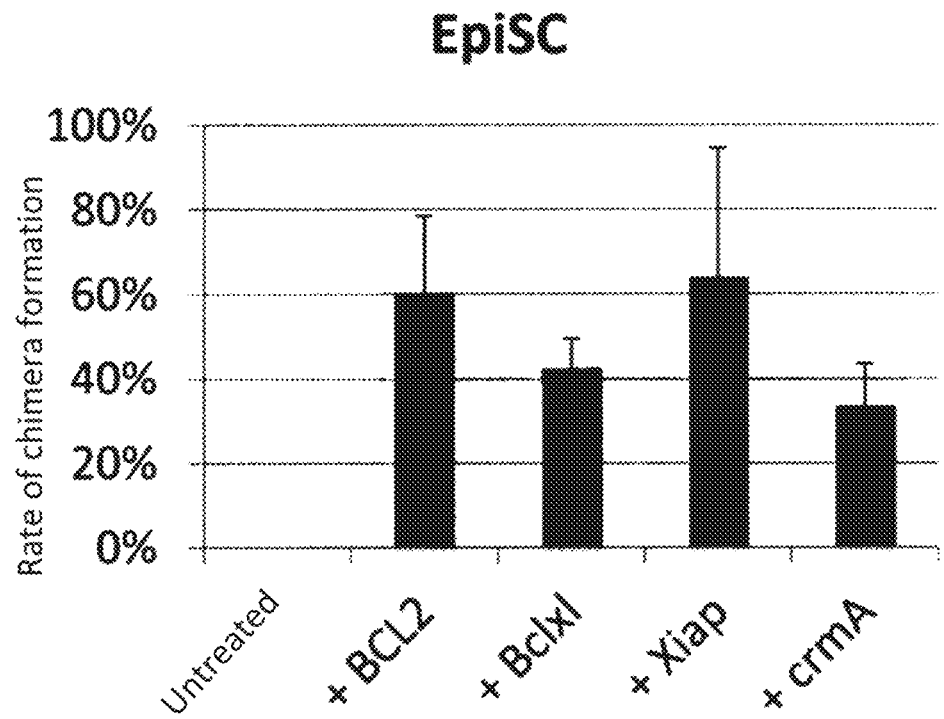
FIGS. 11A to 11F are a diagram showing the rates of chimera formation of cells obtained by the forced expression of an apoptosis-suppressing factor Xiap or crmA.
Figure 11B:
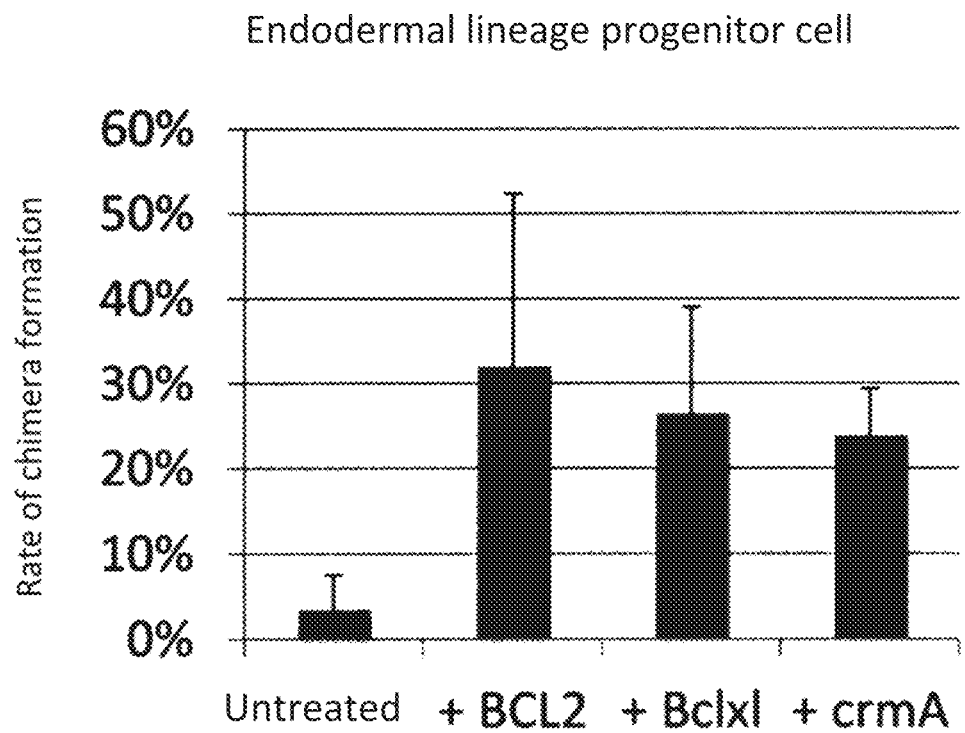
Figure 11C:
Figure 11D:
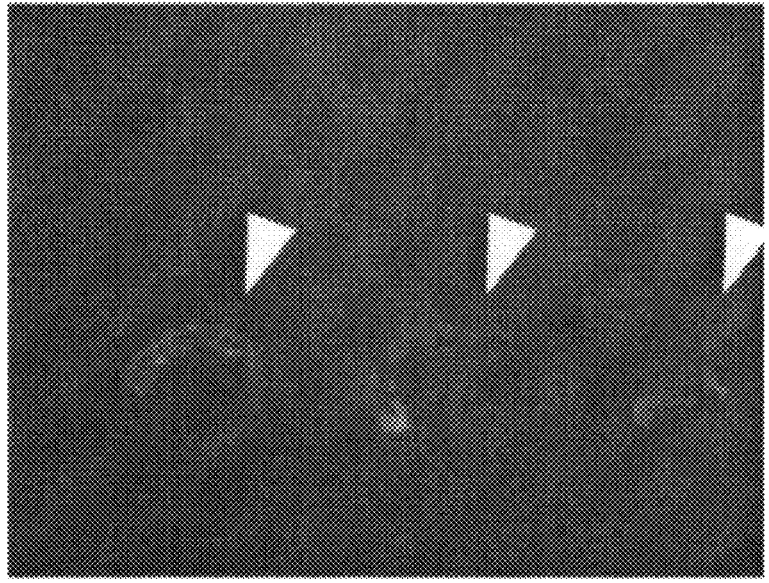
Figure 11E:
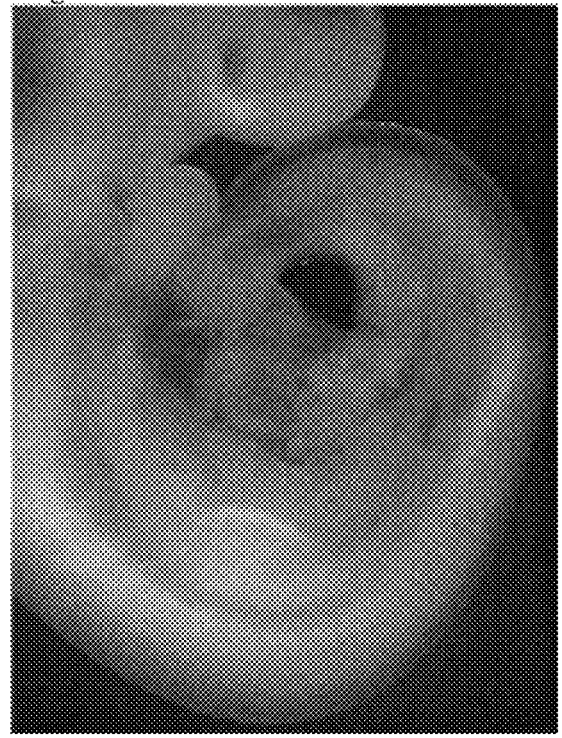
Figure 11F:
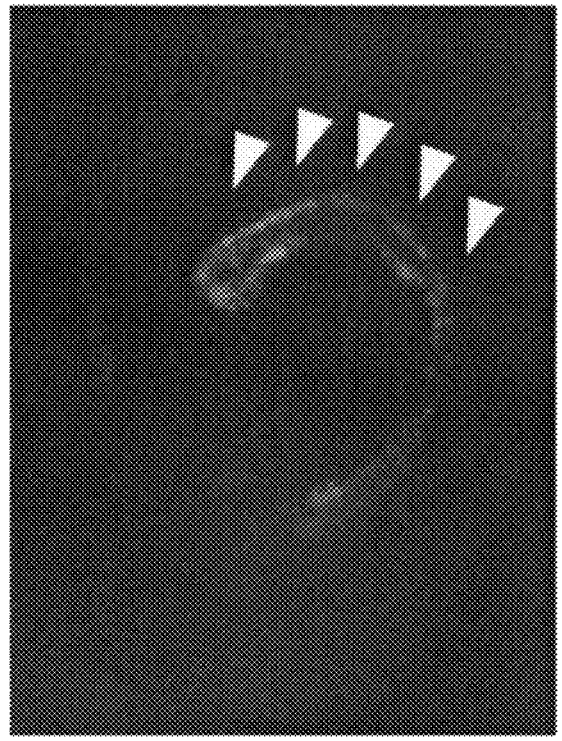

Results of confirming their respective rates of chimera formation were as shown in FIGS. 11A and 11B. As shown in FIGS. 11A and 11B, the cells induced with either of the apoptosis-suppressing factors had the largely improved ability to form a chimera. Unexpectedly, the untreated cells were able to contribute to chimeric animals, though these cells were considered to have no ability to form a chimera. The cells having the contribution among the untreated cells were also restricted to the endodermal lineage (FIGS. 11C to 11F).

From these results, the apoptosis suppression treatment was able to be further confirmed to improve the ability of the cells to form a chimera. Unexpectedly, the aforementioned cells heretofore believed to have no ability to form a chimera were shown to have the ability to form a chimera, regardless of the presence or absence of the apoptosis suppression treatment. The forced expression of Bcl-2, Bcl-xL, or crmA in the endodermal lineage progenitor cells were reconfirmed to improve their ability to form a chimera and allow the endodermal lineage progenitor cells to form chimeras without losing their cell fate.

It has heretofore been known that very limited types of cells have the ability to form a chimera, and some pluripotent stem cells have no ability to form a chimera. Cells such as tissue stem cells, tissue progenitor cells, somatic cells, or germ cells are at a more advanced developmental stage than that of pluripotent stem cells and therefore supposed to have no ability to form a chimera. Nonetheless, the experiments conducted here revealed that the endodermal lineage progenitor cells, which are tissue progenitor cells and are lineage-committed progenitor cells, have the ability to form a chimera, albeit at a low rate.

Since the ability to form a chimera is lost with advances in the developmental stage, the primed pluripotent stem cells or the tissue stem cells, which are cells at an earlier developmental stage than that of the endodermal lineage progenitor cells, probably also have the ability to form a chimera. In addition, the somatic cells or the germ cells probably also have the ability to form a chimera.

Example 2B: Chimeric Animal Preparation by Introduction of Cell Death-Resistant Epiblast Cell In Example 1B, the endodermal lineage progenitor cells contributed to chimeras, albeit at a low rate, even without apoptosis suppression treatment. In this Example, in order to confirm whether similar results were obtained for epiblast stem cells, the ability of the epiblast stem cells to form a chimera was verified in the absence of the apoptosis suppression treatment.

EpiSC-tdT was prepared, maintained, and cultured in the same way as in Example 1A, and the resulting line (hereinafter, referred to as "EpiSC-sub") was introduced to embryos without being subjected to apoptosis suppression treatment, to form chimeras.

Figure 12A:
FIGS. 12A and 12B show the results of forming chimeras when pluripotent stem cells having the ability to form a colony after being dispersed into single cells were used as cells to be introduced into an embryo.
Figure 12B:
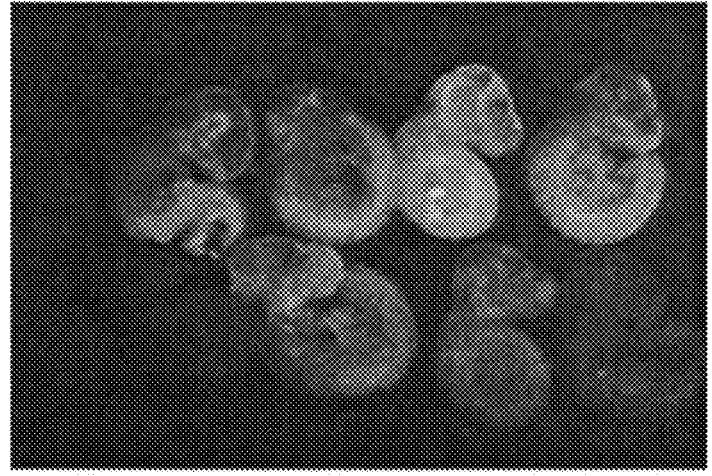

Specifically, EpiSC-sub was introduced to mouse blastocysts by the method described in Example 1 to confirm whether or not to form chimeric individuals. Surprisingly, the EpiSC-sub-introduced embryos produced chimeric animals, albeit at a low rate (FIGS. 12C and 12D). The rate of chimera formation was approximately 10%.

The cell death resistance of EpiSC-sub was verified. Pluripotent stem cells are known to be killed due to cell death when dispersed into single cells (Ohgushi M. et al., Cell Stem Cell, 7: 225-239, 2010). Accordingly, EpiSC-sub was dispersed into single cells, and the cells were then adherent-cultured to confirm the rate of colony formation.

Specifically, first, EpiSC-sub and mEpiSC-B (control) were each treated with trypsin and thereby dispersed into single cells. Then, the cells were seeded at 1 cell/well to a MEF feeder-coated 96-well plate using a cell sorter FACS Aria (manufactured by Becton, Dickinson and Company). After culture for 7 to 10 days, the number of wells confirmed to contain formed colonies was counted to determine the rate of colony formation. As a result, EpiSC-sub exhibited a high rate of colony formation (approximately 65%). This experiment revealed that EpiSC-sub is cell death-resistant EpiSC. On the other hand, EpiSC-A and EpiSC-B were hardly found to have the ability to form a colony after being dispersed into single cells, and did not exhibit the ability to form a chimera.

Example 2B demonstrated that the epiblast stem cells include those having high ability to form a chimera. These results also demonstrated that in the case of using cells having the ability to form a colony after being dispersed into single cells (i.e., using cell death-resistant cells), the cells contribute to chimera formation even without apoptosis suppression treatment. The enhanced cell death resistance of the cells seemed to be able to improve the ability of the cells to form a chimera.

Example 3B: Chimeric Animal Preparation by Introduction of Primordial Germ Cell In this Example, whether or not chimeras could be prepared by the cell death suppression of primordial germ cells, as with the endodermal progenitor cells, was verified. The contribution of introduced primordial germ cells to germ cells was further confirmed in the chimeras.

Figure 13A:
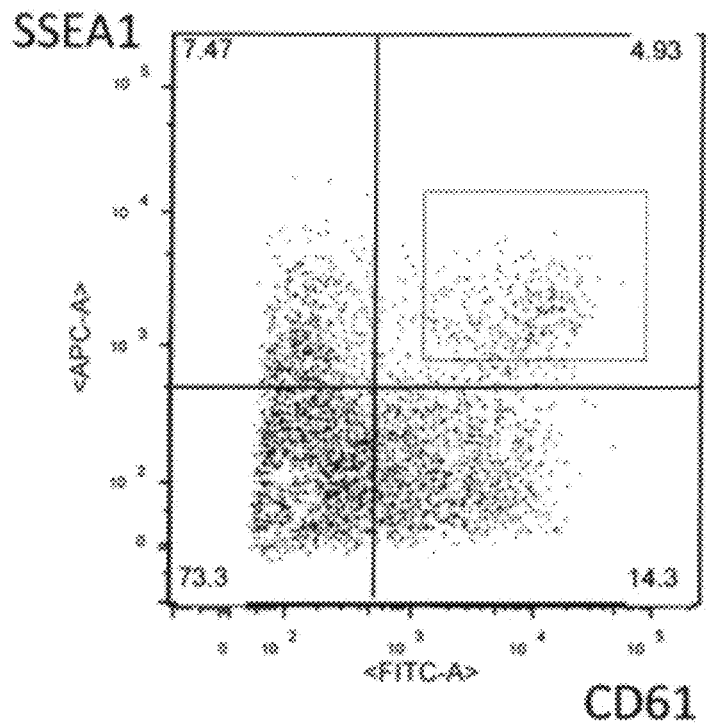
FIGS. 13A to 13I are a diagram showing the preparation of primordial germ cells by apoptosis suppression treatment and the ability of the primordial germ cells to form a chimera.

First, we infected mouse ES cells by Tet-on AiLV expressing the Bcl-2 gene as described in Example 1A to prepare BCL2-inducible mouse ES cells. Next, prior to the induction of differentiation, the cells were transfected with vectors containing tdTomato gene operably linked to CAG promoter (CAG-tdTomato vectors) and thereby fluorescently labeled. Then, the differentiation of normal ES cells or the BCL2-inducible mouse ES cells into primordial germ cell-like cells (PGCLC) was induced. The conditions for the induction of differentiation into PGCLC were set to the differentiation conditions described in Hayashi et al., Cell, 2011. Prior to the induction of differentiation, these cells were labeled with the lentivirus vectors for the constitutive expression of tdTomato under the control of CAG promoter. After the induction of differentiation, cells coexpressing SSEA-1 and CD61 were separated as primordial germ cells using a cell sorter (FIG. 13A, broken-lined).

Figure 13B:
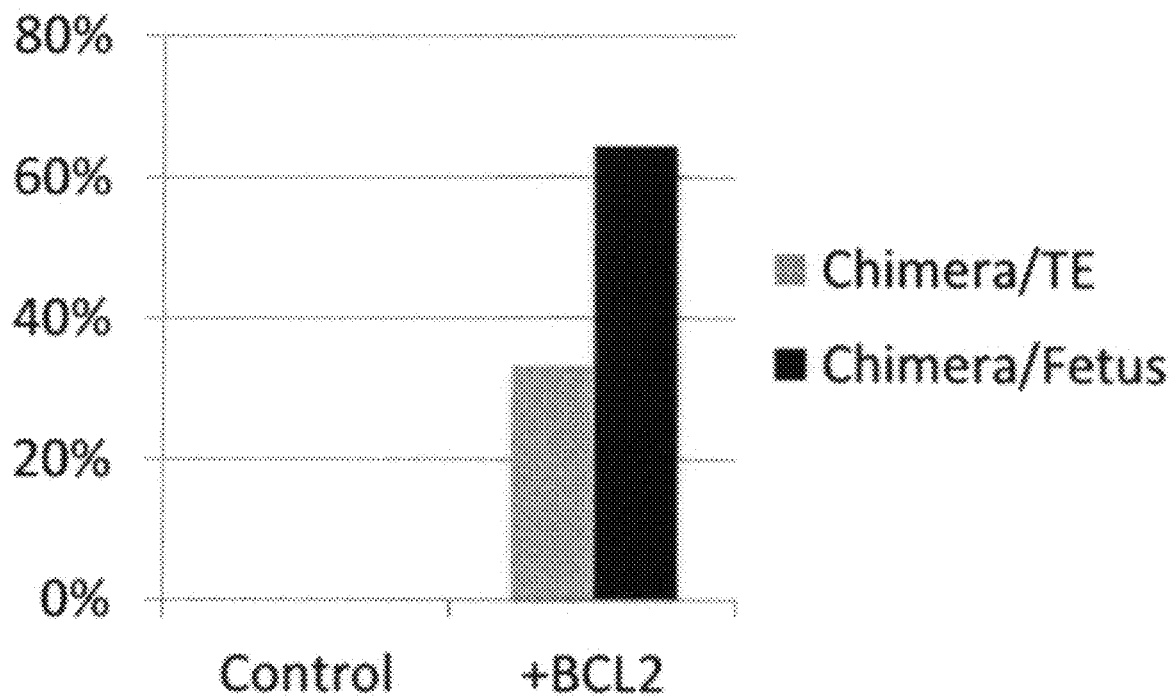
Figure 13C:
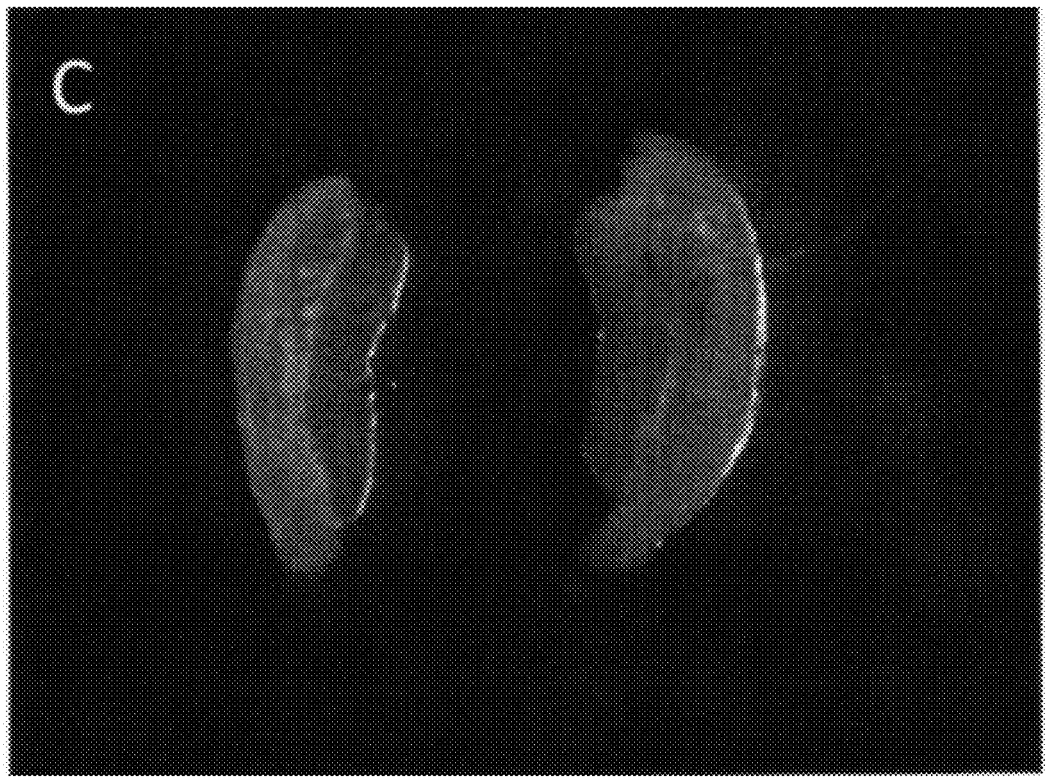
Figure 13D:
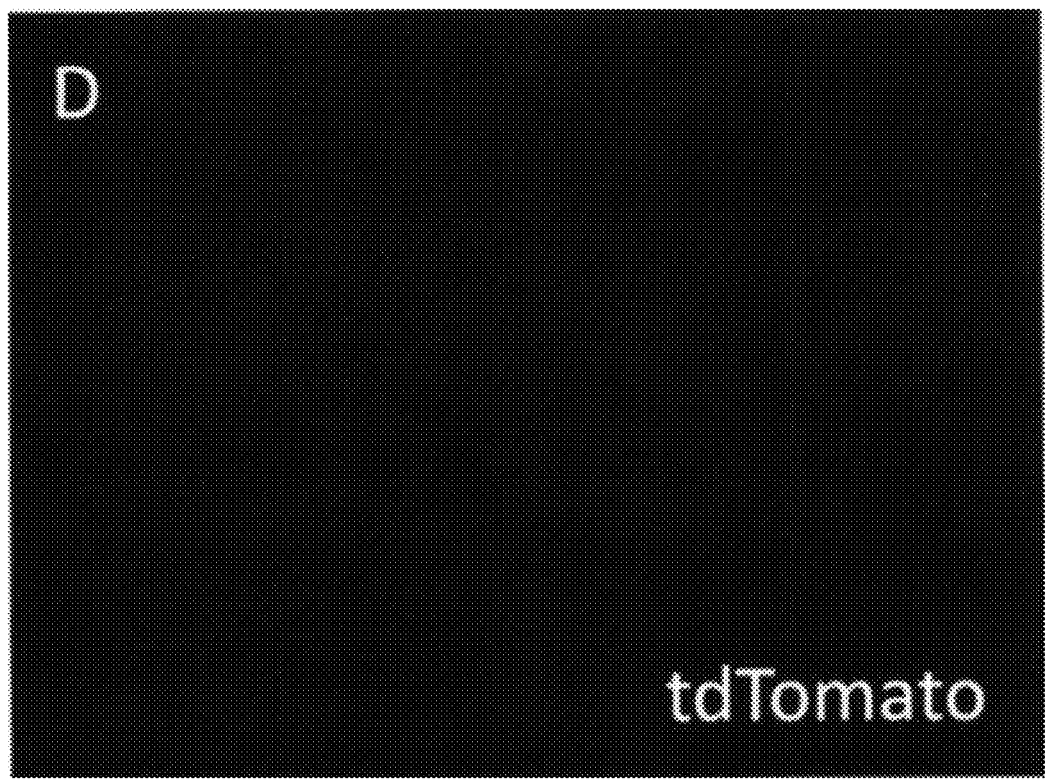
Figure 13E:
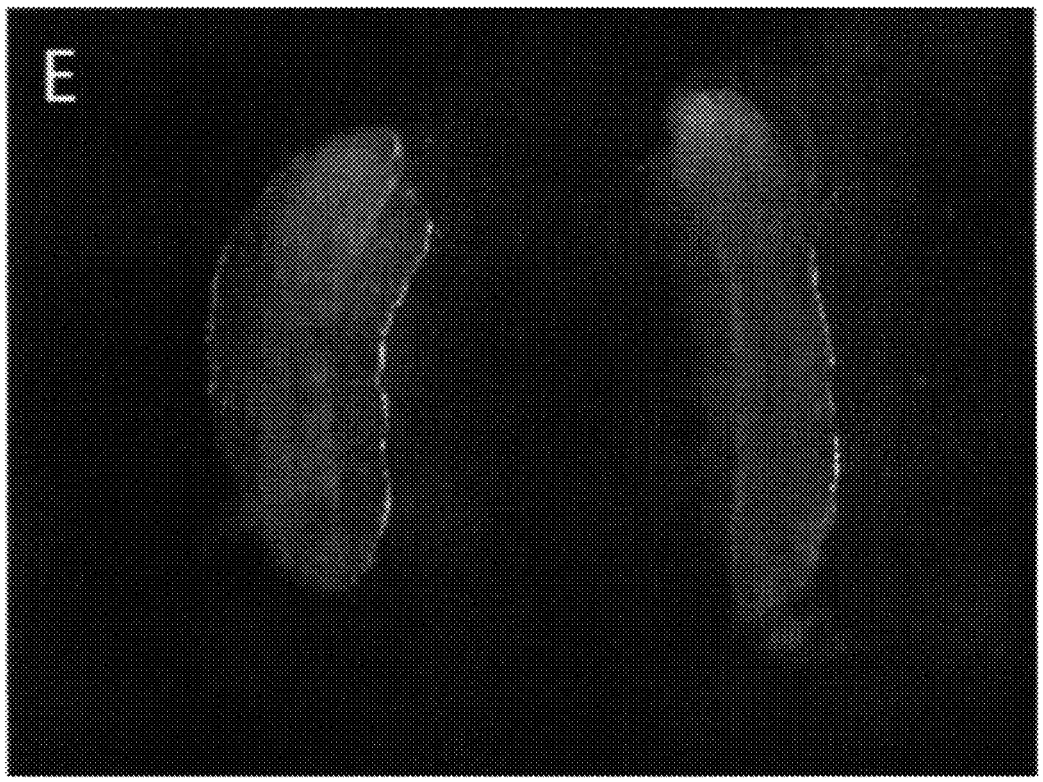
Figure 13F:
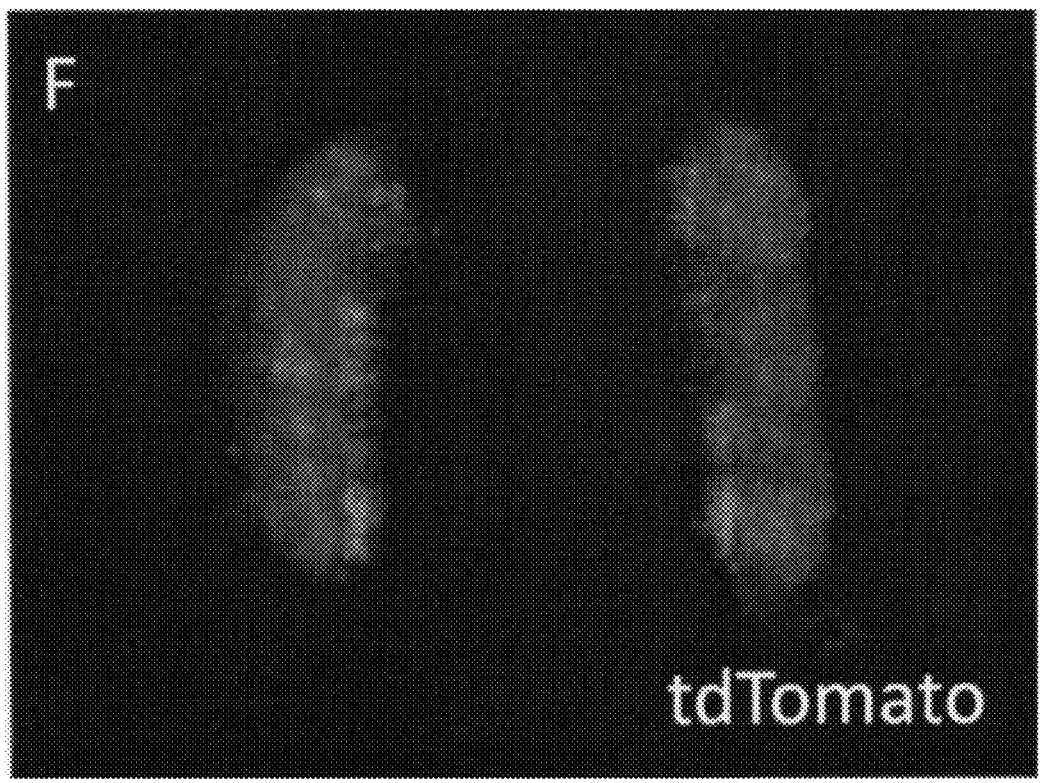
Figure 13G:
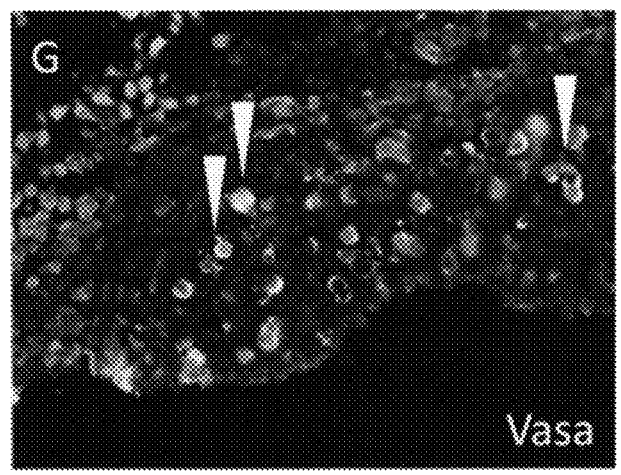
Figure 13H:
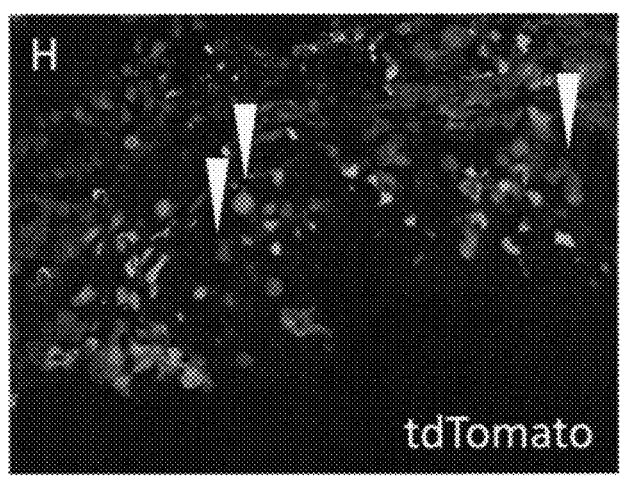
Figure 13I:
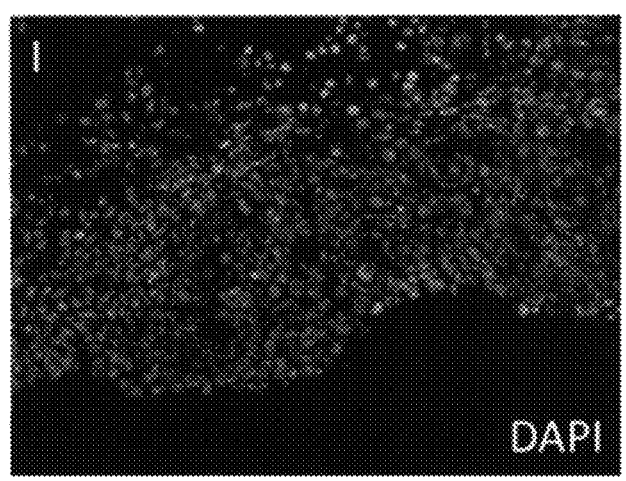
Figure 14A:
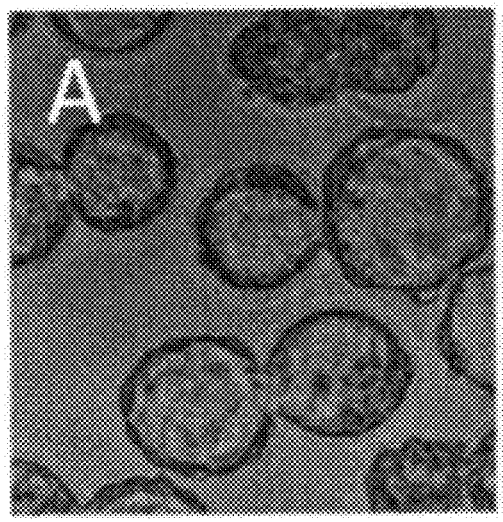
FIGS. 14A to 14N are a diagram showing results of observing chimera formation after introduction of human induced pluripotent stem cells (hiPS cells) to mouse embryos. Bcl-2(+) represents that the cells were forced to express Bcl-2. Bcl-2(−) represents control cells.
Figure 14B:
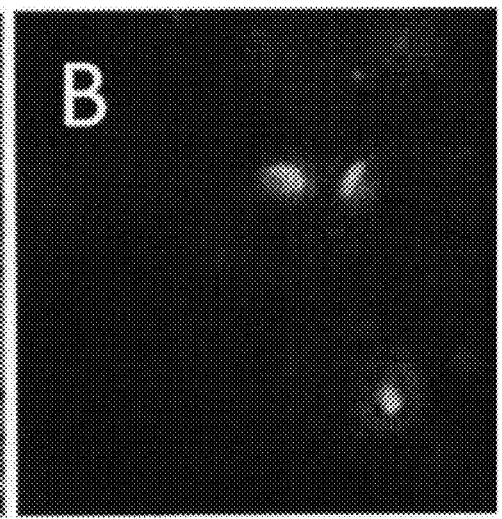
Figure 14C:
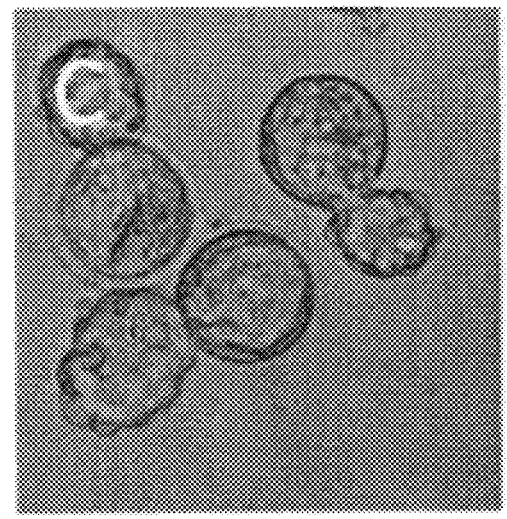
Figure 14D:
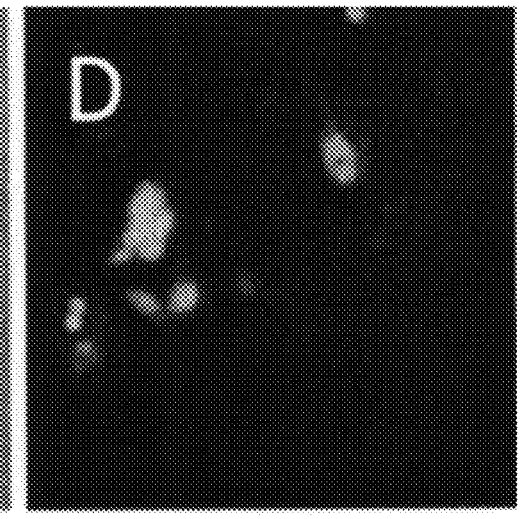
Figure 14E:
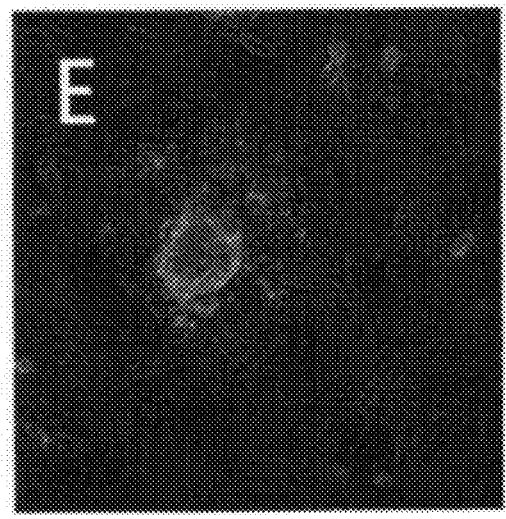
Figure 14F:
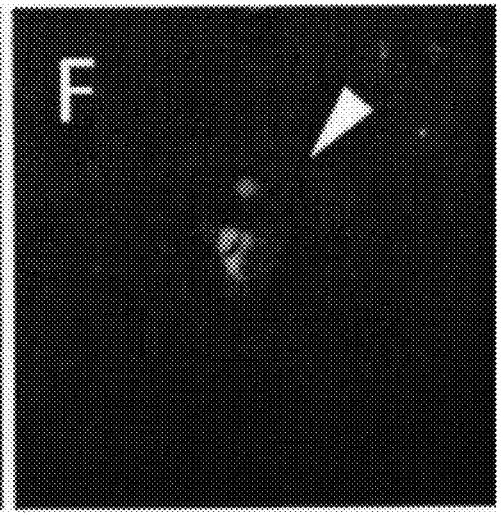
Figure 14G:
Figure 14H:
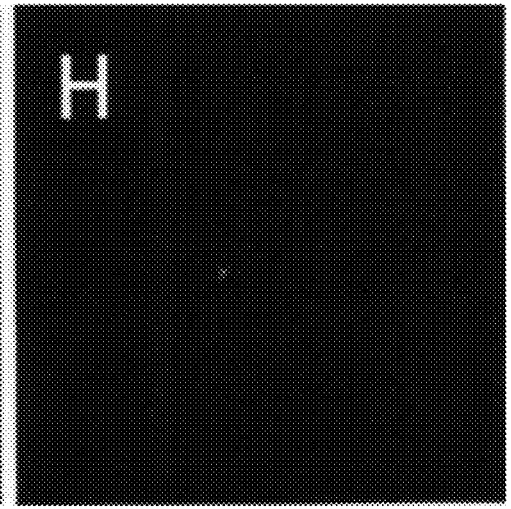
Figure 14I:
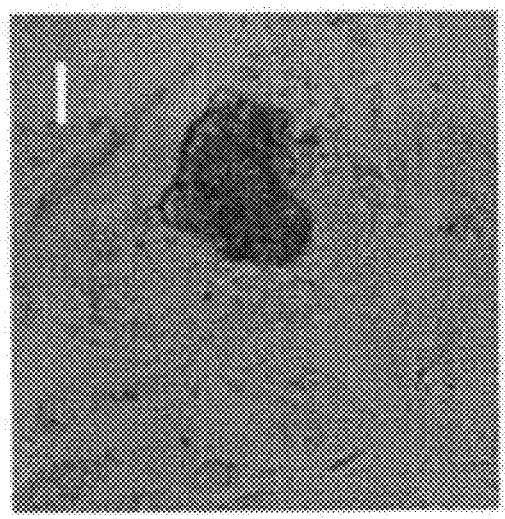
Figure 14J:
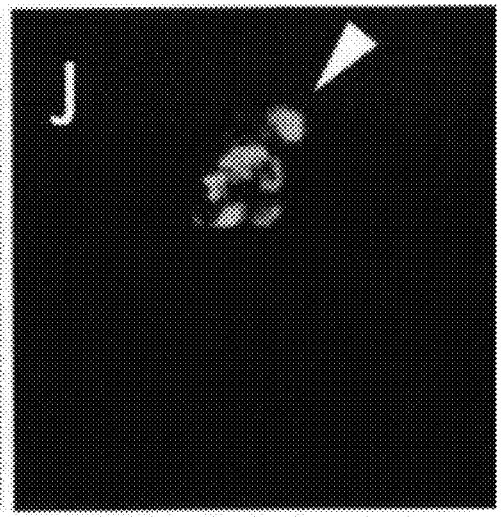
Figure 14K:
Figure 14L:
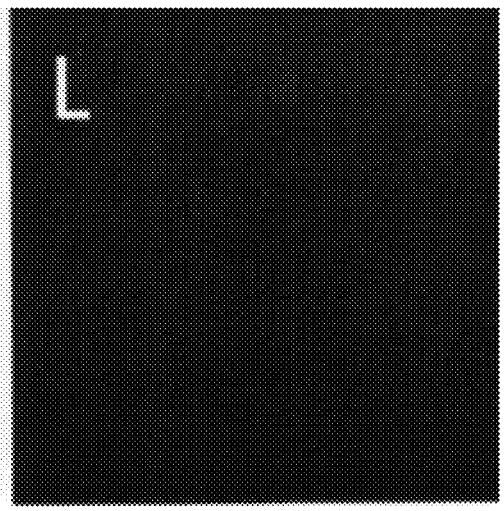
Figure 14M:
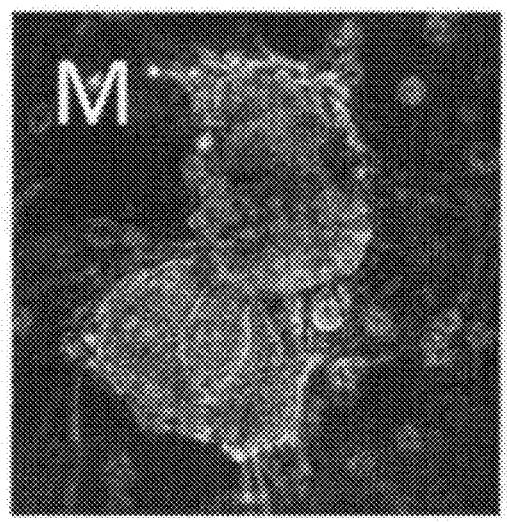
Figure 14N:
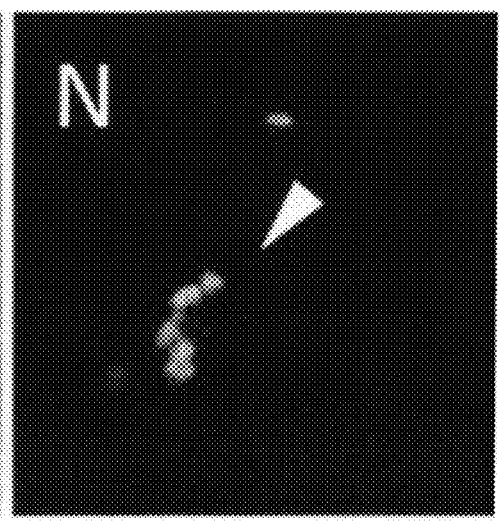

The primordial germ cells thus selected were transplanted into mouse blastocysts, and the embryos were transplanted into the uteri of recipients. After 10 days (the developmental stage of the embryos corresponded to E12.5 embryos), the embryos were analyzed. As a result, the primordial germ cell-like cells prepared from the normal ES cells formed few chimeras, whereas the Bcl-2-transfected primordial germ cells formed chimeras with a high frequency (FIG. 13B). In harvested gonads, the cells without the expression of Bcl-2 were not confirmed to form chimeras (FIGS. 13C and 13D), whereas the transplanted cells forced to express Bcl-2 exhibited high chimerism (FIGS. 13E and 13F). FIGS. 13C and 13E are bright field images. Frozen sections were further prepared from the gonads, and the detailed localization of the transplanted cells was verified by the fluorescent immunostaining method. As a result, the expressed germ cell markers vasa (FIG. 13G) and tdTomato (FIG. 13H) were shown to be costained (arrowheads in FIGS. 13G and 13F). This demonstrated that even if primordial germ cell-like cells whose cell death has been suppressed by the forced expression of Bcl-2 are introduced to embryos, chimeras can be formed with a high frequency. Also, the introduced primordial germ cell-like cells effectively contributed to germline cells.

Example 4B: Chimeric Animal Preparation by Introduction of Human iPS Cell Treated for Apoptosis Suppression In this Example, the effect of cell death suppression treatment on the ability of human iPS cells to form a chimera was verified.

First, the human iPS cells were prepared by the introduction of a reprogramming factor to human peripheral blood-derived cells using Sendai virus. Specifically, mononuclear cells obtained by the specific gravity centrifugation of human peripheral blood were transfected with Sendai virus polycistronically expressing OCT4, SOX2, KLF4, and MYC, seeded to a MEF feeder-coated plate, and then cultured for 2 consecutive weeks to obtain human iPS cells. After establishment of a line of the human iPS cells on a colony basis, siRNA was introduced into the cytoplasms to remove the Sendai virus vectors. The iPS cells thus obtained have no foreign gene. The human iPS cells were fluorescently labeled with lentivirus vectors for the constitutive expression of tdTomato gene operably linked to CAG promoter.

Next, the obtained iPS cells were infected by Tet-on AiLV expressing the Bcl-2 gene as described in Example 1A to obtain human iPS cells expressing Bcl-2 in a manner dependent on doxycycline. Human iPS cells untransfected with the Bcl-2 gene were used as a control.

The human iPS cells were caused to express Bcl-2 by treatment with 1 µg/mL doxycycline for 10 hours or longer. Then, the cells were transplanted into blastocyst-stage mouse embryos. The embryos were developed under culture until a developmental stage corresponding to the epiblast stage. Human iPS cells untransfected with the Bcl-2 gene were introduced to embryos of a control group. The distribution of the transplanted cells in the embryos was observed under a microscope up to 7 days after the transplantation.

As a result, in the embryos of the control group, the iPS cells immediately disappeared from the embryos (FIGS. 14G, 14H, 14K, and 14L), whereas the iPS cells caused to express Bcl-2 survived in the embryos over a long period even though the developmental stage of the mouse embryos was advanced (FIGS. 14E, 14F, 14I, 14J, 14M, and 14N). Specifically, in the case of using the human iPS cells as the cells for embryonic introduction, the cells contributed to chimeras by the apoptosis suppression treatment of the cells. This means that the human iPS cells acquired high ability to form a chimera by the apoptosis suppression treatment.

Example 4C: Chimeric Animal Preparation by Introduction of Marmoset ES Cell Subjected to Apoptosis Suppression Treatment In this Example, the effect of cell death suppression treatment on the ability of marmoset ES cells to form a chimera was verified.

First, ES cells were obtained from marmosets according to a routine method (Sasaki et al, 2005, Stem Cells). Next, marmoset ES cells forced to express human Bcl-2 gene were prepared using tet-on AiLV according to the preparation method described in Example 1A (test group). In order to discriminate the marmoset ES cells from mouse embryonic cells, the marmoset ES cells were transfected with CAG-tdTomato vectors according to the method described in Example 3B and thereby fluorescently labeled. Marmoset ES cells merely fluorescently labeled by the transfection of CAG-tdTomato vectors were used as a control.

The Bcl-2-expressing marmoset ES cells were caused to express Bcl-2 by treatment with 1 μg/mL (final concentration) doxycycline from 10 hours before transplantation. The marmoset ES cells were transplanted into mouse blastocysts to prepare chimeric embryos. The obtained chimeric embryos were transplanted into the uteri of recipient mice. Then, both the recipient mice of the test group and the control mice were each given a 2 mg/mL aqueous doxycycline solution until analysis so that the expression of Bcl-2 was maintained. Four days after the transplantation (the developmental stage of the mouse embryos corresponded to 6.5 days of pregnancy), the mouse embryos were analyzed.

Figure 15G:
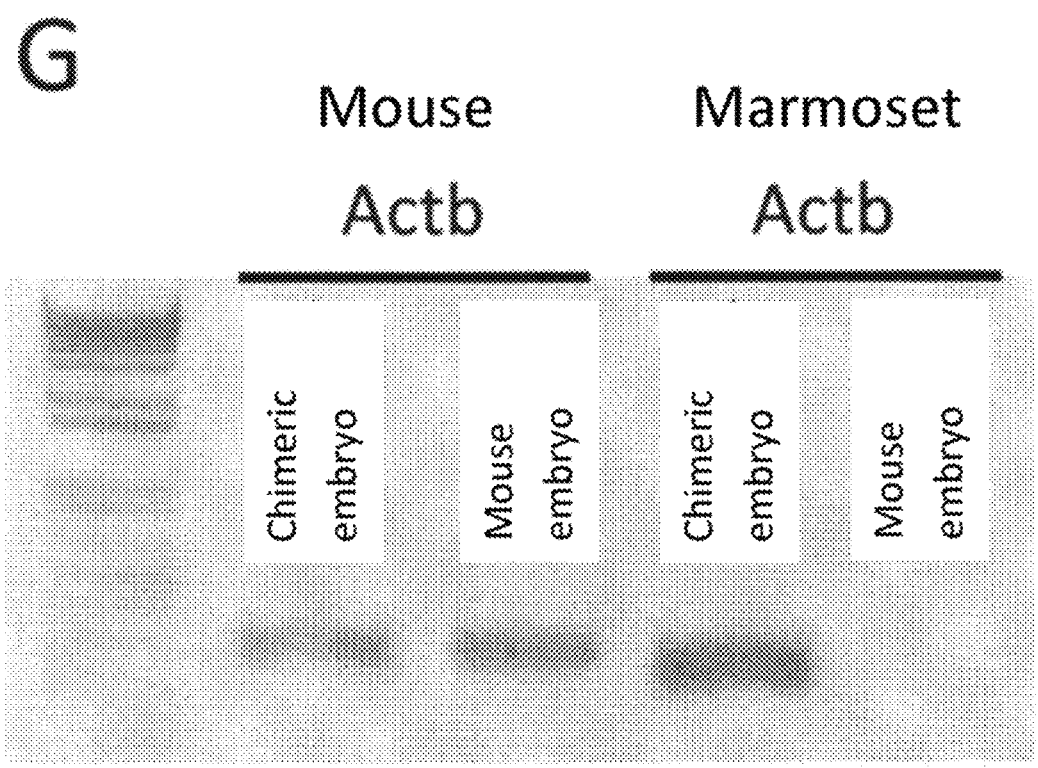

The results were as shown in FIG. 15. As seen from FIG. 15, fluorescence indicating the contribution of the marmoset ES cells was not observed in the mouse embryos harboring the control ES cells without the introduction of Bcl-2 (FIGS. 15A and 15B), whereas it was observed that the marmoset ES cells contributed to the embryos and formed chimeric embryos for the marmoset ES cells forced to express Bcl-2 (FIGS. 15C to 15F). When the marmoset ES cells forced to express Bcl-2 were used, the rate of chimera formation was approximately 58% (average of three experiments, n=38), showing a very high rate of chimera formation. When the control ES cells were used, chimera formation was not observed (average of two experiments, n=31). The contribution of the marmoset-derived cells in the mouse embryos was further confirmed by PCR. Specifically, primers for the specific amplification of each β actin gene (ACTB gene) were designed and used in PCR to confirm that chimeras were formed. The primers used for the amplification of the mouse ACTB gene were CAGCTTCTTTGCAGCTCCTT (SEQ ID NO: 1) and CTTCTCCATGTCGTCCCAGT (SEQ ID NO: 2). The primers used for the amplification of the marmoset ACTB gene were GGCATCCTGACCCTGAAGTA (SEQ ID NO: 3) and AGAGGCGTACAAGGAAAGCA (SEQ ID NO: 4). As shown in FIG. 15G, the presence of marmoset GAPDH was confirmed in the isolated mouse embryos, demonstrating that the introduced ES cells reliably contributed to the mouse embryos.

The results of Examples 4B and 4C indicate that the apoptosis suppression treatment of pluripotent stem cells (e.g., ES cells or iPS cells) of even non-rodent mammals such as humans or marmosets is effective for improving the ability to form a chimera.

As also seen from the results of Examples 4B and 4C, chimeric animals were obtained by the introduction of human iPS cells or marmoset ES cells to mouse embryos. It should be particularly noted that the human or the marmoset and the mouse largely differ in species. On the basis of these results, those skilled in the art can sufficiently understand that interspecific chimeric animals can be obtained from more related species.

Discussion

In Examples 2A to 4A, 1B and 2B, use of the cells having low ability to form a chimera or the cells having no ability to form a chimera enabled highly efficient preparation of chimeric animals, presumably because: in consideration of the results of this Example, the possibility is suggested that cells in the course of development cause cell death or apoptosis when placed in a different temporal and spatial environment, for example, in a region different from the original prospective fate. The phenomena observed in the present invention therefore seem to indicate that the cells can survive, by the suppression of their apoptosis, until the time when the developmental stage of embryos is adapted thereto.

According to Examples 3A and 3C, even the lineage-committed progenitor cells in an advanced developmental stage formed chimeric animals. This may imply that if the lineage-committed progenitor cells used in Examples 3A and 3C can survive by the cell death suppression treatment (e.g., apoptosis suppression treatment) until the cells are developed to an acceptable degree, the cells can contribute to tissues in the environment of embryos.

In the present invention, naïve pluripotent stem cells were able to be obtained from the primed pluripotent stem cells EpiSC. Thus, naïve pluripotent stem cells may be similarly obtained from the primed pluripotent stem cells of non-rodent mammals.

The invention claimed is:

1. A method for dedifferentiating a primed pluripotent stem cell, comprising:
   subjecting a primed pluripotent stem cell derived from a primate to an apoptosis suppression treatment that includes introducing an expression vector for expressing an anti-apoptotic gene into the primed pluripotent stem cell to induce expression of the anti-apoptotic gene in the primed pluripotent stem cell,
   wherein the expression of the anti-apoptotic gene occurs in the primed pluripotent stem cell and leads to production of a pluripotent stem cell less differentiated than before the apoptosis suppression treatment.

2. The method according to claim 1, wherein the pluripotent stem cell produced is capable of forming a multi-layer colony.

3. The method according to claim 1, wherein the pluripotent stem cell produced expresses CD31.

4. The method according to claim 1, wherein the pluripotent stem cell produced is a naïve pluripotent stem cell.

* * * * *